(12) United States Patent
Axten et al.

(10) Patent No.: US 7,982,053 B2
(45) Date of Patent: Jul. 19, 2011

(54) PEPTIDE DEFORMYLASE INHIBITORS

(75) Inventors: Jeffrey Michael Axten, Collegeville, PA (US); Jesus R. Medina, Collegeville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 610 days.

(21) Appl. No.: 11/996,994

(22) PCT Filed: Jul. 28, 2006

(86) PCT No.: PCT/US2006/029465
§ 371 (c)(1),
(2), (4) Date: Jan. 28, 2008

(87) PCT Pub. No.: WO2007/016364
PCT Pub. Date: Feb. 8, 2007

(65) Prior Publication Data
US 2009/0239866 A1    Sep. 24, 2009

Related U.S. Application Data

(60) Provisional application No. 60/704,183, filed on Jul. 29, 2005, provisional application No. 60/709,481, filed on Aug. 19, 2005.

(51) Int. Cl.
C07D 207/00 (2006.01)
C07D 295/00 (2006.01)
C07D 207/06 (2006.01)

(52) U.S. Cl. .......... 548/530; 548/537; 548/579

(58) Field of Classification Search .......... 548/530, 548/537, 579
See application file for complete search history.

(56) References Cited

U.S. PATENT DOCUMENTS
5,691,382 A    11/1997    Crimmin et al.

OTHER PUBLICATIONS

Marvin Miller, Synthesis and Therapeutic Potential of Hydroxamic Acid Based Siderophores and Analogues, 89 Chem. Rev. 1563 (1989).*

Antonello, et al., Anomalous Distance Dependence of Electron Transfer Across Peptide Bridges, *J. Am. Chem. Soc.*, 2003, vol. 125, No. 10, pp. 2874-2875.

* cited by examiner

*Primary Examiner* — Jeffrey S. Lundgren
*Assistant Examiner* — Sean Basquill
(74) *Attorney, Agent, or Firm* — Grace C. Hsu; John Lemanowicz

(57) ABSTRACT

Novel PDF inhibitors and novel methods for their use are provided.

8 Claims, No Drawings

PEPTIDE DEFORMYLASE INHIBITORS

This application is a 371 of International Application No. PCT/US2006/029465, filed 28 Jul. 2006, which claims priority to U.S. Provisional Application No. 60/704,183, filed 29 Jul. 2005 and U.S. Provisional Application No. 60/709,481, filed 19 Aug. 2005.

FIELD OF THE INVENTION

The present invention relates to the use of novel antibacterial compounds, and pharmaceutical compositions containing these compounds as peptide deformylase inhibitors.

BACKGROUND OF THE INVENTION

Bacterial initiator methionyl tRNA is modified by methionyl tRNA formyltransferase (FMT) to produce formyl-methionyl tRNA. The formyl methionine (f-met) is then incorporated at the N-termini of newly synthesized polypeptides. Polypeptide deformylase (PDF or Def) then deformylates primary translation products to produce N-methionyl polypeptides. Most intracellular proteins are further processed by methionine amino peptidase (MAP) to yield the mature peptide and free methionine, which is recycled. PDF and MAP are both essential for bacterial growth, and PDF is required for MAP activity.

Polypeptide deformylase is found in all eubacteria for which high coverage genomic sequence information is available. Sequence diversity among PDF homologs is high, with as little as 20% identity between distantly related sequences. However, conservation around the active site is very high, with several completely conserved residues, including one cysteine and two histidines which are required to coordinate the active site metal (Meinnel, T. et al., J. Mol. Biol. 267, 749-761, 1997).

PDF is recognized to be an attractive antibacterial target, as this enzyme has been demonstrated to be essential for bacterial growth in vitro (Mazel, D. et al., EMBO J. 13 (4), 914-923, 1994), is not believed to be involved in eukaryotic protein synthesis (Rajagopalan et al., J. Am. Chem. Soc. 119, 12418-12419, 1997), and is universally conserved in prokaryotes (Kozak, M., Microbiol. Rev. 47, 1-45, 1983). Therefore PDF inhibitors can potentially serve as broad spectrum antibacterial agents, and has been a subject of several reviews (Jain et al., Current Medicinal Chemistry, 12, 1607-1621, 2005; Johnson et al., Current Drug Targets: Infectious Disorders, 5, 39-52, 2005; Boularot et al., Current Opinion in Investigational Drugs, 5, 809-822, 2004; Giglione et al., Molecular Microbiology, 36, 1197-1205, 2000.

SUMMARY OF THE INVENTION

The present invention involves novel antibacterial compounds represented by Formula (I) herein below and their use as PDF inhibitors.

DETAILED DESCRIPTION OF THE INVENTION

In one aspect of the present invention, there is provided a compound of Formula (I):

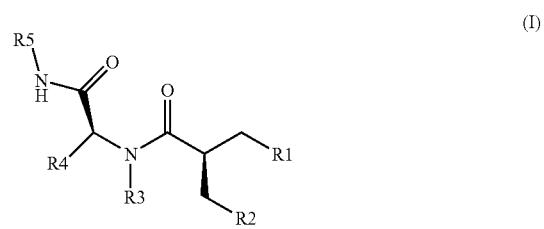

(I)

wherein:
R1 is selected from —C(O)—NH(OH) or —N(OH)—CHO;
R2 is selected from:
   1) $C_1$-$C_6$-alkyl,
   2) $C_3$-$C_7$-cycloalkyl,
   3) aryl, and
   4) heteroaryl,
   where said $C_1$-$C_6$-alkyl is optionally substituted by one to three R6 groups; said $C_3$-$C_7$-cycloalkyl, aryl, and heteroaryl are each optionally substituted by one to three R7 groups;
R3 and R4 are joined together to form a 5-7 seven membered heterocycloalkyl ring optionally substituted with one or two $C_1$-$C_3$-alkyl groups which can be attached to the same carbon atom and optionally joined together to form a spiro ring system with said 5-7 membered heterocycloalkyl ring; or R3 is selected from: H and $C_1$-$C_6$-alkyl; and R4 is the amino acid side chain of: glycine, alanine, valine, leucine, tert-leucine, isoleucine, phenylalanine, serine, threonine, tyrosine, cysteine, methionine, lysine, arginine, histidine, tryptophan, aspartic acid, glutamic acid, asparagine, or glutamine;
R5 is selected from:
   1) —C(O)R8,
   2) —C(O)OR8, and
   3) —C(O)NR8R9;
each R6 is independently selected from:
   1) OH,
   2) $CF_3$,
   3) —NR9R9,
   4) cyano,
   5) —O—$C_1$-$C_3$-alkyl,
   6) phenyl,
   7) heteroaryl,
   8) heterocycloalkyl,
   9) —NHC(O)OC$_1$-$C_6$-alkyl, and
   10) —NHCOH;
each R7 is independently selected from:
   1) OH,
   2) halo,
   3) cyano,
   4) nitro,
   5) —NR9R9,
   6) $CF_3$,
   7) —NHC(O)$CH_3$,
   8) —$OCH_3$,
   9) $C_1$-$C_6$-alkyl,
   10) heteroaryl, and
   11) heterocycloalkyl;
R8 is selected from:
   1) $C_1$-$C_6$-alkyl,
   2) $C_2$-$C_6$-alkenyl,
   3) $C_3$-$C_7$-cycloalkyl,
   4) phenyl,
   5) heteroaryl, and
   6) heterocycloalkyl,
   where said $C_1$-$C_6$-alkyl is optionally substituted by one to three R6 groups; said $C_3$-$C_7$-cycloalkyl, phenyl, and heteroaryl are each optionally substituted by one to three R7 groups; and said heterocycloalkyl is optionally substituted by one to three R10 groups;

each R9 is independently selected from:
1) H and
2) $C_1$-$C_6$-alkyl; and each R10 is independently selected from
1) OH,
2) $C_1$-$C_6$-alkyl,
3) phenyl,
4) $NH_2$, and
5) —C(O)O$C_1$-$C_6$-alkyl.

In one embodiment R1 is —N(OH)—CHO.

In another embodiment R2 is unsubstituted $C_1$-$C_6$-alkyl or $C_3$-$C_7$-cycloalkyl.

In another embodiment R2 is unsubstituted n-butyl or cyclopentyl.

In another embodiment R3 and R4 are joined together to form a pyrrolidinyl ring, optionally substituted with one or two $C_1$-$C_3$-alkyl groups.

In another embodiment R3 and R4 are joined together to form 3,3-dimethyl-pyrrolidinyl ring.

In another embodiment R3 and R4 are joined together to form an unsubstituted pyrrolidinyl ring.

In another embodiment R3 is H and R4 is the amino acid side chain of tert-leucine.

In another embodiment R1 is —N(OH)—CHO, R2 is unsubstituted cyclopentyl, and R3 and R4 are joined together to form an unsubstituted pyrrolidinyl ring.

Compounds useful in the present invention are selected from the group consisting of:

1-((2R)-3-cyclopentyl-2-{[formyl(hydroxy)amino]methyl}propanoyl)-N-[(4-fluorophenyl)carbonyl]-L-prolinamide;

N-acetyl-1-((2R)-3-cyclopentyl-2-{[formyl(hydroxy)amino]methyl}propanoyl)-L-prolinamide;

1-((2R)-3-cyclopentyl-2-{[formyl(hydroxy)amino]methyl}propanoyl)-N-(phenylcarbonyl)-L-prolinamide;

N-{[4-(acetylamino)phenyl]carbonyl}-1-((2R)-3-cyclopentyl-2-{[formyl(hydroxy)amino]methyl}propanoyl)-L-prolinamide;

1-((2R)-3-cyclopentyl-2-{[formyl(hydroxy)amino]methyl}propanoyl)-N-[(methyloxy)acetyl]-L-prolinamide;

N-[1-((2R)-3-cyclopentyl-2-{[formyl(hydroxy)amino]methyl}propanoyl)-L-prolyl]-6-(trifluoromethyl)-3-pyridinecarboxamide;

1-((2R)-3-cyclopentyl-2-{[formyl(hydroxy)amino]methyl}propanoyl)-N-[(1,5-dimethyl-1H-pyrazol-3-yl)carbonyl]-L-prolinamide;

1-((2R)-3-cyclopentyl-2-{[formyl(hydroxy)amino]methyl}propanoyl)-N-[(1,3-dimethyl-1H-pyrazol-5-yl)carbonyl]-L-prolinamide;

1-((2R)-3-cyclopentyl-2-{[formyl(hydroxy)amino]methyl}propanoyl)-N-[(5-methyl-3-isoxazolyl)carbonyl]-L-prolinamide;

1-((2R)-3-cyclopentyl-2-{[formyl(hydroxy)amino]methyl}propanoyl)-N-[(2-fluorophenyl)carbonyl]-L-prolinamide;

1-((2R)-3-cyclopentyl-2-{[formyl(hydroxy)amino]methyl}propanoyl)-N-[(3-fluorophenyl)carbonyl]-L-prolinamide;

1-((2R)-3-cyclopentyl-2-{[formyl(hydroxy)amino]methyl}propanoyl)-N-[(3-fluoro-4-methylphenyl)carbonyl]-L-prolinamide;

N-[1-((2R)-3-cyclopentyl-2-{[formyl(hydroxy)amino]methyl}propanoyl)-L-prolyl]-4-morpholinecarboxamide;

N-[(3-cyanophenyl)carbonyl]-1-((2R)-3-cyclopentyl-2-{[formyl(hydroxy)amino]methyl}propanoyl)-L-prolinamide;

1-((2R)-3-cyclopentyl-2-{[formyl(hydroxy)amino]methyl}propanoyl)-N-[(2,5-difluorophenyl)carbonyl]-L-prolinamide;

1-((2R)-3-cyclopentyl-2-{[formyl(hydroxy)amino]methyl}propanoyl)-N-[(methyloxy)carbonyl]-L-prolinamide;

N-[1-((2R)-3-cyclopentyl-2-{[formyl(hydroxy)amino]methyl}propanoyl)-L-prolyl]-4-pyridinecarboxamide;

1-((2R)-3-cyclopentyl-2-{[formyl(hydroxy)amino]methyl}propanoyl)-N-[(2,6-difluorophenyl)carbonyl]-L-prolinamide;

N-{[(trans-4-aminocyclohexyl)oxy]carbonyl}-1-((2R)-3-cyclopentyl-2-{[formyl(hydroxy)amino]methyl}propanoyl)-L-prolinamide;

N-[1-((2R)-3-cyclopentyl-2-{[formyl(hydroxy)amino]methyl}propanoyl)-L-prolyl]-6-(4-morpholinyl)-3-pyridinecarboxamide;

1-((2R)-3-cyclopentyl-2-{[formyl(hydroxy)amino]methyl}propanoyl)-N-{[4-(1H-pyrazol-1-yl)phenyl]carbonyl}-L-prolinamide;

1-((2R)-3-cyclopentyl-2-{[formyl(hydroxy)amino]methyl}propanoyl)-N-{[(phenylmethyl)oxy]carbonyl}-L-prolinamide;

1-((2R)-3-cyclopentyl-2-{[formyl(hydroxy)amino]methyl}propanoyl)-N-[(ethyloxy)carbonyl]-L-prolinamide;

1-((2R)-3-cyclopentyl-2-{[formyl(hydroxy)amino]methyl}propanoyl)-N-[(tetrahydro-2H-pyran-4-yloxy)carbonyl]-L-prolinamide;

1-((2R)-3-cyclopentyl-2-{[formyl(hydroxy)amino]methyl}propanoyl)-N-[(cyclopentyloxy)carbonyl]-L-prolinamide;

1-((2R)-3-cyclopentyl-2-{[formyl(hydroxy)amino]methyl}propanoyl)-N-{[4-(1H-imidazol-1-yl)phenyl]carbonyl}-L-prolinamide;

N-[(cyclohexyloxy)carbonyl]-1-((2R)-3-cyclopentyl-2-{[formyl(hydroxy)amino]methyl}propanoyl)-L-prolinamide;

1-((2R)-3-cyclopentyl-2-{[formyl(hydroxy)amino]methyl}propanoyl)-N-(2-thienylcarbonyl)-L-prolinamide;

1-((2R)-3-cyclopentyl-2-{[formyl(hydroxy)amino]methyl}propanoyl)-N-[(2-propen-1-yloxy)carbonyl]-L-prolinamide;

2,3-dihydro[1,4]dioxino[2,3-c]pyridin-7-ylmethyl[1-((2R)-3-cyclopentyl-2-{[formyl(hydroxy)amino]methyl}propanoyl)-L-prolyl]carbamate;

N-[(cyclobutyloxy)carbonyl]-1-((2R)-3-cyclopentyl-2-{[(formyl(hydroxy)amino]methyl}propanoyl)-L-prolinamide;

1-((2R)-3-cyclopentyl-2-{[formyl(hydroxy)amino]methyl}propanoyl)-N-{[(1,1-dimethylethyl)oxy]carbonyl}-L-prolinamide;

1-((2R)-3-cyclopentyl-2-{[formyl(hydroxy)amino]methyl}propanoyl)-N-({[trans-4-(dimethylamino)cyclohexyl]oxy}carbonyl)-L-prolinamide;

N-{[(trans-3-aminocyclobutyl)oxy]carbonyl}-1-((2R)-3-cyclopentyl-2-{[formyl(hydroxy)amino]methyl}propanoyl)-L-prolinamide;

1-((2R)-3-cyclopentyl-2-{[formyl(hydroxy)amino]methyl}propanoyl)-N-{[4-(4-ethyl-1-piperazinyl)phenyl]carbonyl}-L-prolinamide;

1-((2R)-3-cyclopentyl-2-{[formyl(hydroxy)amino]methyl}propanoyl)-N-(2,2-dimethylpropanoyl)-L-prolinamide;

1-((2R)-3-cyclopentyl-2-{[formyl(hydroxy)amino]methyl}propanoyl)-N-{[(1-methylethyl)oxy]carbonyl}-L-prolinamide;

1-((2R)-3-cyclopentyl-2-{[formyl(hydroxy)amino]methyl}propanoyl)-N-{[(1-methyl-3-pyrrolidinyl)oxy]carbonyl}-L-prolinamide (mixture of diastereomers);

1-((2R)-3-cyclopentyl-2-{[formyl(hydroxy)amino]methyl}propanoyl)-N-{[(3R)-tetrahydro-3-furanyloxy]carbonyl}-L-prolinamide;

1-((2R)-3-cyclopentyl-2-{[formyl(hydroxy)amino]methyl}propanoyl)-N-{[(3S)-tetrahydro-3-furanyloxy]carbonyl}-L-prolinamide;

1-methyl-3-piperidinyl[1-((2R)-3-cyclopentyl-2-{[formyl(hydroxy)amino]methyl}propanoyl)-L-prolyl]carbamate (mixture of diastereomers);

1-((2R)-3-cyclopentyl-2-{[formyl(hydroxy)amino]methyl}propanoyl)-N-({[1-(1-methylethyl)-3-pyrrolidinyl]oxy}carbonyl)-L-prolinamide (mixture of diastereomers);

1-((2R)-3-cyclopentyl-2-{[formyl(hydroxy)amino]methyl}propanoyl)-N-(4-isoxazolylcarbonyl)-L-prolinamide;

1-((2R)-3-cyclopentyl-2-{[formyl(hydroxy)amino]methyl}propanoyl)-N-[(tetrahydro-2H-thiopyran-4-yloxy)carbonyl]-L-prolinamide;

1-((2R)-3-cyclopentyl-2-{[formyl(hydroxy)amino]methyl}propanoyl)-N-{[(1,1-dioxidotetrahydro-2H-thiopyran-4-yl)oxy]carbonyl}-L-prolinamide;

1-((2R)-3-cyclopentyl-2-{[formyl(hydroxy)amino]methyl}propanoyl)-N-({[(1S)-1-methyl-2-(methyloxy)ethyl]oxy}carbonyl)-L-prolinamide;

1-((2R)-3-cyclopentyl-2-{[formyl(hydroxy)amino]methyl}propanoyl)-N-({[(1R)-1-methyl-2-(methyloxy)ethyl]oxy}carbonyl)-L-prolinamide;

1-((2R)-3-cyclopentyl-2-{[formyl(hydroxy)amino]methyl}propanoyl)-N-{[4-(1-piperazinyl)phenyl]carbonyl}-L-prolinamide;

1-((2R)-3-cyclopentyl-2-{[formyl(hydroxy)amino]methyl}propanoyl)-N-(2-methylpropanoyl)-L-prolinamide;

1-((2R)-3-cyclopentyl-2-{[formyl(hydroxy)amino]methyl}propanoyl)-N-(3-methylbutanoyl)-L-prolinamide;

N-[1-((2R)-3-cyclopentyl-2-{[formyl(hydroxy)amino]methyl}propanoyl)-L-prolyl]-2-pyridinecarboxamide;

N-[1-((2R)-3-cyclopentyl-2-{[formyl(hydroxy)amino]methyl}propanoyl)-L-prolyl]-3-pyridinecarboxamide;

N-(cyclobutylcarbonyl)-1-((2R)-3-cyclopentyl-2-{[formyl(hydroxy)amino]methyl}propanoyl)-L-prolinamide;

1-((2R)-3-cyclopentyl-2-{[formyl(hydroxy)amino]methyl}propanoyl)-N-[(ethylamino)carbonyl]-L-prolinamide;

1-((2R)-3-cyclopentyl-2-{[formyl(hydroxy)amino]methyl}propanoyl)-N-(cyclopropylcarbonyl)-L-prolinamide;

N-(cyclopentylacetyl)-1-((2R)-3-cyclopentyl-2-{[formyl(hydroxy)amino]methyl}propanoyl)-L-prolinamide;

N-(cyclopentylcarbonyl)-1-((2R)-3-cyclopentyl-2-{[formyl(hydroxy)amino]methyl}propanoyl)-L-prolinamide;

N-(cyclohexylcarbonyl)-1-((2R)-3-cyclopentyl-2-{[formyl(hydroxy)amino]methyl}propanoyl)-L-prolinamide;

1,1-dimethylethyl 3-({[1-((2R)-3-cyclopentyl-2-{[formyl(hydroxy)amino]methyl}propanoyl)-L-prolyl]amino}carbonyl)-1-pyrrolidinecarboxylate (mixture of diastereomers);

N-(cyclopentylcarbonyl)-1-((2R)-2-{[formyl(hydroxy)amino]methyl}heptanoyl)-L-prolinamide;

N-(2,2-dimethylpropanoyl)-1-((2R)-2-{[formyl(hydroxy)amino]methyl}heptanoyl)-L-prolinamide;

1-((2R)-3-cyclopentyl-2-{[formyl(hydroxy)amino]methyl}propanoyl)-N-({[(methyloxy)carbonyl]amino}carbonyl)-L-prolinamide;

1-((2R)-3-cyclopentyl-2-{[formyl(hydroxy)amino]methyl}propanoyl)-N-{[(1,1-dimethylethyl)amino]carbonyl}-L-prolinamide;

N-{[(1,1-dimethylethyl)oxy]carbonyl}-1-((2R)-2-{[formyl(hydroxy)amino]methyl}heptanoyl)-L-prolinamide;

N-[(ethylamino)carbonyl]-1-((2R)-2-{[formyl(hydroxy)amino]methyl}heptanoyl)-L-prolinamide;

$N^1$-(cyclopentylcarbonyl)-$N^2$-((2R)-3-cyclopentyl-2-{[formyl(hydroxy)amino]methyl}propanoyl)-3-methyl-L-valinamide;

$N^2$-((2R)-3-cyclopentyl-2-{[formyl(hydroxy)amino]methyl}propanoyl)-$N^1$-(2,2-dimethylpropanoyl)-3-methyl-L-valinamide;

$N^2$-((2R)-3-cyclopentyl-2-{[formyl(hydroxy)amino]methyl}propanoyl)-$N^1$-{[(1,1-dimethylethyl)oxy]carbonyl}-3-methyl-L-valinamide;

1-((2R)-3-cyclopentyl-2-{[formyl(hydroxy)amino]methyl}propanoyl)-N-{[(1-methylethyl)amino]carbonyl}-L-prolinamide;

N-[(cyclopentylamino)carbonyl]-1-((2R)-3-cyclopentyl-2-{[formyl(hydroxy)amino]methyl}propanoyl)-L-prolinamide;

N-[(butylamino)carbonyl]-1-((2R)-3-cyclopentyl-2-{[formyl(hydroxy)amino]methyl}propanoyl)-L-prolinamide;

$N^2$-((2R)-3-cyclopentyl-2-{[formyl(hydroxy)amino]methyl}propanoyl)-$N^1$-[(ethylamino)carbonyl]-3-methyl-L-valinamide;

1-((2R)-3-cyclopentyl-2-{[formyl(hydroxy)amino]methyl}propanoyl)-N-({[4-(methyloxy)phenyl]amino}carbonyl)-L-prolinamide;

N-[(cyclohexylamino)carbonyl]-1-((2R)-3-cyclopentyl-2-{[formyl(hydroxy)amino]methyl}propanoyl)-L-prolinamide;

$N^2$-((2R)-3-cyclopentyl-2-{[formyl(hydroxy)amino]methyl}propanoyl)-3-methyl-$N^1$-[(methyloxy)carbonyl]-L-valinamide;

1-((2R)-3-cyclopentyl-2-{[formyl(hydroxy)amino]methyl}propanoyl)-N-[(propylamino)carbonyl]-L-prolinamide;

1-((2R)-3-cyclopentyl-2-{[formyl(hydroxy)amino]methyl}propanoyl)-N-[(2-propen-1-ylamino)carbonyl]-L-prolinamide;

1-((2R)-3-cyclopentyl-2-{[formyl(hydroxy)amino]methyl}propanoyl)-N-[(dimethylamino)carbonyl]-L-prolinamide;

1-((2R)-3-cyclopentyl-2-{[formyl(hydroxy)amino]methyl}propanoyl)-N-{[(phenylmethyl)amino]carbonyl}-L-prolinamide;

1-((2R)-3-cyclopentyl-2-{[formyl(hydroxy)amino]methyl}propanoyl)-3,3-dimethyl-N-[(methyloxy)carbonyl]-L-prolinamide;

1-((2R)-3-cyclopentyl-2-{[formyl(hydroxy)amino]methyl}propanoyl)-N-{[(2-phenylethyl)amino]carbonyl}-L-prolinamide;

1-((2R)-3-cyclopentyl-2-{[formyl(hydroxy)amino] methyl}propanoyl)-N-[(methylamino)carbonyl]-L-prolinamide;

1-((2R)-3-cyclopentyl-2-{[formyl(hydroxy)amino] methyl}propanoyl)-N-{[(4-phenylbutyl)amino]carbonyl}-L-prolinamide;

1-((2R)-3-cyclopentyl-2-{[formyl(hydroxy)amino] methyl}propanoyl)-N-({[(2S)-2-hydroxypropyl] amino}carbonyl)-L-prolinamide;

1-((2R)-3-cyclopentyl-2-{[formyl(hydroxy)amino] methyl}propanoyl)-N-({[(2R)-2-hydroxypropyl] amino}carbonyl)-L-prolinamide;

1-((2R)-3-cyclopentyl-2-{[formyl(hydroxy)amino] methyl}propanoyl)-N-({[2-(3-pyridinyl)ethyl] amino}carbonyl)-L-prolinamide hydrochloride;

1-((2R)-3-cyclopentyl-2-{[formyl(hydroxy)amino] methyl}propanoyl)-N-{[(3-phenylpropyl)amino]carbonyl}-L-prolinamide;

N-({[2-(1-benzofuran-2-yl)ethyl]amino}carbonyl)-1-((2R)-3-cyclopentyl-2-{[formyl(hydroxy)amino] methyl}propanoyl)-L-prolinamide;

1-((2R)-3-cyclopentyl-2-{[formyl(hydroxy)amino] methyl}propanoyl)-N-({[2-(3,5-dimethyl-1H-pyrazol-4-yl)ethyl]amino}carbonyl)-L-prolinamide;

ethyl 4-[({[1-((2R)-3-cyclopentyl-2-{[formyl(hydroxy) amino]methyl}propanoyl)-L-prolyl]amino}carbonyl) amino]-1-piperidinecarboxylate;

1-((2R)-3-cyclopentyl-2-{[formyl(hydroxy)amino] methyl}propanoyl)-N-({[2-(2-pyridinyl)ethyl] amino}carbonyl)-L-prolinamide;

1-((2R)-3-cyclopentyl-2-{[formyl(hydroxy)amino] methyl}propanoyl)-N-({[2-(2-pyrazinyl)ethyl] amino}carbonyl)-L-prolinamide;

1-((2R)-3-cyclopentyl-2-{[formyl(hydroxy)amino] methyl}propanoyl)-N-({[2-(4-pyridinyl)ethyl] amino}carbonyl)-L-prolinamide;

1-((2R)-3-cyclopentyl-2-{[formyl(hydroxy)amino] methyl}propanoyl)-N-{[(4-hydroxybutyl)amino]carbonyl}-L-prolinamide;

1-((2R)-3-cyclopentyl-2-{[formyl(hydroxy)amino] methyl}propanoyl)-N-{[(5-hydroxypentyl)amino]carbonyl}-L-prolinamide;

1-((2R)-3-cyclopentyl-2-{[formyl(hydroxy)amino] methyl}propanoyl)-N-({[3-(dimethylamino)propyl] amino}carbonyl)-L-prolinamide;

1-((2R)-3-cyclopentyl-2-{[formyl(hydroxy)amino] methyl}propanoyl)-N-[({2-[5-(methyloxy)-1H-indol-3-yl]ethyl}amino)carbonyl]-L-prolinamide;

1-((2R)-3-cyclopentyl-2-{[formyl(hydroxy)amino] methyl}propanoyl)-N-({[3-(2-oxo-1-pyrrolidinyl)propyl] amino}carbonyl)-L-prolinamide;

1-((2R)-3-cyclopentyl-2-{[formyl(hydroxy)amino] methyl}propanoyl)-N-({[(1-methyl-1H-imidazol-2-yl) methyl]amino}carbonyl)-L-prolinamide;

1-((2R)-3-cyclopentyl-2-{[formyl(hydroxy)amino] methyl}propanoyl)-N-({[(1,5-dimethyl-1H-pyrazol-4-yl) methyl]amino}carbonyl)-L-prolinamide;

1-((2R)-3-cyclopentyl-2-{[formyl(hydroxy)amino] methyl}propanoyl)-N-({[3-(4-morpholinyl)propyl] amino}carbonyl)-L-prolinamide;

1-((2R)-3-cyclopentyl-2-{[formyl(hydroxy)amino] methyl}propanoyl)-N-{[(2-phenylpropyl)amino]carbonyl}-L-prolinamide (mixture of diastereomers);

1-((2R)-3-cyclopentyl-2-{[formyl(hydroxy)amino] methyl}propanoyl)-N-({[2-(1-piperidinyl)ethyl] amino}carbonyl)-L-prolinamide formate;

1-((2R)-3-cyclopentyl-2-{[formyl(hydroxy)amino] methyl}propanoyl)-N-{[(2-hydroxyethyl)amino]carbonyl}-L-prolinamide;

1-((2R)-3-cyclopentyl-2-{[formyl(hydroxy)amino] methyl}propanoyl)-N-({[2-(1-pyrrolidinyl)ethyl] amino}carbonyl)-L-prolinamide formate;

1-((2R)-3-cyclopentyl-2-{[formyl(hydroxy)amino] methyl}propanoyl)-N-[({3-[(1-methylethyl)oxy] propyl}amino)carbonyl]-L-prolinamide;

N-({[2-(4-aminophenyl)ethyl]amino}carbonyl)-1-((2R)-3-cyclopentyl-2-{[formyl(hydroxy)amino] methyl}propanoyl)-L-prolinamide;

1-((2R)-3-cyclopentyl-2-{[formyl(hydroxy)amino] methyl}propanoyl)-N-{[(3-hydroxypropyl)amino]carbonyl}-L-prolinamide;

N-(aminocarbonyl)-1-((2R)-3-cyclopentyl-2-{[formyl(hydroxy)amino]methyl}propanoyl)-3,3-dimethyl-L-prolinamide;

1-((2R)-3-cyclopentyl-2-{[formyl(hydroxy)amino] methyl}propanoyl)-N-[(cyclopropylamino)carbonyl]-3,3-dimethyl-L-prolinamide;

1-((2R)-3-cyclopentyl-2-{[formyl(hydroxy)amino] methyl}propanoyl)-3,3-dimethyl-N-{[(3R)-tetrahydro-3-furanyloxy]carbonyl}-L-prolinamide;

1-((2R)-3-cyclopentyl-2-{[formyl(hydroxy)amino] methyl}propanoyl)-N-{[(tetrahydro-2-furanylmethyl) amino]carbonyl}-L-prolinamide (mixture of diastereomers);

N-[(cyclobutylamino)carbonyl]-1-((2R)-3-cyclopentyl-2-{[formyl(hydroxy)amino]methyl}propanoyl)-L-prolinamide;

N-({[2-(6-amino-5-fluoro-3-pyridinyl)ethyl] amino}carbonyl)-1-((2R)-3-cyclopentyl-2-{[formyl(hydroxy)amino]methyl}propanoyl)-L-prolinamide;

1-((2R)-3-cyclopentyl-2-{[formyl(hydroxy)amino] methyl}propanoyl)-3,3-dimethyl-N-{[(2-oxetanylmethyl) oxy]carbonyl}-L-prolinamide;

1-((2R)-3-cyclopentyl-2-{[formyl(hydroxy)amino] methyl}propanoyl)-N-[(ethylamino)carbonyl]-3,3-dimethyl-L-prolinamide;

1-((2R)-3-cyclopentyl-2-{[formyl(hydroxy)amino] methyl}propanoyl)-N-[(cyclopropylamino)carbonyl]-L-prolinamide;

1-((2R)-3-cyclopentyl-2-{[formyl(hydroxy)amino] methyl}propanoyl)-3,3-dimethyl-N-[(methylamino)carbonyl]-L-prolinamide;

1-((2R)-3-cyclopentyl-2-{[formyl(hydroxy)amino] methyl}propanoyl)-3,3-dimethyl-N-({[(3-methyl-3-oxetanyl)methyl]oxy}carbonyl)-L-prolinamide;

1-((2R)-3-cyclopentyl-2-{[formyl(hydroxy)amino] methyl}propanoyl)-3,3-dimethyl-N-[(3-oxetanyloxy)carbonyl]-L-prolinamide;

1-((2R)-3-cyclopentyl-2-{[formyl(hydroxy)amino] methyl}propanoyl)-N-{[(3S)-tetrahydro-3-furanylamino] carbonyl}-L-prolinamide;

1-((2R)-3-cyclopentyl-2-{[formyl(hydroxy)amino] methyl}propanoyl)-N-{[(3-methylbutyl)amino]carbonyl}-L-prolinamide;

1-((2R)-3-cyclopentyl-2-{[formyl(hydroxy)amino] methyl}propanoyl)-N-({[2-(4-pyridazinyl)ethyl] amino}carbonyl)-L-prolinamide;

1-((2R)-3-cyclopentyl-2-{[formyl(hydroxy)amino] methyl}propanoyl)-3,3-dimethyl-N-({[(1S)-1-methyl-2-(methyloxy)ethyl]oxy}carbonyl)-L-prolinamide;

1-((2R)-3-cyclopentyl-2-{[formyl(hydroxy)amino] methyl}propanoyl)-3,3-dimethyl-N-({[(1R)-1-methyl-2-(methyloxy)ethyl]oxy}carbonyl)-L-prolinamide;

1-((2R)-3-cyclopentyl-2-{[formyl(hydroxy)amino]
methyl}propanoyl)-3,3-dimethyl-N-[(tetrahydro-2H-pyran-4-yloxy)carbonyl]-L-prolinamide;
1-((2R)-3-cyclopentyl-2-{[formyl(hydroxy)amino]
methyl}propanoyl)-N-({[2-(methyloxy)ethyl]
amino}carbonyl)-L-prolinamide;
N-(aminocarbonyl)-1-((2R)-3-cyclopentyl-2-{[formyl(hydroxy)amino]methyl}propanoyl)-L-prolinamide;
N-{[(trans-3-cyanocyclobutyl)amino]carbonyl}-1-((2R)-3-cyclopentyl-2-{[formyl(hydroxy)amino]
methyl}propanoyl)-L-prolinamide;
1-((2R)-3-cyclopentyl-2-{[formyl(hydroxy)amino]
methyl}propanoyl)-N-{[(1-hydroxy-1,2,3,4-tetrahydro-2-naphthalenyl)amino]carbonyl}-L-prolinamide (mixture of trans-diastereomers);
1-((2R)-3-cyclopentyl-2-{[formyl(hydroxy)amino]
methyl}propanoyl)-3,3-dimethyl-N-{[(3S)-tetrahydro-3-furanyloxy]carbonyl}-L-prolinamide;
N-({[2-(6-amino-5-chloro-3-pyridinyl)ethyl]
amino}carbonyl)-1-((2R)-3-cyclopentyl-2-{[formyl(hydroxy)amino]methyl}propanoyl)-L-prolinamide;
1-((2R)-3-cyclopentyl-2-{[formyl(hydroxy)amino]
methyl}propanoyl)-N-{[(2,3-dihydro-1,4-benzodioxin-2-ylmethyl)amino]carbonyl}-L-prolinamide (mixture of diastereomers);
1-((2R)-3-cyclopentyl-2-{[formyl(hydroxy)amino]
methyl}propanoyl)-N-{[(2-imidazo[1,2-a]pyridin-6-yl-ethyl)amino]carbonyl}-L-prolinamide formate;
N-[(cyclobutyloxy)carbonyl]-1-((2R)-3-cyclopentyl-2-{[formyl(hydroxy)amino]methyl}propanoyl)-3,3-dimethyl-L-prolinamide;
1-((2R)-3-cyclopentyl-2-{[formyl(hydroxy)amino]
methyl}propanoyl)-N-({[(2S)-2-hydroxy-2-phenylethyl]
amino}carbonyl)-L-prolinamide;
1-((2R)-3-cyclopentyl-2-{[formyl(hydroxy)amino]
methyl}propanoyl)-N-({[(2R)-2-hydroxy-2-phenylethyl]
amino}carbonyl)-L-prolinamide;
1-((2R)-3-cyclopentyl-2-{[formyl(hydroxy)amino]
methyl}propanoyl)-N-{[(5-methyl-1H-pyrazol-3-yl)
amino]carbonyl}-L-prolinamide;
1-((2R)-3-cyclopentyl-2-{[formyl(hydroxy)amino]
methyl}propanoyl)-N-[(2,3-dihydro-1H-inden-2-ylamino)carbonyl]-L-prolinamide;
1-((2R)-3-cyclopentyl-2-{[formyl(hydroxy)amino]
methyl}propanoyl)-N-({[2-(1H-pyrazol-1-yl)ethyl]
amino}carbonyl)-L-prolinamide;
1-((2R)-3-cyclopentyl-2-{[formyl(hydroxy)amino]
methyl}propanoyl)-N-({[2-(diethylamino)ethyl]
amino}carbonyl)-L-prolinamide;
1-((2R)-3-cyclopentyl-2-{[formyl(hydroxy)amino]
methyl}propanoyl)-N-{[(2-fluoroethyl)amino]carbonyl}-L-prolinamide;
1-((2R)-3-cyclopentyl-2-{[formyl(hydroxy)amino]
methyl}propanoyl)-N-({[3-(diethylamino)propyl]
amino}carbonyl)-L-prolinamide;
1-((2R)-3-cyclopentyl-2-{[formyl(hydroxy)amino]
methyl}propanoyl)-N-({[3-(methyloxy)propyl]
amino}carbonyl)-L-prolinamide;
N-({[3,3-bis(ethyloxy)propyl]amino}carbonyl)-1-((2R)-3-cyclopentyl-2-{[formyl(hydroxy)amino]
methyl}propanoyl)-L-prolinamide;
1-((2R)-3-cyclopentyl-2-{[formyl(hydroxy)amino]
methyl}propanoyl)-N-({[3-({[(1,1-dimethylethyl)oxy]
carbonyl}amino)propyl]amino}carbonyl)-L-prolinamide; and
1-((2R)-3-cyclopentyl-2-{[formyl(hydroxy)amino]
methyl}propanoyl)-N-[({2-[4-(formylamino)phenyl]
ethyl}amino)carbonyl]-L-prolinamide.

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl, hexyl and the like.

As used herein, the term "alkenyl" refers to a straight or branched chain hydrocarbon radical having at least one carbon-carbon double bond. Examples of "alkenyl" as used herein include, but are not limited to, ethenyl and propenyl.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein the term "amino acid side chain" refers to the R-group or functional group of an amino acid as depicted in formula (II) below.

(II)

For example, the "amino acid side chain" or R-group is $CH_3$ for alanine, $(CH_3)_2CH-$ for valine, $(CH_3)_2CH-CH_2-$ for leucine, $(CH_3)_3C-$ for tert-leucine, phenyl-$CH_2-$ for phenylalanine, $CH_3-S-CH_2-CH_2-$ for methionine, etc.

As used herein, the term "aryl" refers to an aromatic hydrocarbon ring. Aryl groups are monocyclic ring systems or bicyclic ring systems. Monocyclic aryl ring refers to phenyl. Bicyclic aryl rings refer to napthyl and rings wherein phenyl is fused to a cycloalkyl or cycloalkenyl ring having 5, 6, or 7 member atoms. Aryl groups may be optionally substituted with one or more substituents as defined herein.

As used herein, the term "cycloalkyl" refers to a saturated hydrocarbon ring having the specified number of member atoms. Cycloalkyl groups are monocyclic ring systems. For example, $C_3$-$C_6$ cycloalkyl refers to a cycloalkyl group having from 3 to 6 member atoms. Cycloalkyl groups may be optionally substituted with one or more substituents as defined herein. Cycloalkyl includes cyclopropyl, cyclobutyl, cyclopentyl, and cyclohexyl.

As used herein, the term "halogen" refers to fluorine (F), chlorine (Cl), bromine (Br), or iodine (I), and "halo" refers to the halogen radicals fluoro, chloro, bromo and iodo.

As used herein, the term "heteroaryl" refers to an aromatic ring containing from 1 to 4 heteroatoms as member atoms in the ring. Heteroaryl groups containing more than one heteroatom may contain different heteroatoms. Heteroaryl groups may be optionally substituted with one or more substituents as defined herein. Heteroaryl groups are monocyclic ring systems or are fused, spiro, or bridged bicyclic ring systems. Monocyclic heteroaryl rings have 5 or 6 member atoms. Bicyclic heteroaryl rings have from 7 to 11 member atoms. Bicyclic heteroaryl rings include those rings wherein phenyl and a monocyclic heterocycloalkyl ring are attached forming a fused, spiro, or bridged bicyclic ring system, and those rings wherein a monocyclic heteroaryl ring and a monocyclic cycloalkyl, cycloalkenyl, heterocycloalkyl, or heteroaryl ring are attached forming a fused, spiro, or bridged bicyclic ring system. Heteroaryl includes pyrrolyl, pyrazolyl, imidazolyl, oxazolyl, isoxazolyl, thiazolyl, isothiazolyl, furanyl, furazanyl, thienyl, triazolyl, pyridinyl, pyrimidinyl, pyridazinyl, pyrazinyl, triazinyl, tetrazinyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, benzopyranyl, benzoxazolyl, benzofuranyl, isobenzofuranyl, benzothiazolyl, benzothienyl, furopyridinyl, and napthyridinyl.

As used herein, the term "heteroatom" refers to a nitrogen, sulphur, or oxygen atom.

As used herein, the term "heterocycloalkyl" refers to a saturated or unsaturated ring containing from 1 to 4 heteroatoms as member atoms in the ring. However, heterocycloalkyl rings are not aromatic. Heterocycloalkyl groups containing more than one heteroatom may contain different heteroatoms. Heterocycloalkyl groups may be optionally substituted with one or more substituents as defined herein. Heterocycloalkyl groups are monocyclic ring systems having from 4 to 7 member atoms. In certain embodiments, heterocycloalkyl is saturated. In other embodiments, heterocycloalkyl is unsaturated but not aromatic. Heterocycloalkyl includes pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiomorpholinyl, 1,3-dioxolanyl, 1,3-dioxanyl, 1,4-dioxanyl, 1,3-oxathiolanyl, 1,3-oxathianyl, 1,3-dithianyl, and azetidinyl.

As used herein, the term "member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

As used herein, the term "optionally substituted" indicates that a group, such as alkyl, alkenyl, alkynyl, aryl, cycloalkyl, cycloalkenyl, heterocycloalkyl, or heteroaryl, may be unsubstituted or substituted with one or more substituents as defined herein. "Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

The skilled artisan will appreciate that pharmaceutically-acceptable salts of the compounds according to Formula I may be prepared. Indeed, in certain embodiments of the invention, pharmaceutically-acceptable salts of the compounds according to formula I may be preferred over the respective free base or free acid because such salts impart greater stability or solubility to the molecule thereby facilitating formulation into a dosage form. Accordingly, the invention is further directed to pharmaceutically-acceptable salts of the compounds according to Formula I.

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

In certain embodiments, compounds according to Formula I may contain an acidic functional group. Suitable pharmaceutically-acceptable salts include salts of such acidic functional groups. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formula I may contain a basic functional group and are therefore capable of forming pharmaceutically-acceptable acid addition salts by treatment with a suitable acid. Suitable acids include pharmaceutically-acceptable inorganic acids and pharmaceutically-acceptable organic acids. Representative pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycolate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

As used herein, the term "compounds of the invention" means both the compounds according to Formula I and the pharmaceutically-acceptable salts thereof.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as acetone, ethanol, n-propanol, isopropanol, n-butanol, tert-butanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures).

These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

General Synthetic Sequence

The compounds and processes of the present invention will be better understood in connection with the following synthetic schemes, which are merely illustrative of the methods by which the compounds of the invention may be prepared and are not intended to limit the scope of the invention as defined in the appended claims.

The compounds of the invention can be prepared as depicted in the Scheme 1 below, using as starting materials compounds previously described in WO 2003101442 and WO 2002070541. In the preferred method, carboxylic acid (1) is subjected to an EDCI coupling with L-prolinamide to provide the amide (2), a versatile intermediate for the preparation of the compounds of the invention. The primary amide (2) is reacted with 2-2.2 equivalents of a base and an activated carboxylic acid or derivative thereof, such as (but not limited to) an acid chloride to afford imide derivatives (3). A number of bases may be used such as those derived from amines (such as but not limited to lithiumhexamethyldisilazide, sodium hexamethyldisilazide, potassium hexamethyldisilazide, lithium diisopropyl amide, lithium diethylamide), alkali metal alkoxide bases, and alkali metal hydride bases. Compounds such as (3) are hydrogenated in the presence of a catalyst to provide compound (4). The preferred catalyst for the hydrogenation is palladium on barium sulfate (unreduced), previously described Nikam et al. (Tetrahedron Letters 1995, 36, 197-200) for hydroxamic acids, which minimizes byproducts resulting from reductive cleavage of the N—O bond.

Alternatively, the intermediate (2) can be reacted with a cloroformate, imidazolyl carbonyl or similar species in the presence of a base to afford the acylcarbamates compounds (5), which can then be converted by the hydrogenation method described above to compound (6).

In addition, the intermediate (2) may be reacted with an isocyanate or carbamoyl chloride (or similar derivative) and base to afford compound (7), which can be hydrogenated as described above to provide acylurea compound (8). When an isocycante is used in the conversion of (2) to (7), a base may not be necessary for the reaction to proceed.

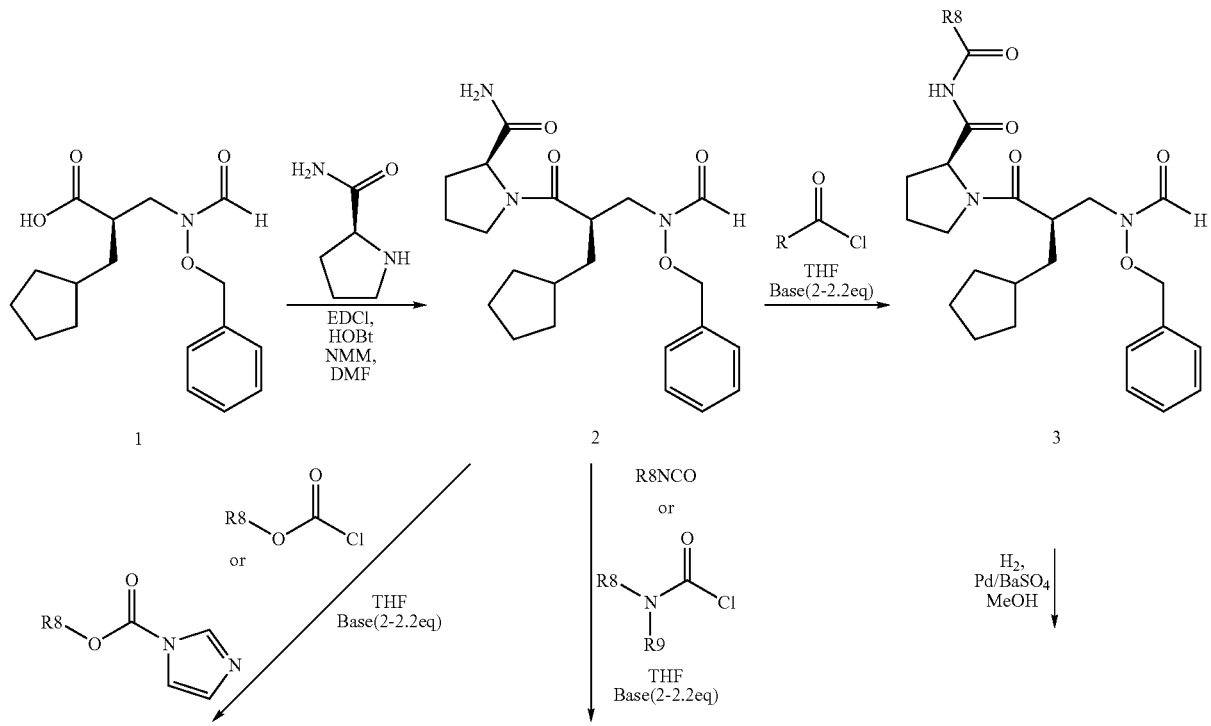

Scheme 1

15

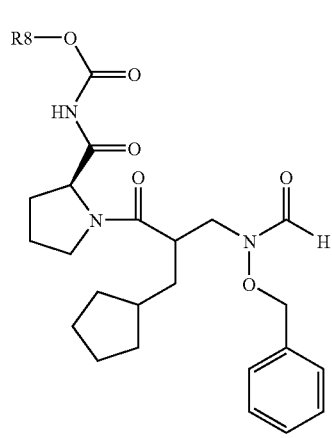

5

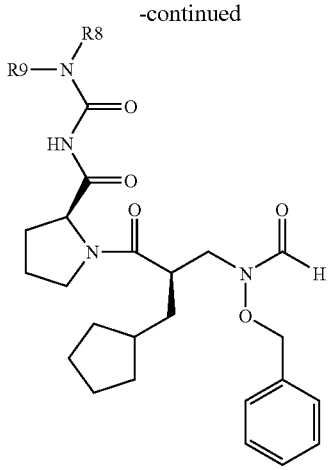

7

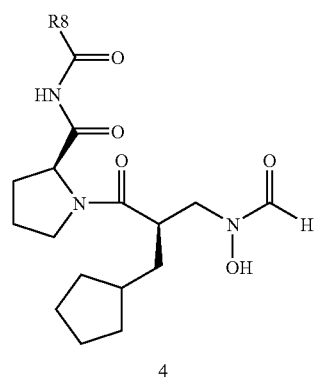

4

-continued

16

H₂,
Pd/BaSO₄
MeOH

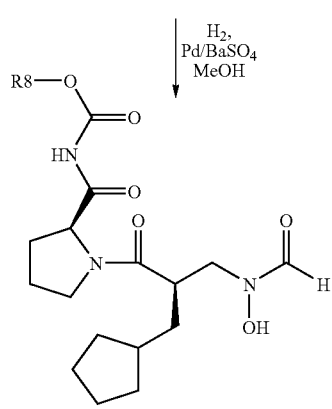

6

H₂,
Pd/BaSO₄
MeOH

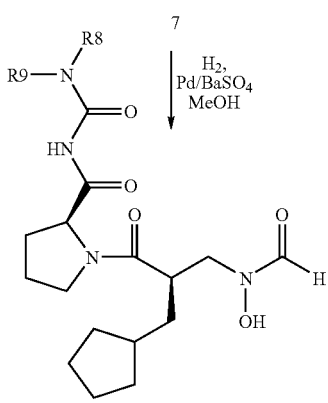

8

An alternative method was invented for preparing acylurea compounds (8). The method is illustrated in Scheme 2. Intermediate (2) is hydrogenated over a palladium catalyst in methanol to provide compound (9), which is then protected as its tert-butyldimethylsilyl ether (TBDMS), compound (10). Compound (10) is reacted with phenylchloroformate in the presence of two equivalents of base, followed by aqueous acid quenching and workup to remove the TBDMS group.

This provides compound (11), which is a useful intermediate for the preparation of acylureas. For example, compound (11) can be reacted with an amine in various solvents (such as, but not limited to methanol, ethanol, acetonitrile, dichloromethane, ethyl acetate, N,N-dimethylformamide) to afford compound (8). The method allows for direct isolation of the product from the reaction mixture, without the need for a workup procedure.

Scheme 2

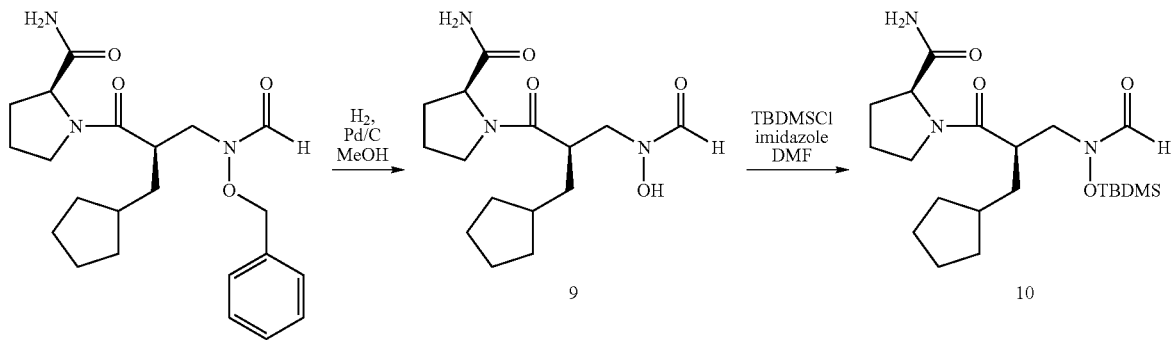

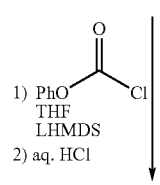

1) PhO—C(O)—Cl
   THF
   LHMDS
2) aq. HCl

-continued

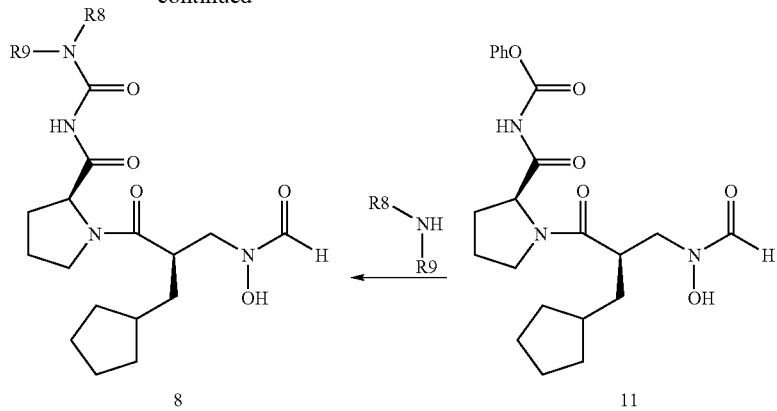

The above methods described in Schemes 1 and 2 can be used to prepare compounds of the invention that contain varying R3 and R4 groups. For example, substitution of tert-L-leucine, or 3,3-dimethyl-L-prolinamide for L-prolinamide in the preparation of (2) from (1) will provide the intermediates (12) and (13) respectively, which can be converted to compounds of the invention by the methods detailed in Schemes 1 and 2.

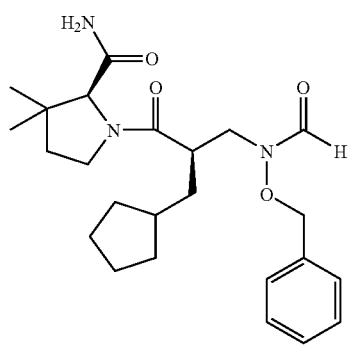

12

The process for preparing 3,3-dimethyl-L-prolinamide is shown in Scheme 3. Commercially available 3-methyl-2-pyrrolidinone (14) can be protected as a tert-butyldimethylsilyl (TBDMS) ether (15), which is alkylated with methyl iodide to provide (16). The nitrogen protecting group is removed to provide compound (17) and replaced with a benzyloxycarbonyl group to give compound (18). Reduction of the amide carbonyl affords compound (19), which is treated with acidic methanol to prepare (20). Compound (20) can be treated with trimethylsilyl cyanide and borontrifluoride etherate to prepare compound (21), which is converted to compound (22) by treatment with hydrogen peroxide in dimethyl sulfoxide with catalytic potassium carbonate, the procedure of Katritzky et al. (Synthesis, 1989, 12, 949-950). The racemate (22) is then resolved using preparative chiral HPLC to give enantiomerically pure compounds (23) and (24), which and are then hydrogenated over a palladium catalyst in methanol to afford 3,3-dimethyl-L-prolinamide (25) and 3,3-dimethyl-D-prolinamide (26), respectively.

Scheme 3

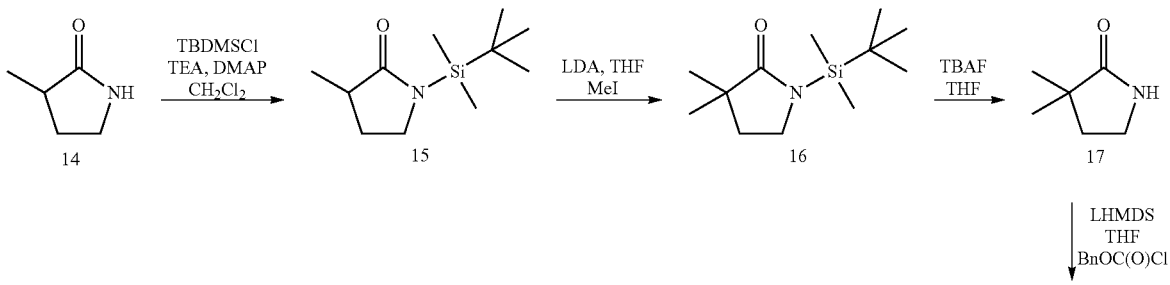

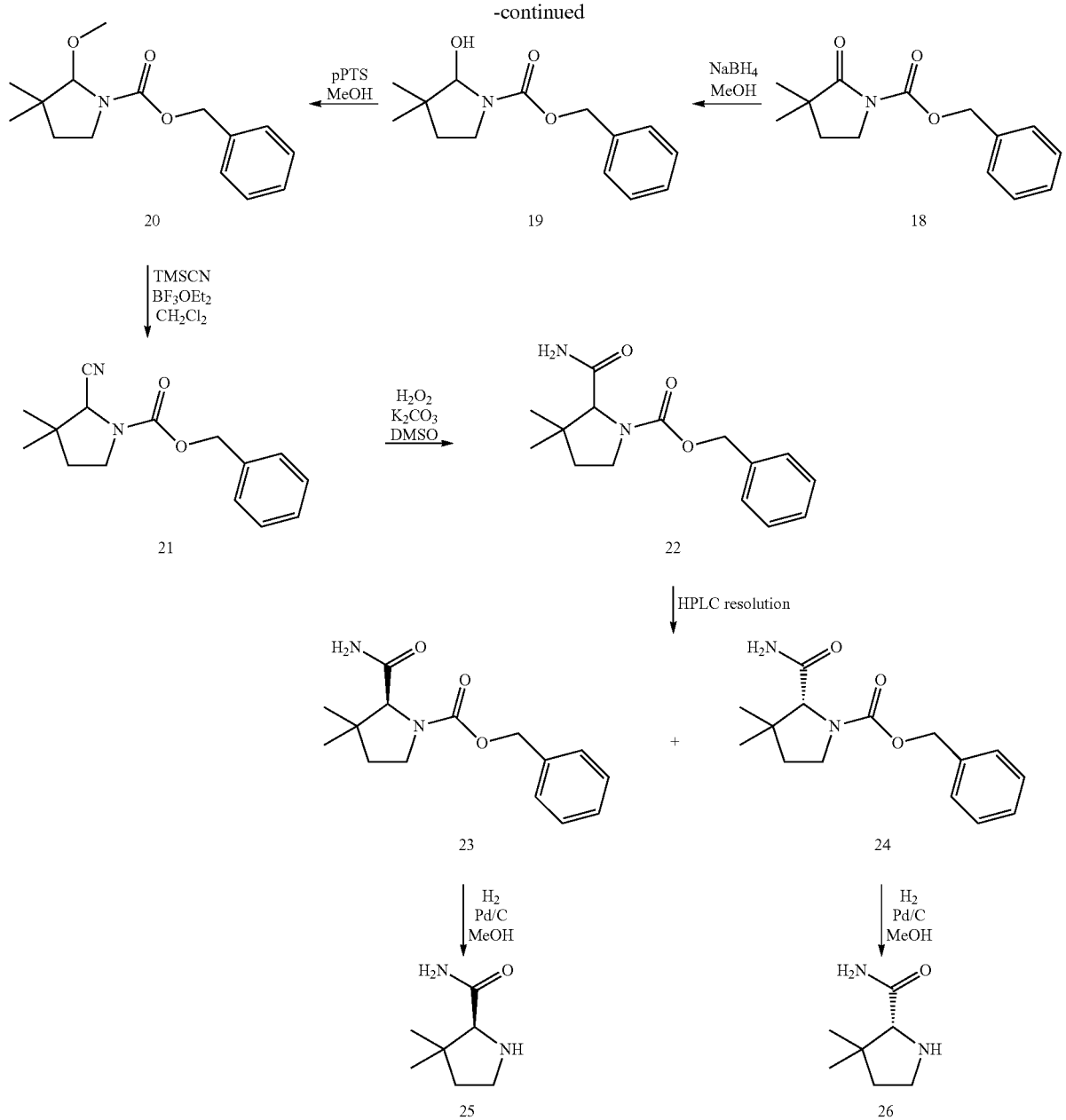
Experimental Procedures
1-((2R)-3-cyclopentyl-2-{[formyl(hydroxy)amino]methyl}propanoyl)-N [(phenyloxy)carbonyl]-L-prolinamide
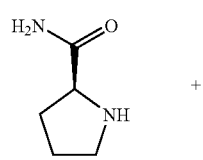
+
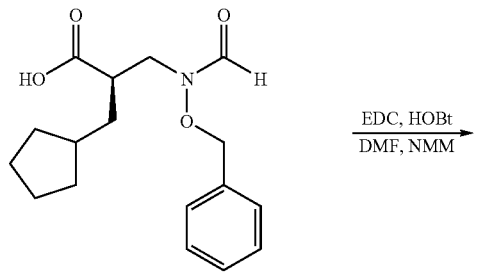
-continued

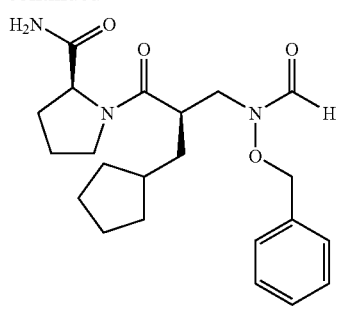

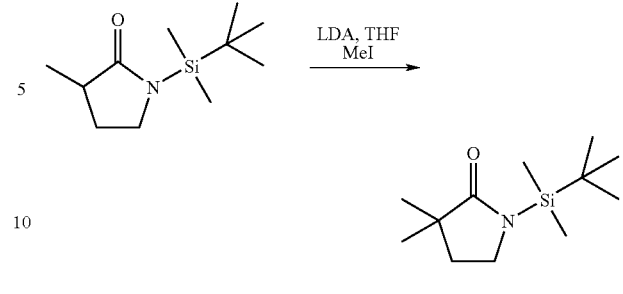

(2R)-3-cyclopentyl-2-({formyl[(phenylmethyl)oxy]amino}methyl)propanoic acid (WO 2003101442, 38.2 g, 0.125 mol), L-prolinamide (14.3 g, 0.125 mol,) N-methyl morpholine (34.4 mL, 0.313 mol,) and HOBt (18.65 g, 0.138 mol) were dissolved in DMF (400 mL) with stirring. EDC (26.46 g, 0.138 mol) was added portionwise and the solution was stirred at room temperature for 3 hours. The majority of the DMF was removed in vacuo and the residue was diluted with ethyl acetate (1 L.) This solution was washed with cold 0.5M HCl solution (200 mL), twice with water (200 mL), saturated aqueous $NaHCO_3$ solution, brine, and then dried over $MgSO_4$. After filtering and evaporating, the crude material was dissolved in hot ethyl acetate (~150 mL) with stirring. While keeping the solution hot, hexanes (~150 mL) was added until the solution was cloudy. Cooling slowly to room temperature while stirring gave a thick slurry. The solid was filtered off and washed with 1:1 ethyl acetate:hexanes, followed by a wash with hexanes. After drying, the product 1-[(2R)-3-cyclopentyl-2-({formyl[(phenylmethyl)oxy]amino}methyl)propanoyl]-L-prolinamide was obtained as a white solid (34.4 g, 69% yield). LC/MS m/z 402 (MH+)

1-[(2R)-3-cyclopentyl-2-({formyl[(phenylmethyl)oxy]amino}methyl)propanoyl]-3,3-dimethyl-L-prolinamide

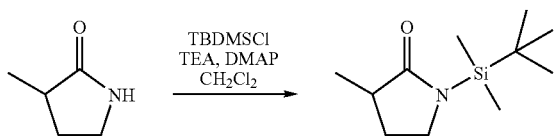

In an oven-dried 500 ml flask under argon was dissolved 3-methyl-2-pyrrolidinone (0.186 mol, 18.4 g) in 200 ml methylene chloride. To this solution was added Triethylamine (0.223 mol, 22.6 g), Dimethylaminopyridine (0.019 mol, 2.27 g), and t-Butyldimethylsilyl chloride (0.204 mol, 30.8 g). This mixture was stirred for 18 hrs at 20° C. after which time it was poured into 500 ml water, the organic layer separated, washed with water (2×100 ml), brine (100 ml), dried with $MgSO_4$ and concentrated. Resulting crude oil was purified on 400 g silica (EtOAc/Hexanes) yielding 35.0 g (88%) of 1-[(1,1-dimethylethyl)(dimethyl)silyl]-3-methyl-2-pyrrolidinone a clear oil. LCMS (ESI$^+$)=214 m/z (MH$^+$). $^1$H NMR (400 MHz, CDCl$_3$) δ 3.40-3.25 (m, 2H), 2.50-2.40 (m, 1H), 2.30-2.20 (m, 1H), 1.70-1.60 (m, 1H), 1.20-1.18 (d, 3H, J=7.06 Hz), 0.95 (s, 9H), 0.29-0.27 (d, 6H, J=6.70 Hz).

In an oven-dried 1000 ml 3-neck flask fitted with septa and thermometer was charged with diisopropylamine (0.177 mol, 17.9 g) and 300 ml THF. The solution was cooled to 0° C. and n-Butyl lithium (0.193 mol, 77.1 ml of a 2.5M solution in hexanes) was added with stirring over 5 min. After 30 min, the reaction was cooled to −78° C. and a solution of 1-[(1,1-dimethylethyl)(dimethyl)silyl]-3-methyl-2-pyrrolidinone (0.161 mol, 34.3 g) in 80 ml THF was added dropwise keeping reaction temperature below −60° C. Once complete, the reaction was warmed to 20° C. After 1 hr, the reaction was cooled to −78° C. and a solution of Iodomethane (0.177 mol, 25.1 g) in 10 ml of THF was added dropwise over 10 min. The reaction was warmed to 20° C. and stirred for 16 hr, after which time 300 ml saturated $NH_4Cl$ was added. The aqueous phase was extracted with ethylacetate (2×150 ml), the organics were combined, dried over $MgSO_4$, filtered and concentrated. The resulting crude oil was purified on 400 g silica (ethyl acetate/hexanes) to yield 29.9 g (82%) of 1-[(1,1-dimethylethyl)(dimethyl)silyl]-3,3-dimethyl-2-pyrrolidinone as a light yellow oil. LCMS (ESI$^+$)=228 m/z (M$^+$). $^1$H NMR (400 MHz CDCl$_3$) δ 3.31-3.27 (t, 2H, J=6.68 Hz), 1.90-1.87 (t, 2H, J=6.79 Hz), 1.15 (s, 6H), 0.96 (s, 9H), 0.28 (s, 6H).

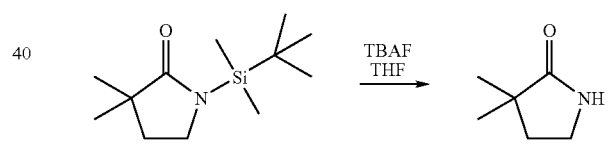

In an oven-dried 1000 ml flask under argon is dissolved 1-[(1,1-dimethylethyl)(dimethyl)silyl]-3,3-dimethyl-2-pyrrolidinone (0.129 mol, 29.4 g) in 250 ml THF. The resulting solution was cooled to 5° C., and tetrabutylammonium fluoride (0.194 mol, 194 ml of a 1M solution in THF) was added over 30 min, with no appreciable exotherm. The reaction was warmed to 20° C. and stirred 2 hr after which time it was concentrated. The resulting crude oil was purified on 400 g silica (dichloromethane/methanol) yielding 8.13 g (56%) of 3,3-dimethyl-2-pyrrolidinone as a white solid. LCMS (ESI$^+$)=114 m/z (M$^+$). $^1$H NMR (400 MHz, CDCl$_3$) δ 6.50 (br.s 1H), 3.33-3.30 (m, 2H), 1.99-1.95 (t, 2H, J=6.83 Hz), 1.18 (s, 6H). $^{13}$C NMR (CDCl$_3$) δ 183.87, 39.61, 38.75, 36.44, 24.27.

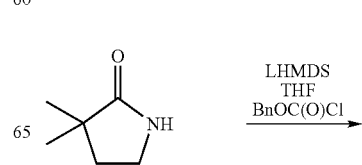

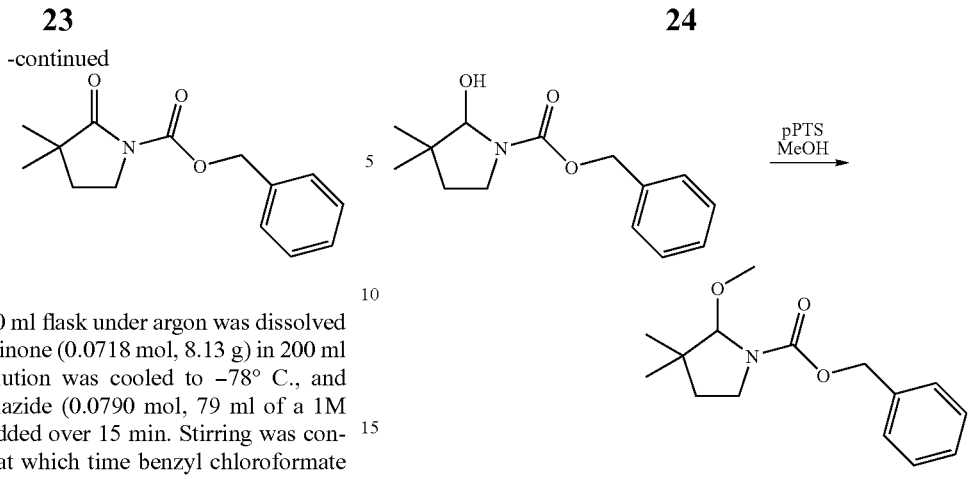

In an oven-dried 1000 ml flask under argon was dissolved 3,3-dimethyl-2-pyrrolidinone (0.0718 mol, 8.13 g) in 200 ml THF. The resulting solution was cooled to −78° C., and lithium hexamethyldisilazide (0.0790 mol, 79 ml of a 1M solution in THF) was added over 15 min. Stirring was continued for 30 minutes, at which time benzyl chloroformate (0.0790 mol, 13.5 g) was added and the reaction was allowed to warm to room temperature and stir for 16 hr. The mixture was concentrated to 1/3 total volume and diluted with 500 ml ethyl acetate and washed with 1M HCl (2×200 ml), water (1×200 ml), and brine (1×100 ml). The organic phase was dried over MgSO$_4$, filtered and concentrated. Purification of the crude residue on 120 g silica (ethyl acetate/hexanes) yielded 12.3 g (69%) of phenylmethyl 3,3-dimethyl-2-oxo-1-pyrrolidinecarboxylate as a light yellow oil. LCMS (ESI$^+$)=248 m/z (M$^+$), 270 m/z (MNa$^+$). $^1$H NMR (400 MHz, CDCl$_3$) δ 7.48-7.46 (m, 2H), 7.39-7.36 (m, 3H), 5.31 (s, 2H), 3.77-3.73 (t, 2H, J=6.96 Hz), 1.91-1.88 (t, 2H, J=7.08 Hz), 1.23 (s, 6H). $^{13}$C NMR (CDCl$_3$) δ 178.83, 151.86, 135.35, 128.60, 128.34, 128.10, 68.00, 42.79, 42.16, 32.95, 24.28.

In a 500 ml flask was dissolved phenylmethyl 2-hydroxy-3,3-dimethyl-1-pyrrolidinecarboxylate (0.0475 mol, 11.8 g) in 100 ml methanol. Catalytic Pyridinium p-toluenesulfonate (0.00475 mol, 1.19 g) was added and the reaction was stirred at 20° C. for 45 min. The reaction was quenched with triethylamine (3 ml) and concentrated. The resulting crude oil was purified on 120 g silica (chloroform/ethyl acetate) yielding 11.2 g (90%) of phenylmethyl 3,3-dimethyl-2-(methyloxy)-1-pyrrolidinecarboxylate as a clear oil. LCMS (ESI$^+$)=286 m/z (MNa$^+$). $^1$H NMR (400 MHz, CDCl$_3$)— rotamers δ 7.39-7.32 (m, 5H), 5.24-5.13 (m, 2H), 4.68 and 4.57 (s, 1H), 3.52-3.46 (m, 4H), 3.31 (s, 2H), 1.97-1.90 (m, 1H), 1.58-1.54 (m, 1H), 1.10 (s, 3H), 0.9 (s, 3H).

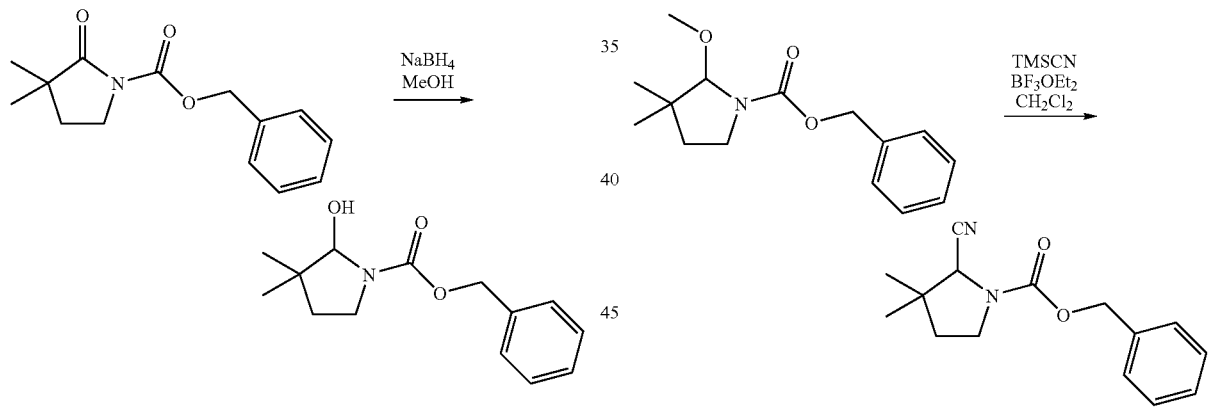

In a 500 ml flask was dissolved phenylmethyl 3,3-dimethyl-2-oxo-1-pyrrolidinecarboxylate (0.0494 mol, 12.2 g) in 100 ml methanol. The mixture was cooled to −10° C. and sodium borohydride (0.247 mol, 9.35 g) was added slowly in portions with stirring, maintaining an internal temperature below −5° C. After the addition TLC (90:10 CHCl$_3$:EtOAc) confirmed reaction was complete. The mixture was poured onto 500 ml saturated aqueous NH$_4$Cl with crushed ice and stirred 16 hours, after which time the aqueous phase was extracted with Et$_2$O (2×200 ml). The organics were dried over MgSO$_4$, filtered and concentrated yielding 11.8 g (96%) of phenylmethyl 2-hydroxy-3,3-dimethyl-1-pyrrolidinecarboxylate as a clear oil which was used without further purification. LCMS (ESI$^+$)=232 m/z ([M-OH]$^+$). $^1$H NMR (400 MHz, CDCl$_3$)— rotamers δ 7.39-7.33 (m, 5H), 5.25-5.14 (m, 2H), 4.99 and 4.92 (s, 1H), 3.61-3.38 (m, 2H), 1.97-1.91 (m, 1H), 1.62-1.56 (m, 1H), 1.12 (s, 3H), 1.02 (s, 3H).

In a 500 ml flask was dissolved phenylmethyl 3,3-dimethyl-2-(methyloxy)-1-pyrrolidinecarboxylate (0.0426 mol, 11.2 g) in 200 ml methylene chloride under argon. After the solution was cooled to −78° C., trimethylsilyl cyanide (0.0640 mol, 6.32 g) was added followed by boron triflouride etherate (0.0640 mol, 9.09 g). After 1 hr of stirring, the reaction was quenched with saturated aqueous sodium bicarbonate and allowed to warm to 20° C. After 2 hr of vigorous stirring, the aqueous phase was separated and extracted with methylene chloride (2×100 ml). All organics were combined, dried over MgSO$_4$, filtered and concentrated yielding 10.8 g (98%) of phenylmethyl 2-cyano-3,3-dimethyl-1-pyrrolidinecarboxylate as a clear oil which was used without further purification. LCMS (ESI$^+$)=259 m/z (MH$^+$). $^1$H NMR (400 MHz, CDCl$_3$)— rotamers δ 7.44-7.35 (m, 5H), 5.21 and 5.20 (s, 2H), 4.26 and 4.17 (s, 1H), 3.64-3.51 (m, 2H), 2.01-1.95 (m, 1H), 1.80-1.74 (m, 1H), 1.36 (s, 3H), 1.16 (s, 3H).

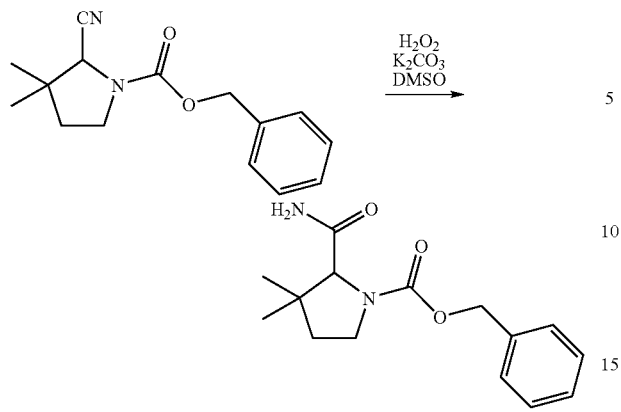

In a 200 ml flask was dissolved phenylmethyl 2-cyano-3,3-dimethyl-1-pyrrolidinecarboxylate (0.0414 mol, 10.7 g) in 30 ml dimethylsulfoxide. Potassium carbonate (0.0155 mol, 2.14 g) was added with stirring and the reaction was cooled to 10° C. With internal temperature monitoring, an aqueous solution of 30% Hydrogen peroxide (5.5 ml) was added slowly to minimize any exotherm. After the reaction ceases to gas evolution, it was allowed to warm to 20° C. and stirred for 2 hr. The reaction was diluted with 300 ml water and extracted with methylene chloride (3×100 ml). The organics were dried over MgSO$_4$, filtered and concentrated yielding 12.2 g (quantitative, minimal DMSO contaminant) of a clear oil. LCMS (ESI$^+$)=277 m/z (MH$^+$). $^1$H NMR (400 MHz, CDCl$_3$)—, rotamers δ 7.40-7.28 (m, 5H), 6.12- and 5.85 (bs, 1H), 5.77 (bs, 1H), 5.18-5.09 (m, 2H), 3.86-3.83 (m, 1H), 3.67-3.50 (m, 2H), 2.06-1.88 (m, 1H), 1.62-1.59 (m, 1H), 1.16-1.12 (m, 6H).

The racemic material was resolved by preparative chiral HPLC (Chiralpak AD 20μ; 77×240 mm, 3×4 g injection, 95:5 acetonitrile:isopropanol, 300 mL/min, uv detection at 220 nM) yielding 5.5 g of optically pure (99% ee) phenylmethyl (2R)-2-(aminocarbonyl)-3,3-dimethyl-1-pyrrolidinecarboxylate (retention time=2.8 min) as a clear colorless oil, and 5.3 g of phenylmethyl (2S)-2-(aminocarbonyl)-3,3-dimethyl-1-pyrrolidinecarboxylate (retention time=5.8 minutes, [α]$_D$ +28.8° (c=1.0, methanol)) as a colorless oil. Enantiomeric purity was assessed by analytical chiral HPLC (Chiralpak AD-H, 4.6×150 mm) under the following conditions: 95:5 acetoniltrile:isopropanol, 1.0 mL/min, uv detection at 220 nM). The retention times (minutes) are (R)-enantiomer=2.6, (S)— enantiomer=4.9.

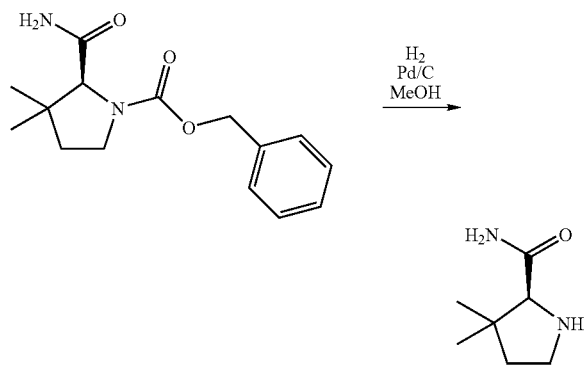

In a 200 ml flask was dissolved phenylmethyl (2S)-2-(aminocarbonyl)-3,3-dimethyl-1-pyrrolidinecarboxylate (0.0192 mol, 5.3 g) in 80 ml methanol at 20° C. 10% Pd/C (Degussa type, 0.53 g) was added and the mixture was stirred for 5 hr under atmospheric H$_2$. The catalyst was filtered and the reaction was concentrated yielding 2.8 g (quantitative) of 3,3-dimethyl-L-prolinamide as a white solid. LCMS (ESI$^+$)=143 m/z (MH$^+$). $^1$H NMR (400 MHz, CDCl$_3$)— rotamers δ 7.20 (bs, 1H), 6.20 (bs, 1H), 3.32 (s, 1H), 3.05-3.01 (m, 2H), 2.50 (bs, 1H), 1.67-1.62 (m, 2H), 1.23 (s, 3H), 0.97 (s, 3H). [α]$_D$ +1.2° (c=0.5, methanol)

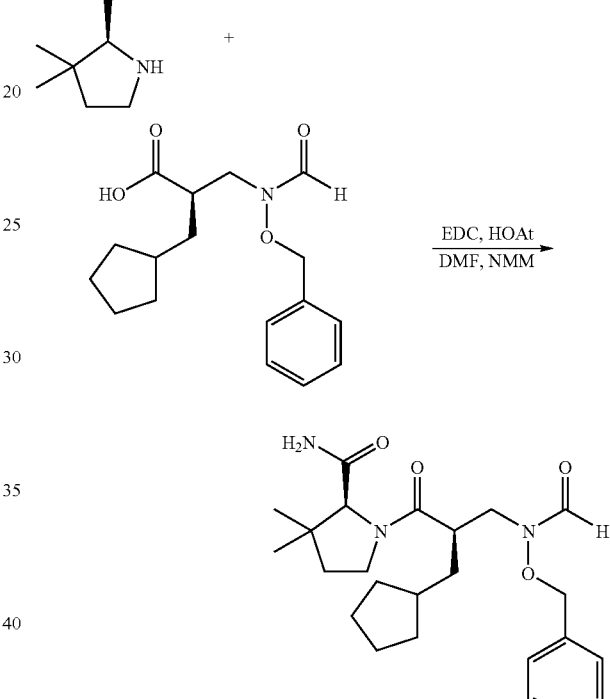

In an oven-dried 100 ml flask was dissolved 3,3-dimethyl-L-prolinamide (0.0174 mol, 2.46 g), (2R)-3-cyclopentyl-2-({formyl[(phenylmethyl)oxy]amino}methyl)propanoic acid (WO 2003101442, 0.0174 mol, 5.30 g), and 1-hydroxy-7-azabenzotriazole (0.0191 mol, 2.60 g) in 25 ml DMF with stirring under argon. To this solution was added N-methylmorpholine (0.0522 mol, 5.28 g) followed by 1-(3-dimethylaminopropyl)-3-ethylcarbodiimide hydrochloride (0.0191 mol, 3.67 g). The reaction was stirred at 20° C. for 16 hr after which time it was diluted with 300 ml water and extracted with ethylacetate (3×100 ml). The combined organics were washed with 100 ml 1M HCl followed by brine. The organics were dried over MgSO$_4$, filtered and concentrated to a yellow oil and purified on 90 g silica (chloroform/methanol/water), yielding 4.72 g (63%) of 1-[(2R)-3-cyclopentyl-2-({formyl[(phenylmethyl)oxy]amino}methyl)propanoyl]-3,3-dimethyl-L-prolinamide as a white solid. LCMS (ESI$^+$)=430 m/z (MH$^+$). $^1$H NMR (400 MHz, CDCl$_3$)— rotamers δ 8.20-7.86 (m, 1H), 7.49-7.30 (m, 5H), 6.01-5.50 (m, 2H), 5.05-4.70 (m, 2H), 3.89-3.56 (m, 4H), 3.14-2.90 (m, 2H), 2.16-2.05 (m, 1H), 1.89-1.40 (m, 10H), 1.13-1.06 (m, 6H), 1.02-0.84 (m, 2H).

1-((2R)-3-cyclopentyl-2-{[formyl(hydroxy)amino]methyl}propanoyl)-N-[(phenyloxy)carbonyl]-L-prolinamide

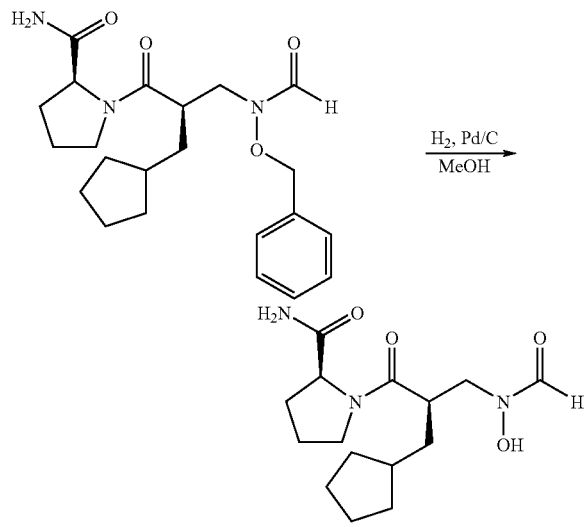

1-[(2R)-3-cyclopentyl-2-({formyl[(phenylmethyl)oxy]amino}methyl)propanoyl]-L-prolinamide (24 g, 0.060 mol) was dissolved in MeOH (500 mL) and degassed. Catalyst (10% Pd/C, Degussa type, wet, 2.4 g) was added and the mixture was stirred under a hydrogen balloon for 3 hours. After degassing, the suspension was filtered through Celite, washing with methanol, and the filtrate was concentrated. The resulting foam was dissolved in ethyl acetate (50 mL) and diluted with toluene (~500 mL.) This solution was then concentrated to a slurry (~100 mL) and diluted with hexanes (200 mL.) Filtration, washing with hexanes and drying afforded the product 1-((2R)-3-cyclopentyl-2-{[formyl(hydroxy)amino]methyl}propanoyl)-L-prolinamide (21 g, 113% yield). The excess yield is due to residual toluene. LC/MS m/z 312 (MH+)

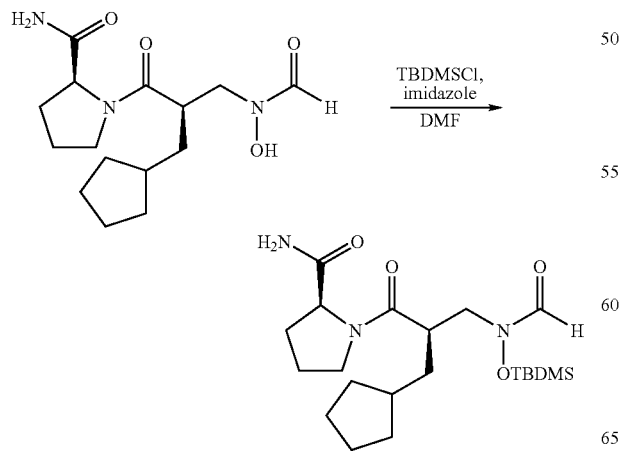

1-((2R)-3-cyclopentyl-2-{[formyl(hydroxy)amino]methyl}propanoyl)-L-prolinamide (18 g, 0.058 mol) was dissolved in DMF (150 mL) and imidazole (11.8 g, 0.176 mol) was added. The solution was cooled to 0 degrees C. and TBSCI (13.1 g, 0.087 mol) was added portionwise. The reaction mixture was stirred at 0 degrees C. for 1 hour, then allowed to warm to room temperature and diluted with ice water (400 mL.) The resulting mixture was extracted with ethyl acetate (3×200 mL) and the combined organic extracts were washed with water (2×) and brine, and dried over MgSO4. Evaporation of this solution gave an oily white mass which was triturated and slurried in ether (100 mL) for 1 hour to give a fine suspension. Hexanes (50 mL) were added and the suspension was filtered and washed with 2:1 ether:hexanes, followed by hexanes alone. After drying, 1-((2R)-3-cyclopentyl-2-{[{[(1,1-dimethylethyl)(dimethyl)silyl]oxy}(formyl)amino]methyl}propanoyl)-L-prolinamide was obtained as a fluffy white solid (71% yield, 17.4 g). LC/MS m/z 312 ((MH-TBDMS)H+).

$^1$H NMR (400 MHz, d$_6$-DMSO): δ 7.81 (bs, 1H); 7.27 (bs, 1H); 6.83 (bs, 1H); 4.17 (m, 1H); 3.59-3.70 (m, 2H); 3.53 (m, 1H); 3.32 (m, 1H); 3.04 (bs, 1H); 1.85-2.05 (m, 2H); 1.64-1.85 (m, 5H); 1.35-1.64 (m, 5H); 1.22 (m, 1H); 1.06 (m, 2H); 0.93 (s, 9H); 0.15 (s, 6H)

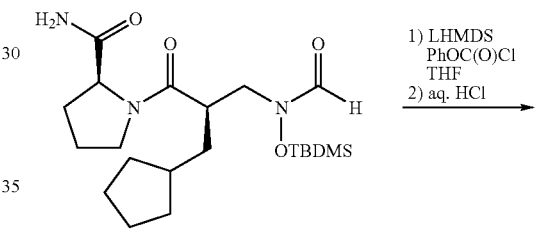

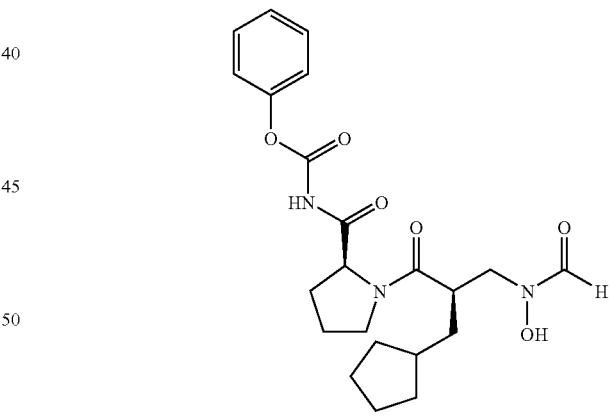

1-((2R)-3-cyclopentyl-2-{[{[(1,1-dimethylethyl)(dimethyl)silyl]oxy}(formyl)amino]methyl}propanoyl)-L-prolinamide (4.25 g, 0.010 mol) was dissolved in THF (40 mL) and cooled to −78 degrees C. with stirring. Phenylchloroformate (1.38 mL, 0.011 mol) was added, followed by dropwise addition of 1M LHMDS in THF (22 mL, 0.022 mol). After the addition the reaction was stirred at −78 degrees C. for 2 hours, then quenched with 2N HCl (20 mL) and allowed to warm to room temperature. Brine (20 mL) was added and the mixture was extracted with ethyl acetate (3×75 mL). The combined extracts were washed with water, brine, and dried over $Na_2SO_4$. Filtration and evaporation provided a crude oil that was treated with ether (50 mL) and then hexanes (50 mL) to precipitate the product as a thick gum. After agitating by stirring 2 to 3 hours the gum became a free-flowing solid. The product was filtered and washed with 1:1 ether:hexanes, hexanes, then dried to afford 1-((2R)-3-cyclopentyl-2-{[formyl (hydroxy)amino]methyl}propanoyl)-N-[(phenyloxy)carbonyl]-L-prolinamide as a white solid (3.93 g, 91% yield). LC/MS m/z 432 (MH+)

General Procedures to Prepare Compounds of the Invention:

The following procedure is general and can be applied to primary amides to prepare imides (4). Substitution of the acid chloride with a chloroformate or alkyl 1H-imidazole-1-carboxylate provides acylcabamates (6). Substitution of the acid chloride with a carbamoyl chloride provides the ureas (8), when both R8 and R9 are not hydrogen.

1-[3-cyclopentyl-2-({formyl[(phenylmethyl)oxy] amino}methyl)propanoyl]-L-prolinamide (0.5 mmol, 200 mg) was dissolved in 2 mL of THF. The solution was cooled to −78° C. and 4-fluorobenzoyl chloride (0.55 mmol, 65 uL) was added. LiHMDS (1M in THF, 1.1 mmol, 1 mL) was added dropwise. The solution was stirred 30 minutes before being quenched with saturated aqueous ammonium chloride solution. The resulting mixture was extracted with ethyl acetate. The organic layer was washed with brine, dried over $MgSO_4$, filtered, concentrated and chromatographed in 0.5-8% $MeOH/CHCl_3$. The compound was obtained cleanly in 69% yield (180 mg.)

1-[3-cyclopentyl-2-({formyl[(phenylmethyl)oxy] amino}methyl)propanoyl]-N-[(4-fluorophenyl)carbonyl]-L-prolinamide (0.34 mmol, 180 mg) was dissolved in MeOH (3 mL) and the solution was degassed. 10% Pd/C or $Pd/BaSO_4$ (36 mg) was added and the suspension was charged with $H_2$ via balloon. The reaction was stirred under $H_2$ atmosphere for 1 hour, then filtered and concentrated to provide 1-((2R)-3-cyclopentyl-2-{[formyl(hydroxy)amino] methyl}propanoyl)-N-[(4-fluorophenyl)carbonyl]-L-prolinamide (Example 1) in quantitative yield.

The following two general procedures illustrate the preparation of ureas (8) when R8 or R9 is hydrogen.

Using an Isocyanate:

A stirred solution of 1-[(2R)-3-cyclopentyl-2-({formyl [(phenylmethyl)oxy]amino}methyl)propanoyl]-L-prolinamide (401 mg, 1 mmol) and isocyanate (1.5 mmol) in toluene (5 mL) was heated to 110 degrees C. in a sealed tube for 12 hours, or alternatively heated in a microwave reactor at 180 degrees C. for 2 hours. After cooling the product was purified by preparative reversed phase HPLC or silica gel chromatography.

Using an Amine:

To a stirred solution of 1-((2R)-3-cyclopentyl-2-{[formyl (hydroxy)amino]methyl}propanoyl)-N-[(phenyloxy)carbonyl]-L-prolinamide (108 mg, 0.25 mmol) in acetonitrile or alcohol (0.5 mL) was added the amine (0.25 mmol). When the reaction was complete the product was purified by preparative reversed phase HPLC or silica gel chromatography.

EXAMPLES

The following examples were generally prepared using the above methods:

Example 1

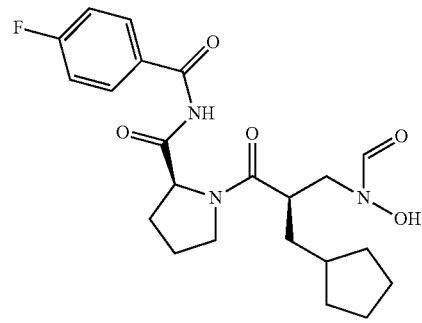

1-((2R)-3-cyclopentyl-2-{[formyl(hydroxy)amino] methyl}propanoyl)-N-[(4-fluorophenyl)carbonyl]-L-prolinamide LC-MS m/z 434 (MH+)

Example 2

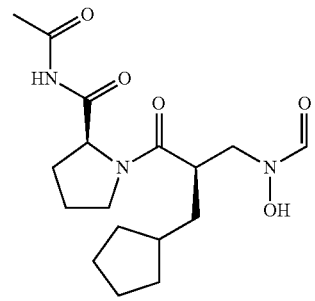

N-acetyl-1-((2R)-3-cyclopentyl-2-{[formyl(hydroxy) amino]methyl}propanoyl)-L-prolinamide LC-MS m/z 354 (MH+)

Example 3

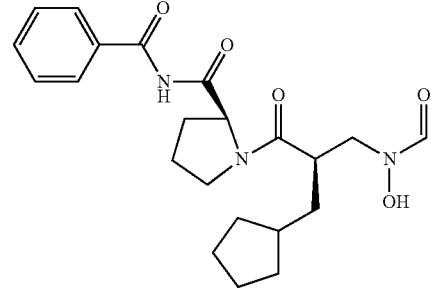

1-((2R)-3-cyclopentyl-2-{[formyl(hydroxy)amino]methyl}propanoyl)-N-(phenylcarbonyl)-L-prolinamide LC-MS m/z 416 (MH+)

Example 4

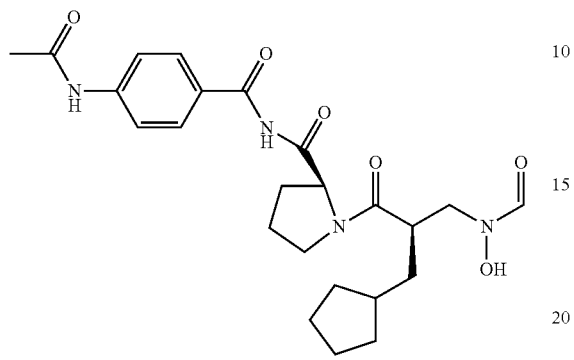

N-{[4-(acetylamino)phenyl]carbonyl}-1-((2R)-3-cyclopentyl-2-{[formyl(hydroxy)amino]methyl}propanoyl)-L-prolinamide LC-MS m/z 473 (MH+)

Example 5

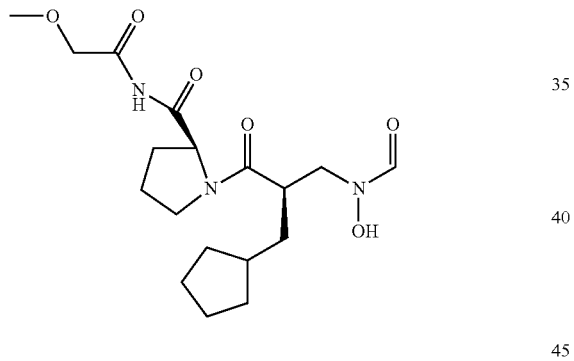

1-((2R)-3-cyclopentyl-2-{[formyl(hydroxy)amino]methyl}propanoyl)-N-[(methyl oxy)acetyl]-L-prolinamide LC-MS m/z 384 (MH+)

Example 6

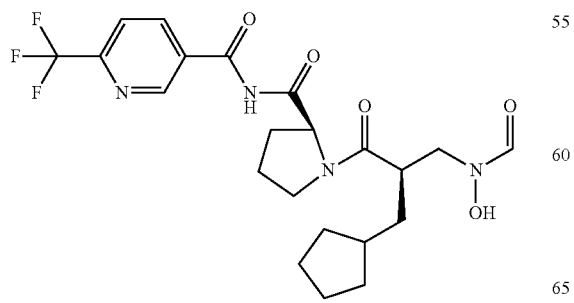

N-[1-((2R)-3-cyclopentyl-2-{[formyl(hydroxy)amino]methyl}propanoyl)-L-prolyl]-6-(trifluoromethyl)-3-pyridinecarboxamide LC-MS m/z 485 (MH+)

Example 7

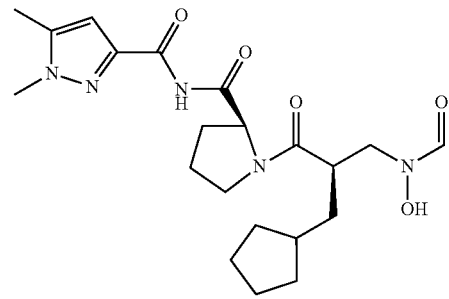

1-((2R)-3-cyclopentyl-2-{[formyl(hydroxy)amino]methyl}propanoyl)-N-[(1,5-dimethyl-1H-pyrazol-3-yl)carbonyl]-L-prolinamide LC-MS m/z 434 (MH+)

Example 8

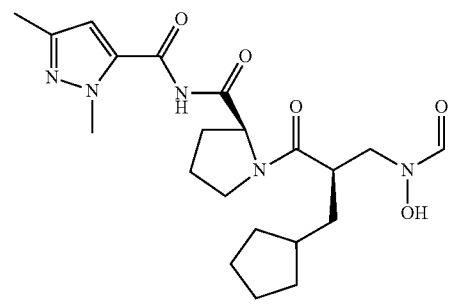

1-((2R)-3-cyclopentyl-2-{[formyl(hydroxy)amino]methyl}propanoyl)-N-[(1,3-dimethyl-1H-pyrazol-5-yl)carbonyl]-L-prolinamide LC-MS m/z 434 (MH+)

Example 9

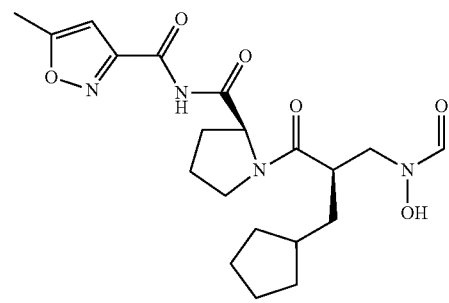

1-((2R)-3-cyclopentyl-2-{[formyl(hydroxy)amino]methyl}propanoyl)-N-[(5-methyl-3-isoxazolyl)carbonyl]-L-prolinamide LC-MS m/z 421 (MH+)

Example 10

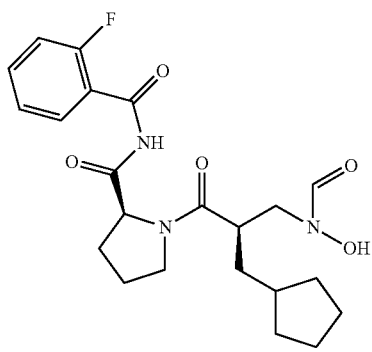

1-((2R)-3-cyclopentyl-2-{[formyl(hydroxy)amino]methyl}propanoyl)-N-[(2-fluorophenyl)carbonyl]-L-prolinamide LC-MS m/z 434 (MH+)

Example 11

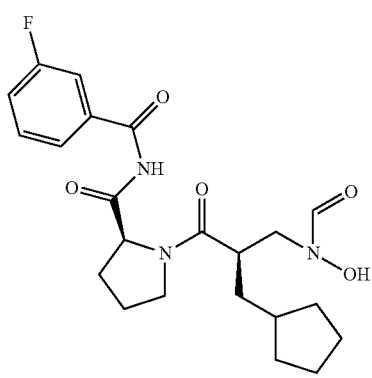

1-((2R)-3-cyclopentyl-2-{[formyl(hydroxy)amino]methyl}propanoyl)-N-[(3-fluorophenyl)carbonyl]-L-prolinamide LC-MS m/z 434 (MH+)

Example 12

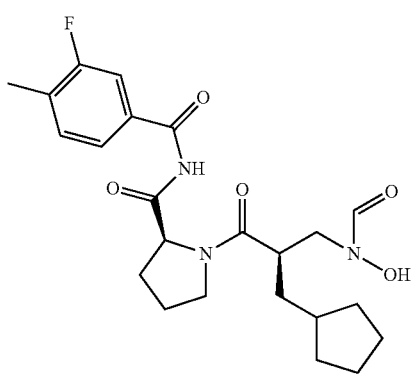

1-((2M-3-cyclopentyl-2-{[formyl(hydroxy)amino]methyl}propanoyl)-N-[(3-fluoro-4-methylphenyl)carbonyl]-L-prolinamide LC-MS m/z 448 (MH+)

Example 13

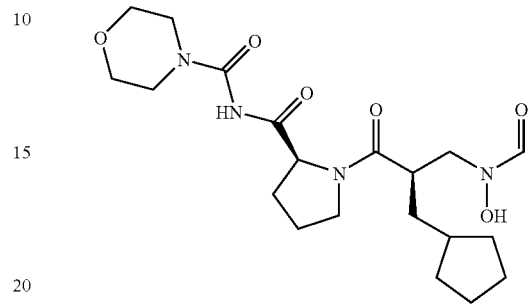

N-[1-((2R)-3-cyclopentyl-2-{[formyl(hydroxy)amino]methyl}propanoyl)-L-prolyl]-4-morpholinecarboxamide LC-MS m/z 425 (MH+)

Example 14

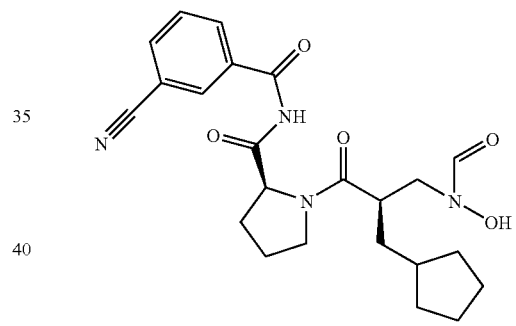

N-[(3-cyanophenyl)carbonyl]-1-((2R)-3-cyclopentyl-2-{[formyl(hydroxy)amino]methyl}propanoyl)-L-prolinamide LC-MS m/z 441 (MH+)

Example 15

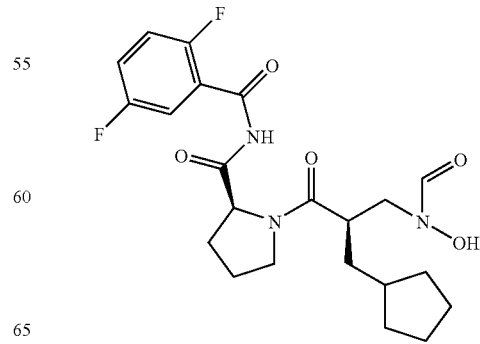

1-((2R)-3-cyclopentyl-2-{[formyl(hydroxy)amino]methyl}propanoyl)-N-[(2,5-difluorophenyl)carbonyl]-L-prolinamide LC-MS m/z 452 (MH+)

Example 16

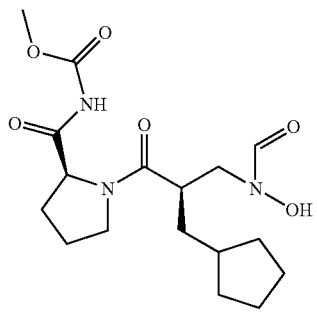

1-((2R)-3-cyclopentyl-2-{[formyl(hydroxy)amino]methyl}propanoyl)-N-[(methyloxy)carbonyl]-L-prolinamide LC-MS m/z 370 (MH+)

Example 17

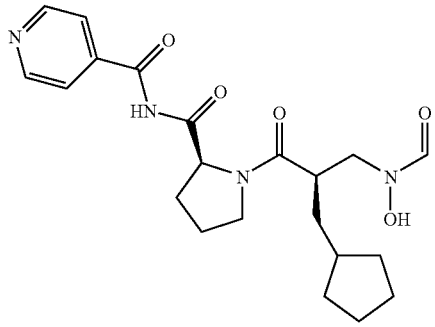

N-[1-((2R)-3-cyclopentyl-2-{[formyl(hydroxy)amino]methyl}propanoyl)-L-prolyl]-4-pyridinecarboxamide LC-MS m/z 417 (MH+)

Example 18

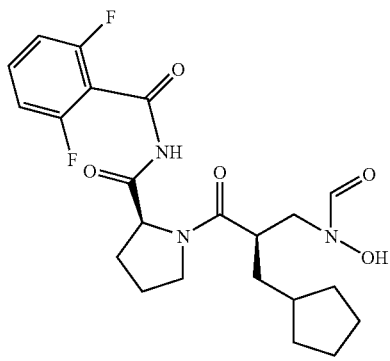

1-((2R)-3-cyclopentyl-2-{[formyl(hydroxy)amino]methyl}propanoyl)-N-[(2,6-difluorophenyl)carbonyl]-L-prolinamide LC-MS m/z 452 (MH+)

Example 19

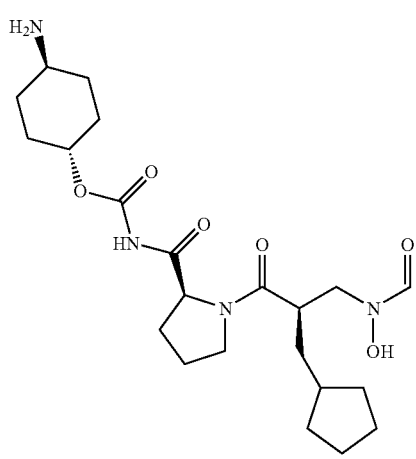

N-{[(trans-4-aminocyclohexyl)oxy]carbonyl}-1-((2R)-3-cyclopentyl-2-{[formyl(hydroxy)amino]methyl}propanoyl)-L-prolinamide LC-MS m/z 453 (MH+)

Example 20

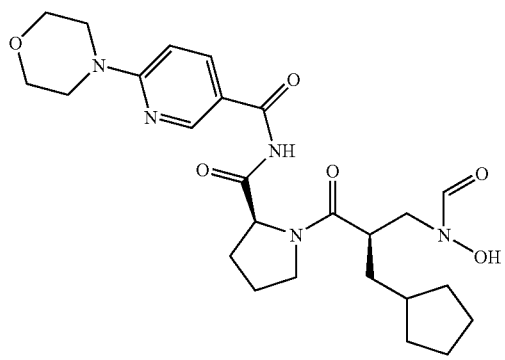

37

N-[1-((2R)-3-cyclopentyl-2-{[formyl(hydroxy)amino]methyl}propanoyl)-L-prolyl]-6-(4-morpholinyl)-3-pyridinecarboxamide LC-MS m/z 502 (MH+)

Example 21

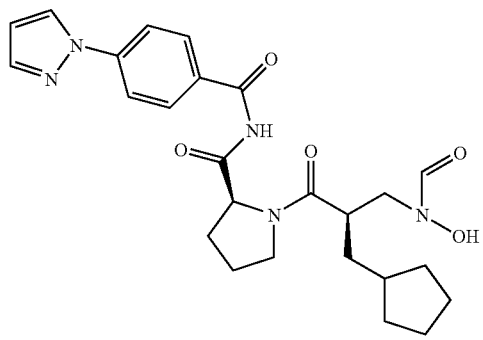

1-((2R)-3-cyclopentyl-2-{[formyl(hydroxy)amino]methyl}propanoyl)-N-{[4-(1H-pyrazol-1-yl)phenyl]carbonyl}-L-prolinamide LC-MS m/z 482 (MH+)

Example 22

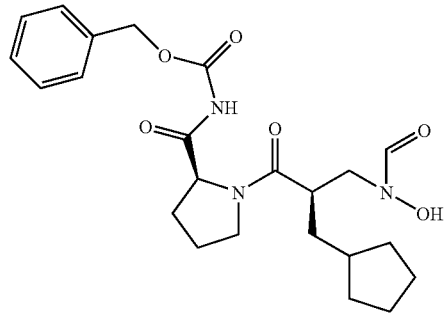

1-((2R)-3-cyclopentyl-2-{[formyl(hydroxy)amino]methyl}propanoyl)-N-{[(phenylmethyl)oxy]carbonyl}-L-prolinamide LC-MS m/z 446 (MH+)

Example 23

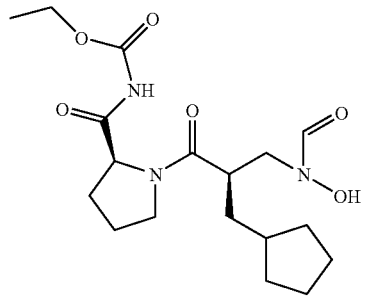

38

1-((2R)-3-cyclopentyl-2-{[formyl(hydroxy)amino]methyl}propanoyl)-N-[(ethyloxy)carbonyl]-L-prolinamide LC-MS m/z 384 (MH+)

Example 24

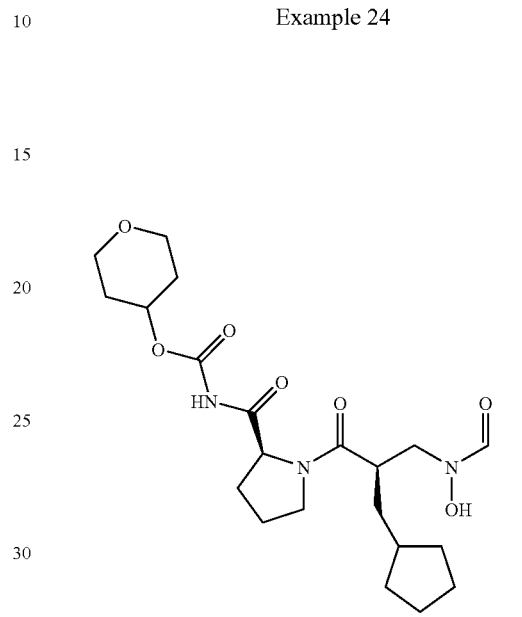

1-((2R)-3-cyclopentyl-2-{[formyl(hydroxy)amino]methyl}propanoyl)-N-[(tetrahydro-2H-pyran-4-yloxy)carbonyl]-L-prolinamide LC-MS m/z 440 (MH+)

Example 25

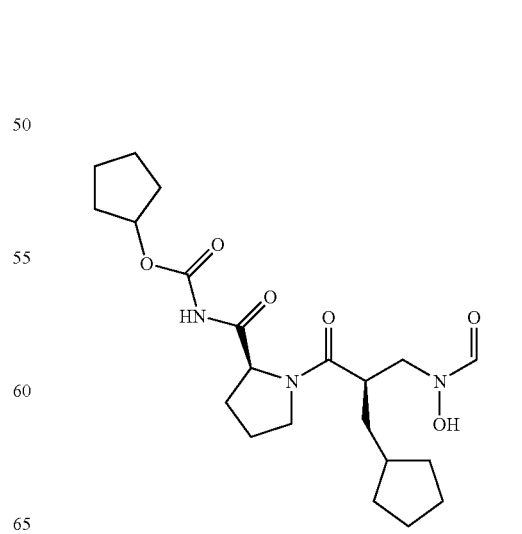

1-((2R)-3-cyclopentyl-2-{[formyl(hydroxy)amino]
methyl}propanoyl)-N-[(cyclopentyloxy)carbonyl]-L-
prolinamide LC-MS m/z 424 (MH+)

Example 26

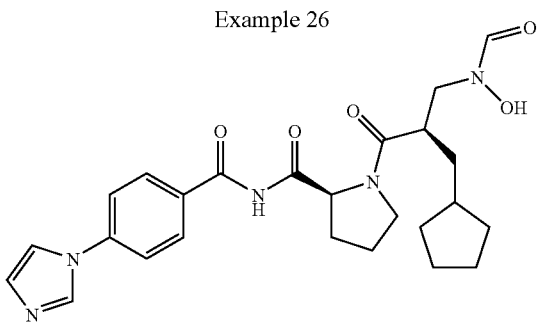

1-((2R)-3-cyclopentyl-2-{[formyl(hydroxy)amino]
methyl}propanoyl)-N-{[4-(1H-imidazol-1-yl)phe-
nyl]carbonyl}-L-prolinamide LC-MS m/z 482 (MH+)

Example 27

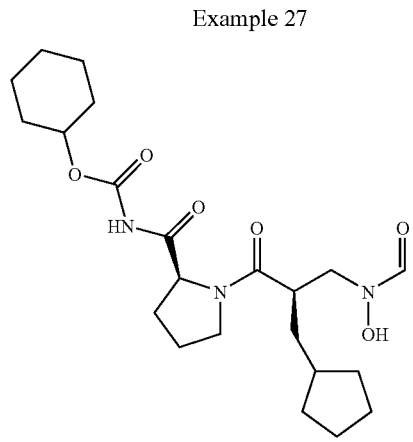

N-[(cyclohexyloxy)carbonyl]-1-((2R)-3-cyclopentyl-
2-{[formyl(hydroxy)amino]methyl}propanoyl)-L-
prolinamide LC-MS m/z 438 (MH+)

Example 28

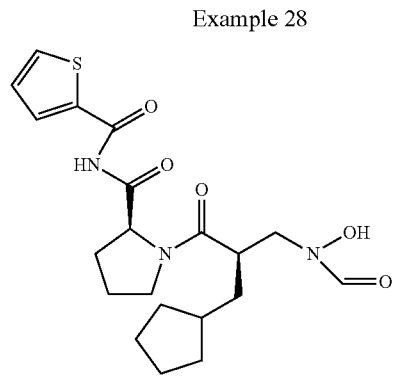

1-((2R)-3-cyclopentyl-2-{[formyl(hydroxy)amino]
methyl}propanoyl)-N-(2-thienylcarbonyl)-L-prolina-
mide LC-MS m/z 422 (MH+)

Example 29

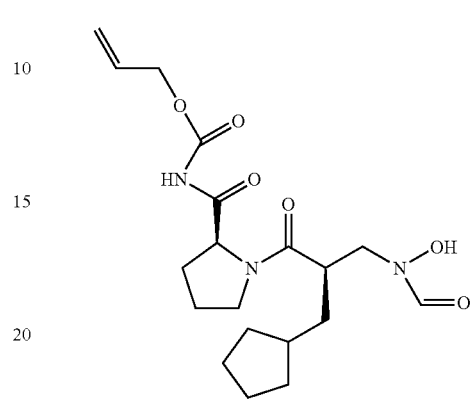

1-((2R)-3-cyclopentyl-2-{[formyl(hydroxy)amino]
methyl}propanoyl)-N-[(2-propen-1-yloxy)carbonyl]-
L-prolinamide LC-MS m/z 396 (MH+)

Example 30

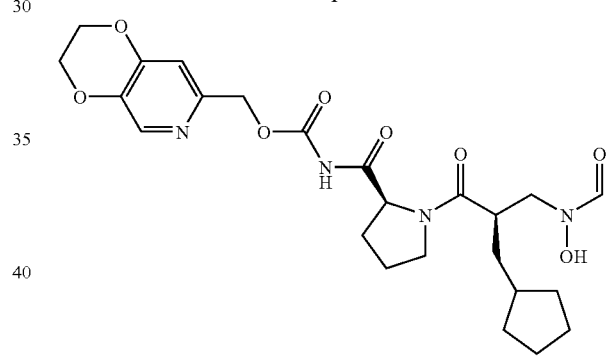

2,3-dihydro[1,4]dioxino[2,3-c]pyridin-7-ylmethyl[1-
((2R)-3-cyclopentyl-2-{[formyl(hydroxy)amino]
methyl}propanoyl)-L-prolyl]carbamate LC-MS m/z 505 (MH+)

Example 31

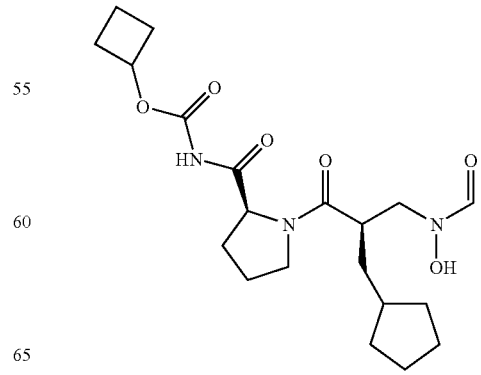

N-[(cyclobutyloxy)carbonyl]-1-((2R)-3-cyclopentyl-2-{[formyl(hydroxy)amino]methyl}propanoyl)-L-prolinamide LC-MS m/z 410 (MH+)

Example 32

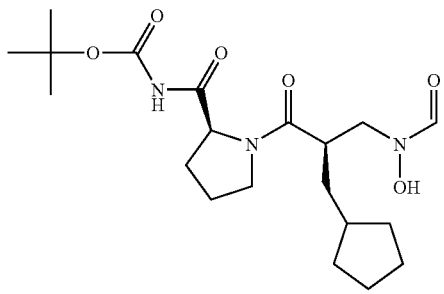

1-((2R)-3-cyclopentyl-2-{[formyl(hydroxy)amino]methyl}propanoyl)-N-{[(1,1-dimethylethyl)oxy]carbonyl}-L-prolinamide LC-MS m/z 412 (MH+)

Example 33

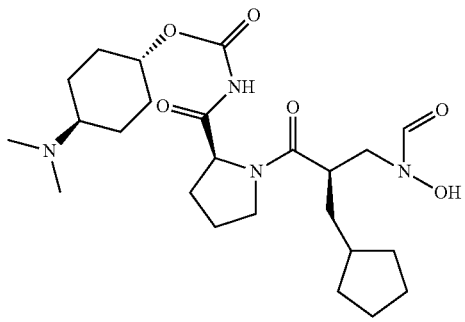

1-((2R)-3-cyclopentyl-2-{[formyl(hydroxy)amino]methyl}propanoyl)-N-({[trans-4-(dimethylamino)cyclohexyl]oxy}carbonyl)-L-prolinamide LC-MS m/z 481 (MH+)

Example 34

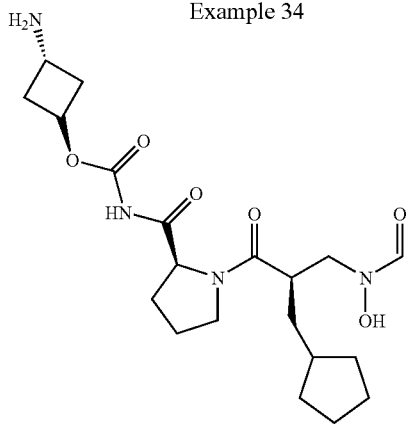

N-{[(trans-3-aminocyclobutyl)oxy]carbonyl}-1-((2R)-3-cyclopentyl-2-{[formyl(hydroxy)amino]methyl}propanoyl)-L-prolinamide LC-MS m/z 425 (MH+)

Example 35

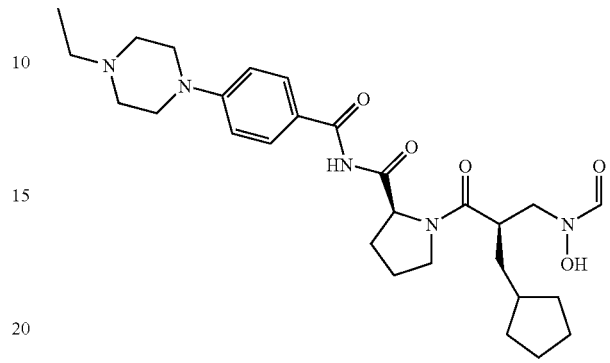

1-((2R)-3-cyclopentyl-2-{[formyl(hydroxy)amino]methyl}propanoyl)-N-{[4-(4-ethyl-1-piperazinyl)phenyl]carbonyl}-L-prolinamide LC-MS m/z 528 (MH+)

Example 36

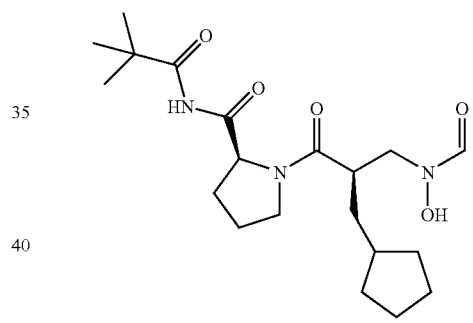

1-((2M)-3-cyclopentyl-2-{[formyl(hydroxy)amino]methyl}propanoyl)-N-(2,2-dimethylpropanoyl)-L-prolinamide LC-MS m/z 396 (MH+)

Example 37

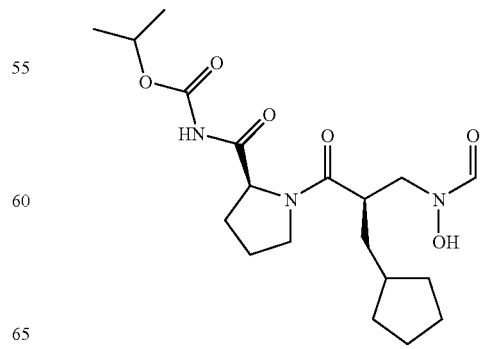

43

1-((2R)-3-cyclopentyl-2-{[formyl(hydroxy)amino]
methyl}propanoyl)-N-{[(1-methylethyl)oxy]carbo-
nyl}-L-prolinamide LC-MS m/z 398 (MH+)

Example 38

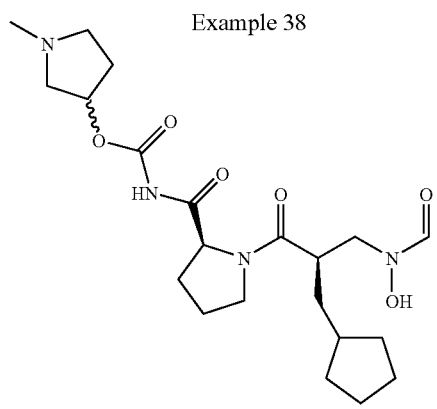

1-((2R)-3-cyclopentyl-2-{[formyl(hydroxy)amino]
methyl}propanoyl)-N-{[(1-methyl-3-pyrrolidinyl)
oxy]carbonyl}-L-prolinamide (mixture of diastere-
omers)

LC-MS m/z 439 (MH+)

Example 39

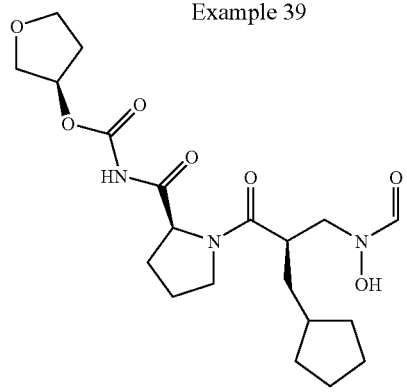

1-((2R)-3-cyclopentyl-2-{[formyl(hydroxy)amino]
methyl}propanoyl)-N-{[(3R)-tetrahydro-3-furany-
loxy]carbonyl}-L-prolinamide LC-MS m/z 426 (MH+)

Example 40

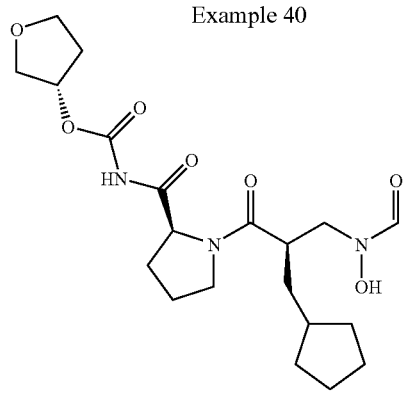

44

1-((2R)-3-cyclopentyl-2-{[formyl(hydroxy)amino]
methyl}propanoyl)-N-{[(3S)-tetrahydro-3-furany-
loxy]carbonyl}-L-prolinamide LC-MS m/z 426 (MH+)

Example 41

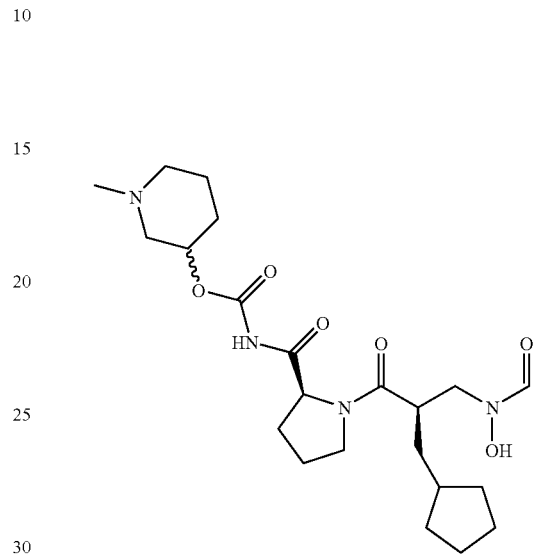

1-methyl-3-piperidinyl[1-((2R)-3-cyclopentyl-2-
{[formyl(hydroxy)amino]methyl}propanoyl)-L-pro-
lyl]carbamate (mixture of diastereomers)

LC-MS m/z 453 (MH+)

Example 42

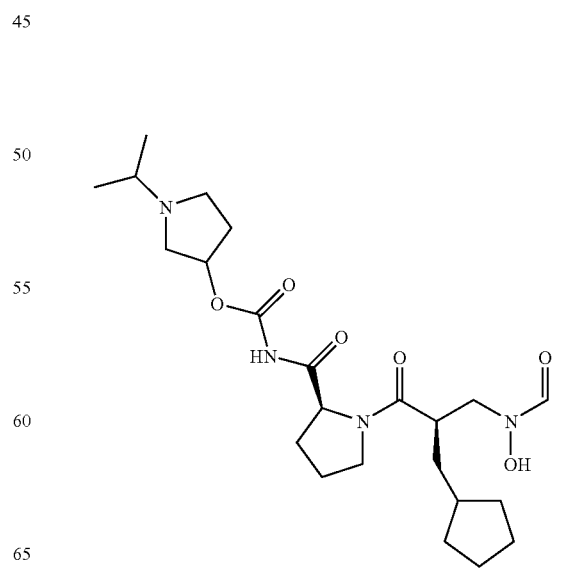

45

1-((2R)-3-cyclopentyl-2-{[formyl(hydroxy)amino]methyl}propanoyl)-N-({[1-(1-methylethyl)-3-pyrrolidinyl]oxy}carbonyl)-L-prolinamide (mixture of diastereomers)

LC-MS m/z 467 (MH+)

Example 43

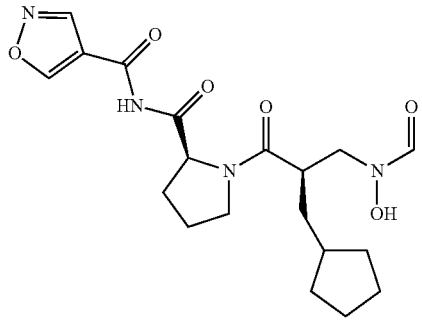

1-((2R)-3-cyclopentyl-2-{[formyl(hydroxy)amino]methyl}propanoyl)-N-(4-isoxazolylcarbonyl)-L-prolinamide LC-MS m/z 407 (MH+)

Example 44

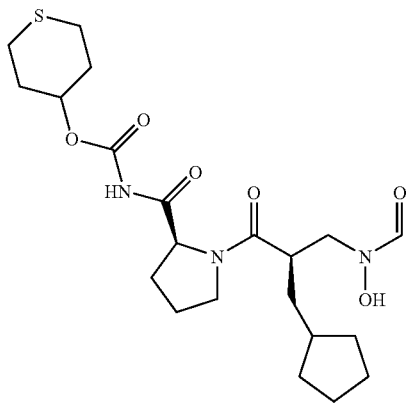

46

1-((2R)-3-cyclopentyl-2-{[formyl(hydroxy)amino]methyl}propanoyl)-N-[(tetrahydro-2H-thiopyran-4-yloxy)carbonyl]-L-prolinamide LC-MS m/z 456 (MH+)

Example 45

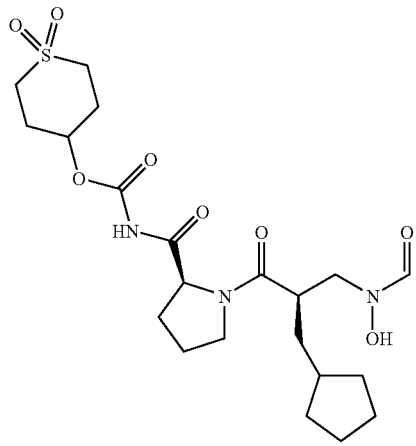

1-((2R)-3-cyclopentyl-2-{[formyl(hydroxy)amino]methyl}propanoyl)-N-{[(1,1-dioxidotetrahydro-2H-thiopyran-4-yl)oxy]carbonyl}-L-prolinamide LC-MS m/z 488 (MH+)

Example 46

47

1-((2R)-3-cyclopentyl-2-{[formyl(hydroxy)amino]methyl}propanoyl)-N-({[(1S)-1-methyl-2-(methyloxy)ethyl]oxy}carbonyl)-L-prolinamide LC-MS m/z 428 (MH+)

Example 47

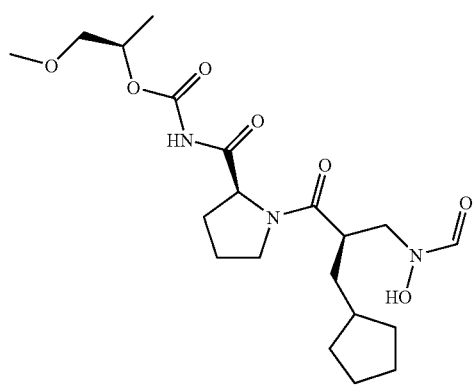

1-((2R)-3-cyclopentyl-2-{[formyl(hydroxy)amino]methyl}propanoyl)-N-({[(1R)-1-methyl-2-(methyloxy)ethyl]oxy}carbonyl)-L-prolinamide LC-MS m/z 428 (MH+)

Example 48

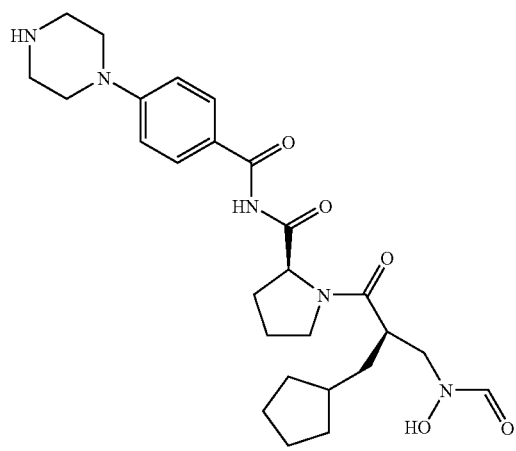

48

1-((2R)-3-cyclopentyl-2-{[formyl(hydroxy)amino]methyl}propanoyl)-N-{[4-(1-piperazinyl)phenyl]carbonyl}-L-prolinamide LC-MS m/z 500 (MH+)

Example 49

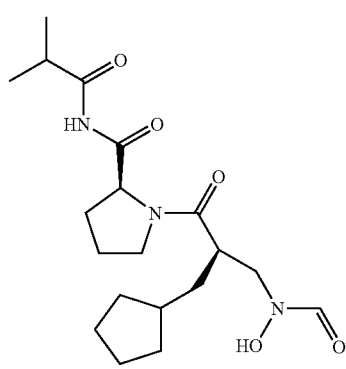

1-((2R)-3-cyclopentyl-2-{[formyl(hydroxy)amino]methyl}propanoyl)-N-(2-methylpropanoyl)-L-prolinamide LC-MS m/z 382 (MH+)

Example 50

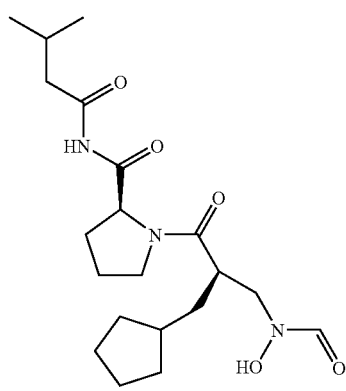

49

1-((2R)-3-cyclopentyl-2-{[formyl(hydroxy)amino]methyl}propanoyl)-N-(3-methylbutanoyl)-L-prolinamide LC-MS m/z 396 (MH+)

Example 51

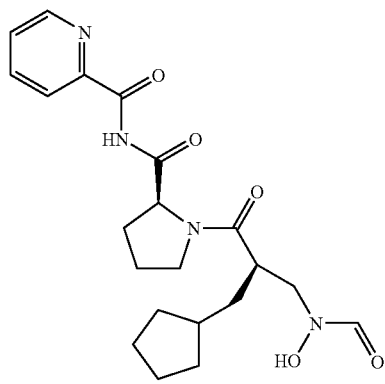

N-[1-((2R)-3-cyclopentyl-2-{[formyl(hydroxy)amino]methyl}propanoyl)-L-prolyl]-2-pyridinecarboxamide LC-MS m/z 417 (MH+)

Example 52

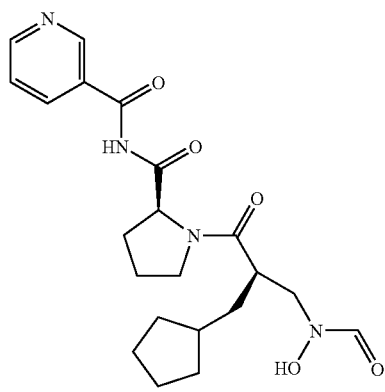

50

N-[1-((2R)-3-cyclopentyl-2-{[formyl(hydroxy)amino]methyl}propanoyl)-L-prolyl]-3-pyridinecarboxamide LC-MS m/z 417 (MH+)

Example 53

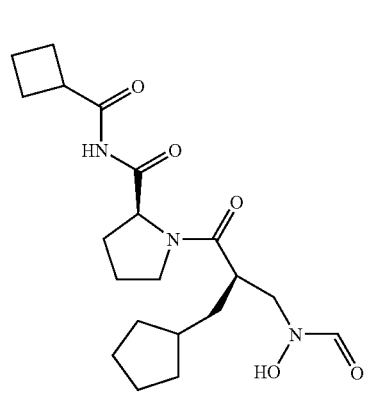

N-(cyclobutylcarbonyl)-1-((2R)-3-cyclopentyl-2-{[formyl(hydroxy)amino]methyl}propanoyl)-L-prolinamide LC-MS m/z 394 (MH+)

Example 54

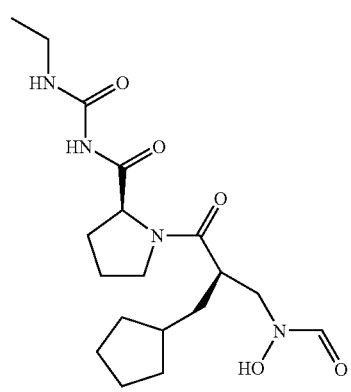

51

1-((2R)-3-cyclopentyl-2-{[formyl(hydroxy)amino]methyl}propanoyl)-N-[(ethylamino)carbonyl]-L-prolinamide LC-MS m/z 383 (MH+)

Example 55

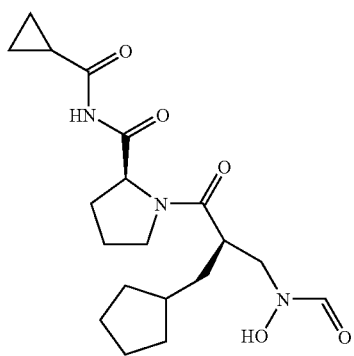

1-((2R)-3-cyclopentyl-2-{[formyl(hydroxy)amino]methyl}propanoyl)-N-(cyclopropylcarbonyl)-L-prolinamide LC-MS m/z 380 (MH+)

Example 56

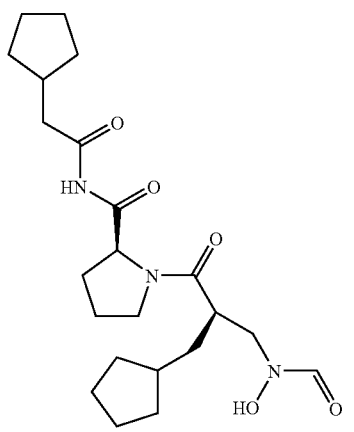

52

N-(cyclopentylacetyl)-1-((2R)-3-cyclopentyl-2-{[formyl(hydroxy)amino]methyl}propanoyl)-L-prolinamide LC-MS m/z 422 (MH+)

Example 57

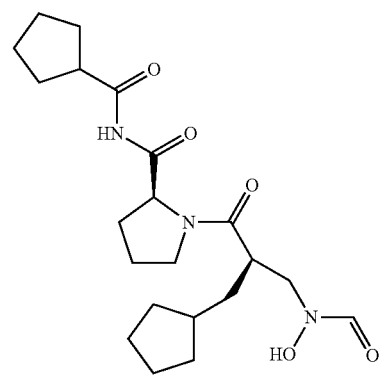

N-(cyclopentylcarbonyl)-1-((2R)-3-cyclopentyl-2-{[formyl(hydroxy)amino]methyl}propanoyl)-L-prolinamide LC-MS m/z 408 (MH+)

Example 58

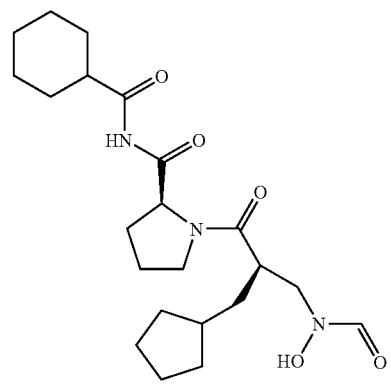

53

N-(cyclohexylcarbonyl)-1-((2R)-3-cyclopentyl-2-{[formyl(hydroxy)amino]methyl}propanoyl)-L-prolinamide LC-MS m/z 422 (MH+)

Example 59

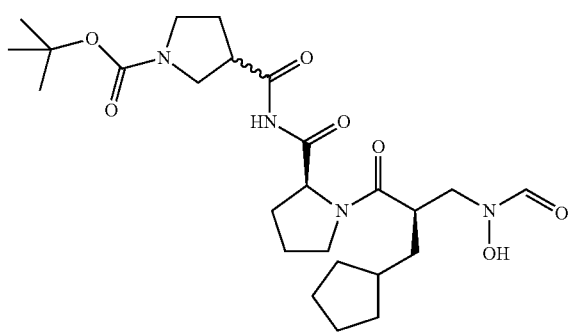

1,1-dimethylethyl 3-({[1-((2R)-3-cyclopentyl-2-{[formyl(hydroxy)amino]methyl}propanoyl)-L-prolyl]amino}carbonyl)-1-pyrrolidinecarboxylate (mixture of diastereomers)

LC-MS m/z 409 (MH-C$_4$H$_9$OC(O)+)

Example 60

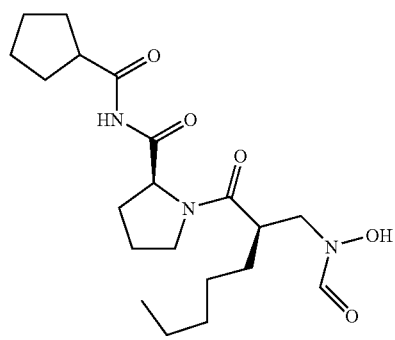

54

N-(cyclopentylcarbonyl)-1-((2R)-2-{[formyl(hydroxy)amino]methyl}heptanoyl)-L-prolinamide LC-MS m/z 396 (MH+)

Example 61

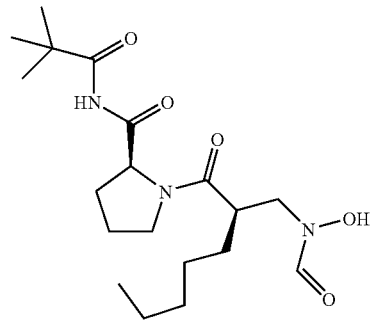

N-(2,2-dimethylpropanoyl)-1-((2R)-2-{[formyl(hydroxy)amino]methyl}heptanoyl)-L-prolinamide LC-MS m/z 384 (MH+)

Example 62

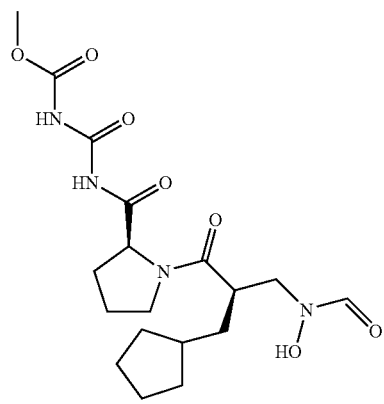

1-((2R)-3-cyclopentyl-2-{[formyl(hydroxy)amino]methyl}propanoyl)-N-({[(methyloxy)carbonyl]amino}carbonyl)-L-prolinamide LC-MS m/z 413 (MH+)

Example 63

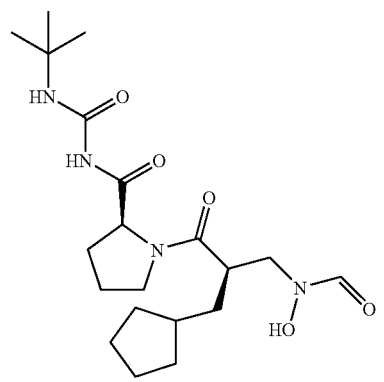

1-((2R)-3-cyclopentyl-2-{[formyl(hydroxy)amino]
methyl}propanoyl)-N-{[(1,1-dimethylethyl)amino]
carbonyl}-L-prolinamide LC-MS m/z 411 (MH+)

Example 64

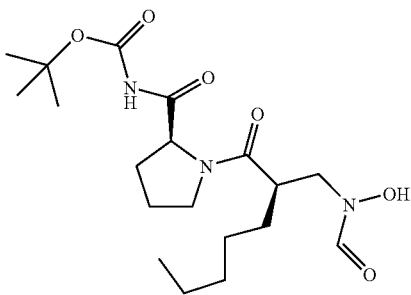

N-{[(1,1-dimethylethyl)oxy]carbonyl}-1-((2R)-2-
{[formyl(hydroxy)amino]methyl}heptanoyl)-L-pro-
linamide LC-MS m/z 400 (MH+)

Example 65

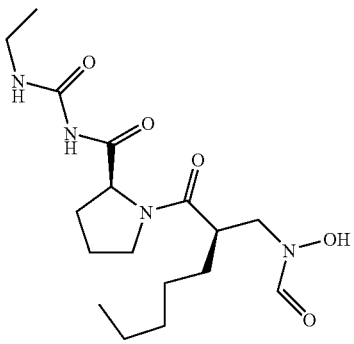

N-[(ethylamino)carbonyl]-1-((2R)-2-{[formyl(hy-
droxy)amino]methyl}heptanoyl)-L-prolinamide LC-MS m/z 371 (MH+)

Example 66

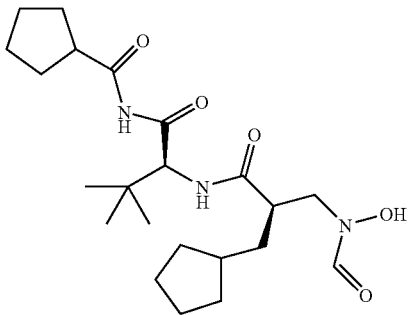

$N^1$-(cyclopentylcarbonyl)-$N^2$-((2R)-3-cyclopentyl-2-
{[formyl(hydroxy)amino]methyl}propanoyl)-3-me-
thyl-L-valinamide LC-MS m/z 424 (MH+)

Example 67

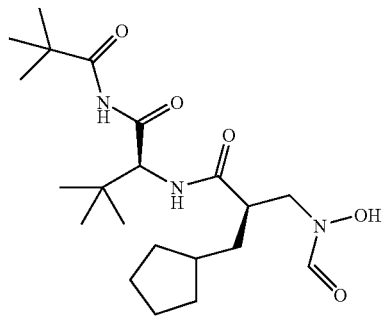

$N^2$-((2R)-3-cyclopentyl-2-{[formyl(hydroxy)amino]
methyl}propanoyl)-$N^1$-(2,2-dimethylpropanoyl)-3-
methyl-L-valinamide LC-MS m/z 412 (MH+)

Example 68

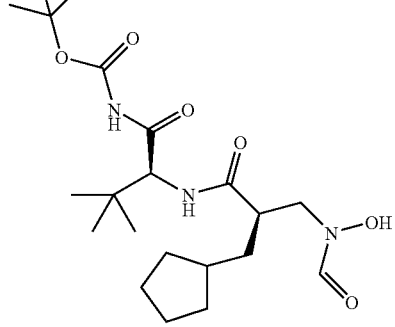

$N^2$-((2R)-3-cyclopentyl-2-{[formyl(hydroxy)amino]
methyl}propanoyl)-#-{[(1,1-dimethylethyl)oxy]car-
bonyl}-3-methyl-L-valinamide LC-MS m/z 428 (MH+)

Example 69

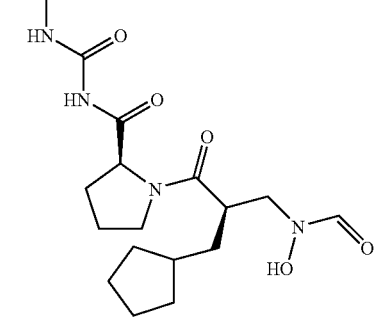

57

1-((2R)-3-cyclopentyl-2-{[formyl(hydroxy)amino]methyl}propanoyl)-N-{[(1-methylethyl)amino]carbonyl}-L-prolinamide LC-MS m/z 397 (MH+)

Example 70

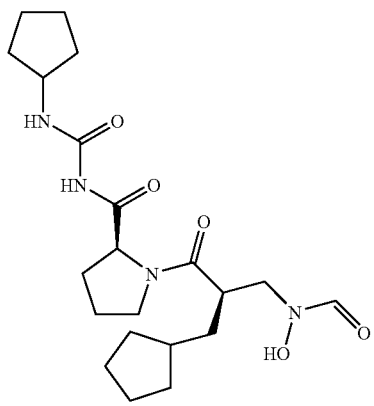

N-[(cyclopentylamino)carbonyl]-1-((2R)-3-cyclopentyl-2-{[formyl(hydroxy)amino]methyl}propanoyl)-L-prolinamide LC-MS m/z 423 (MH+)

Example 71

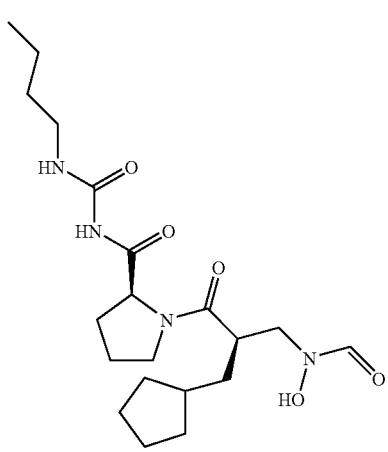

58

N-[(butylamino)carbonyl]-1-((2R)-3-cyclopentyl-2-{[formyl(hydroxy)amino]methyl}propanoyl)-L-prolinamide LC-MS m/z 411 (MH+)

Example 72

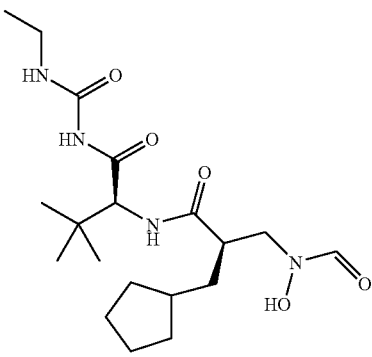

$N^2$-((2R)-3-cyclopentyl-2-{[formyl(hydroxy)amino]methyl}propanoyl)-$N^1$-[(ethylamino)carbonyl]-3-methyl-L-valinamide LC-MS m/z 399 (MH+)

Example 73

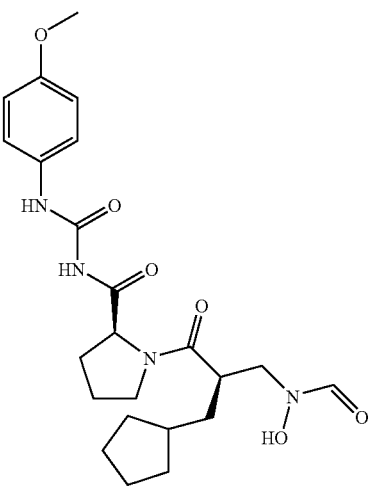

1-((2R)-3-cyclopentyl-2-{[formyl(hydroxy)amino]
methyl}propanoyl)-N-({[4-(methyloxy)phenyl]
amino}carbonyl)-L-prolinamide LC-MS m/z 461 (MH+)

Example 74

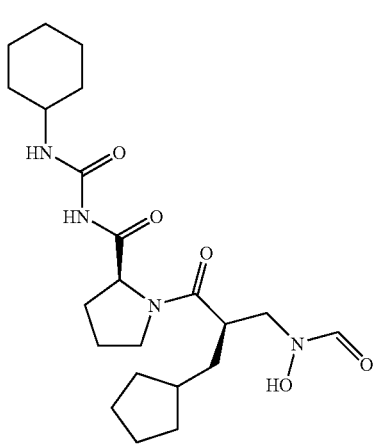

N-[(cyclohexylamino)carbonyl]-1-((2R)-3-cyclopen-
tyl-2-{[formyl(hydroxy)amino]methyl}propanoyl)-
L-prolinamide LC-MS m/z 437 (MH+)

Example 75

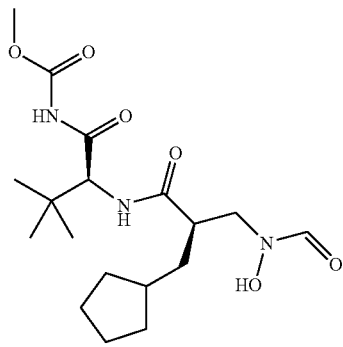

$N^2$-((2R)-3-cyclopentyl-2-{[formyl(hydroxy)amino]
methyl}propanoyl)-3-methyl-$N^1$-[(methyloxy)carbo-
nyl]-L-valinamide LC-MS m/z 386 (MH+)

Example 76

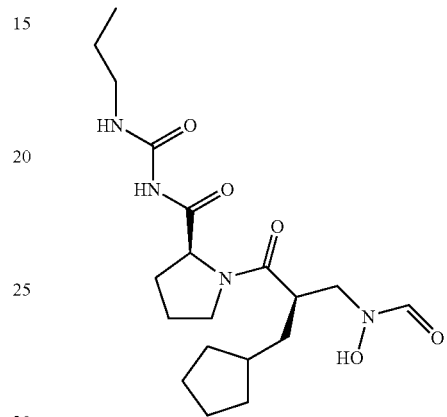

1-((2R)-3-cyclopentyl-2-{[formyl(hydroxy)amino]
methyl}propanoyl)-N-[(propylamino)carbonyl]-L-
prolinamide LC-MS m/z 397 (MH+)

Example 77

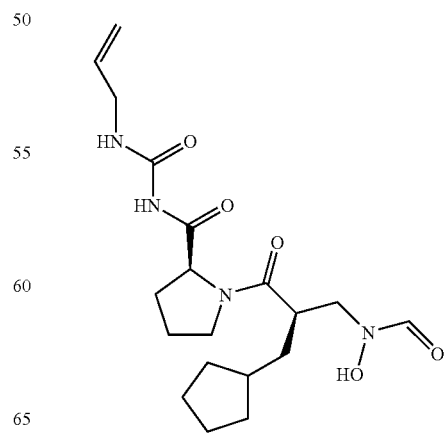

61

1-((2R)-3-cyclopentyl-2-{[formyl(hydroxy)amino]
methyl}propanoyl)-N-[(2-propen-1-ylamino)carbo-
nyl]-L-prolinamide LC-MS m/z 395 (MH+)

Example 78

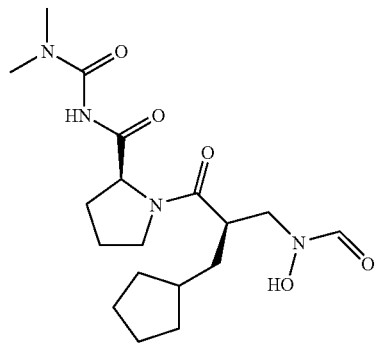

1-((2R)-3-cyclopentyl-2-{[formyl(hydroxy)amino]
methyl}propanoyl)-N-[(dimethylamino)carbonyl]-L-
prolinamide LC-MS m/z 383 (MH+)

Example 79

62

1-((2R)-3-cyclopentyl-2-{[formyl(hydroxy)amino]
methyl}propanoyl)-N-{[(phenylmethyl)amino]car-
bonyl}-L-prolinamide LC-MS m/z 445 (MH+)

Example 80

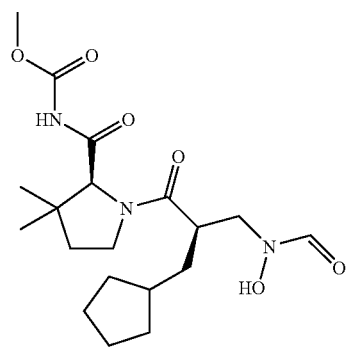

1-((2R)-3-cyclopentyl-2-{[formyl(hydroxy)amino]
methyl}propanoyl)-3,3-dimethyl-N-[(methyloxy)
carbonyl]-L-prolinamide LC-MS m/z 398 (MH+)

Example 81

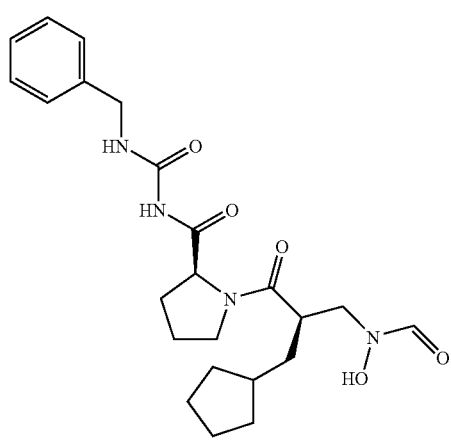

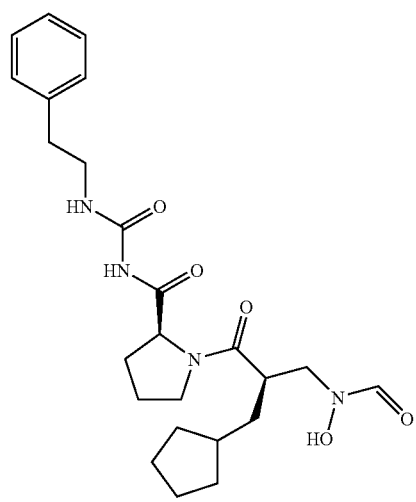

1-((2R)-3-cyclopentyl-2-{[formyl(hydroxy)amino]methyl}propanoyl)-N-{[(2-phenylethyl)amino]carbonyl}-L-prolinamide LC-MS m/z 459 (MH+)

Example 82

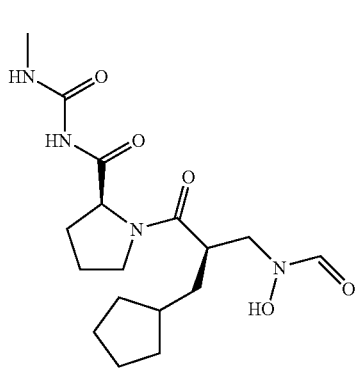

1-((2R)-3-cyclopentyl-2-{[formyl(hydroxy)amino]methyl}propanoyl)-N-[(methylamino)carbonyl]-L-prolinamide LC-MS m/z 369 (MH+)

Example 83

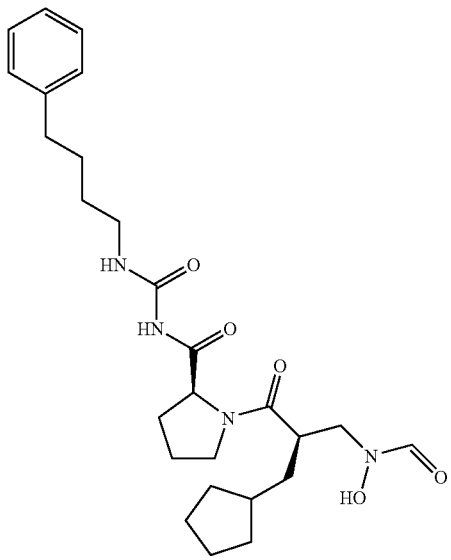

1-((2R)-3-cyclopentyl-2-{[formyl(hydroxy)amino]methyl}propanoyl)-N-{[(4-phenylbutyl)amino]carbonyl}-L-prolinamide LC-MS m/z 488 (MH+)

Example 84

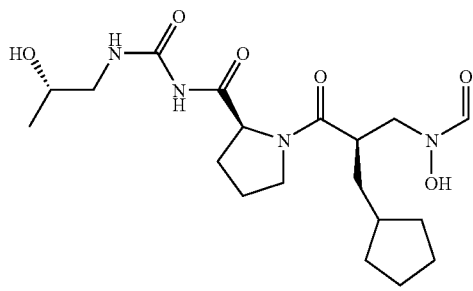

1-((2R)-3-cyclopentyl-2-{[formyl(hydroxy)amino]methyl}propanoyl)-N-({[(2S)-2-hydroxypropyl]amino}carbonyl)-L-prolinamide LC-MS m/z 413 (MH+)

Example 85

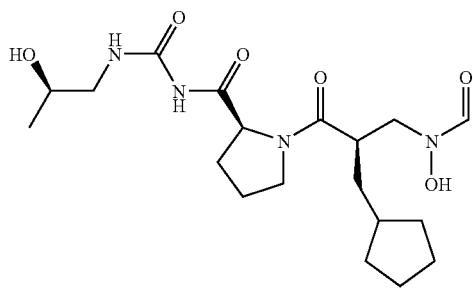

1-((2R)-3-cyclopentyl-2-{[formyl(hydroxy)amino]methyl}propanoyl)-N-({[(2R)-2-hydroxypropyl]amino}carbonyl)-L-prolinamide LC-MS m/z 413 (MH+)

Example 86

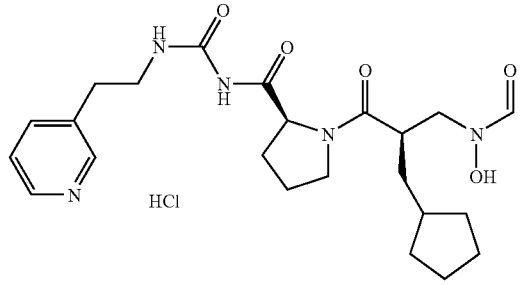

65

1-((2R)-3-cyclopentyl-2-{[formyl(hydroxy)amino]
methyl}propanoyl)-N-({[2-(3-pyridinyl)ethyl]
amino}carbonyl)-L-prolinamide hydrochloride LC-MS m/z 460 (MH+)

Example 87

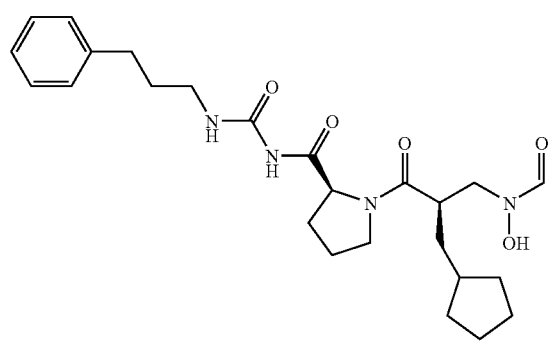

1-((2R)-3-cyclopentyl-2-{[formyl(hydroxy)amino]
methyl}propanoyl)-N-{[(3-phenylpropyl)amino]
carbonyl}-L-prolinamide LC-MS m/z 474 (MH+)

Example 88

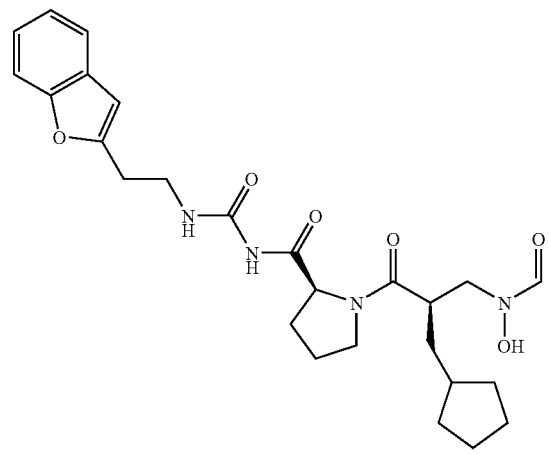

66

N-({[2-(1-benzofuran-2-yl)ethyl]amino}carbonyl)-1-
((2R)-3-cyclopentyl-2-{[formyl(hydroxy)amino]
methyl}propanoyl)-L-prolinamide LC-MS m/z 499 (MH+)

Example 89

1-((2R)-3-cyclopentyl-2-{[formyl(hydroxy)amino]
methyl}propanoyl)-N-({[2-(3,5-dimethyl-1H-pyra-
zol-4-yl)ethyl]amino}carbonyl)-L-prolinamide LC-MS m/z 477 (MH+)

Example 90

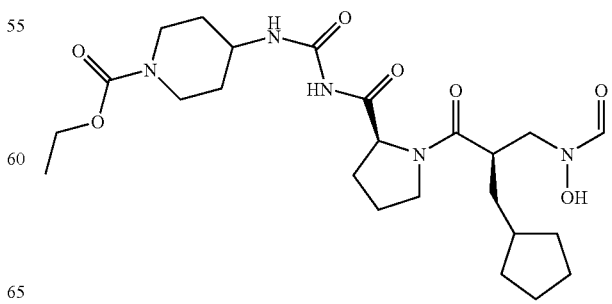

Ethyl 4-[({[1-((2R)-3-cyclopentyl-2-{[formyl(hydroxy)amino]methyl}propanoyl)-L-prolyl]amino}carbonyl)amino]-1-piperidinecarboxylate LC-MS m/z 510 (MH+)

Example 91

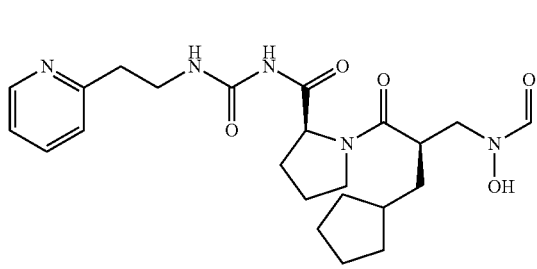

1-((2R)-3-cyclopentyl-2-{[formyl(hydroxy)amino]methyl}propanoyl)-N-({[2-(2-pyridinyl)ethyl]amino}carbonyl)-L-prolinamide LC-MS m/z 460 (MH+)

Example 92

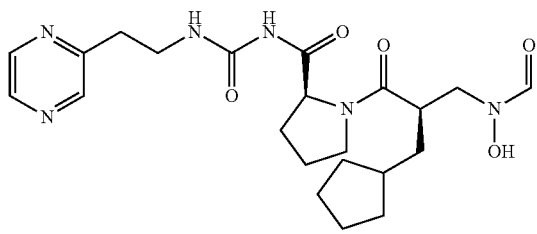

1-((2R)-3-cyclopentyl-2-{[formyl(hydroxy)amino]methyl}propanoyl)-N-({[2-(2-pyrazinyl)ethyl]amino}carbonyl)-L-prolinamide LC-MS m/z 461 (MH+)

Example 93

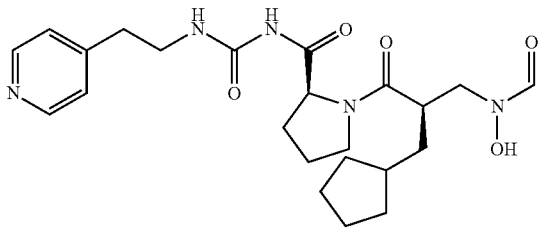

1-((2R)-3-cyclopentyl-2-{[formyl(hydroxy)amino]methyl}propanoyl)-N-({[2-(4-pyridinyl)ethyl]amino}carbonyl)-L-prolinamide LC-MS m/z 460 (MH+)

Example 94

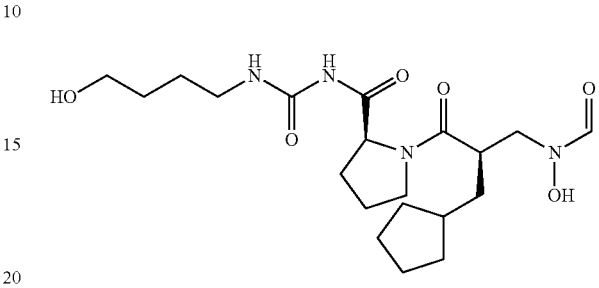

1-((2R)-3-cyclopentyl-2-{[formyl(hydroxy)amino]methyl}propanoyl)-N-{[(4-hydroxybutyl)amino]carbonyl}-L-prolinamide LC-MS m/z 427 (MH+)

Example 95

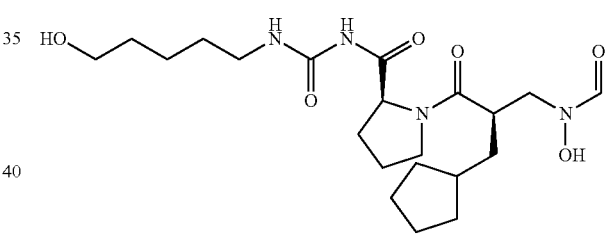

1-((2R)-3-cyclopentyl-2-{[formyl(hydroxy)amino]methyl}propanoyl)-N-{[(5-hydroxypentyl)amino]carbonyl}-L-prolinamide LC-MS m/z 441 (MH+)

Example 96

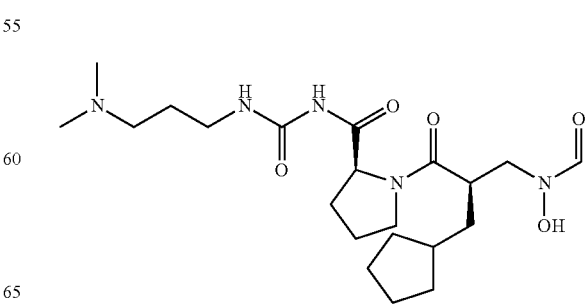

69

1-((2R)-3-cyclopentyl-2-{[formyl(hydroxy)amino]
methyl}propanoyl)-N-({[3-(dimethylamino)propyl]
amino}carbonyl)-L-prolinamide LC-MS m/z 440 (MH+)

Example 97

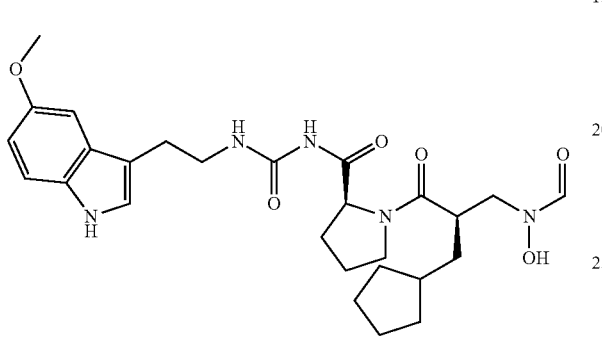

1-((2R)-3-cyclopentyl-2-{[formyl(hydroxy)amino]
methyl}propanoyl)-N-[({2-[5-(methyloxy)-1H-in-
dol-3-yl]ethyl}amino)carbonyl]-L-prolinamide LC-MS m/z 528 (MH+)

Example 98

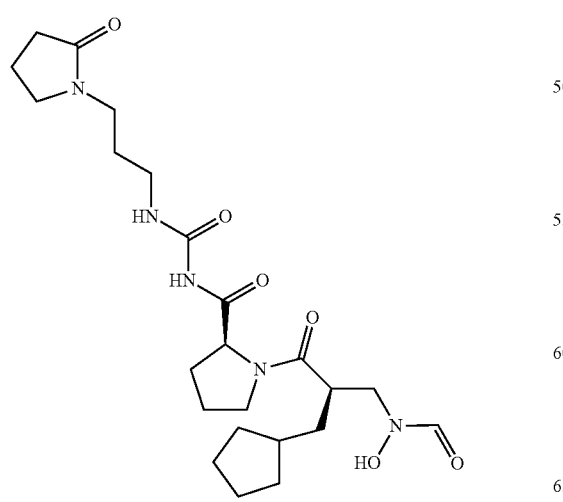

70

1-((2R)-3-cyclopentyl-2-{[formyl(hydroxy)amino]
methyl}propanoyl)-N-({[3-(2-oxo-1-pyrrolidinyl)
propyl]amino}carbonyl)-L-prolinamide LC-MS m/z 480 (MH+)

Example 99

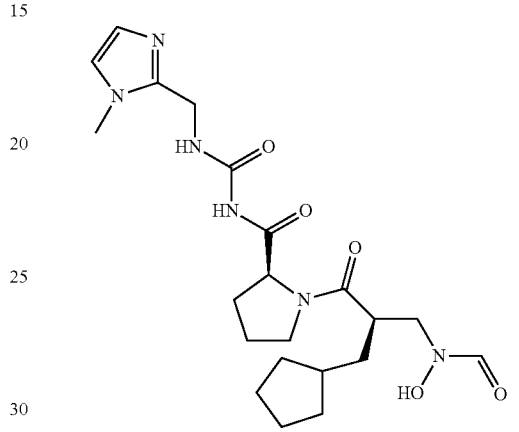

1-((2R)-3-cyclopentyl-2-{[formyl(hydroxy)amino]
methyl}propanoyl)-N-({[(1-methyl-1H-imidazol-2-
yl)methyl]amino}carbonyl)-L-prolinamide LC-MS m/z 449 (MH+)

Example 100

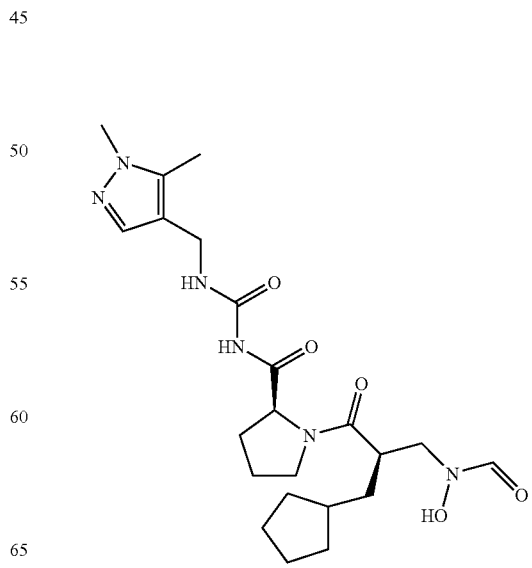

71

1-((2R)-3-cyclopentyl-2-{[formyl(hydroxy)amino]
methyl}propanoyl)-N-({[(1,5-dimethyl-1H-pyrazol-
4-yl)methyl]amino}carbonyl)-L-prolinamide LC-MS m/z 463 (MH+)

Example 101

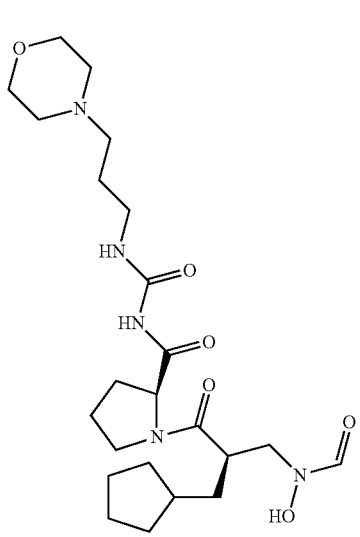

1-((2R)-3-cyclopentyl-2-{[formyl(hydroxy)amino]
methyl}propanoyl)-N-({[3-(4-morpholinyl)propyl]
amino}carbonyl)-L-prolinamide LC-MS m/z 482 (MH+)

Example 102

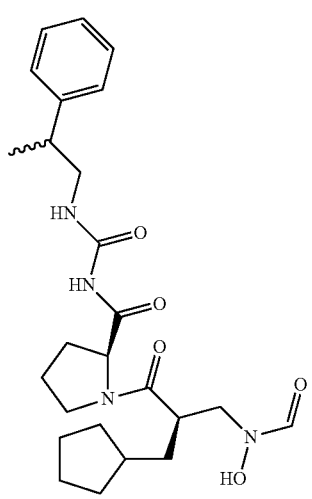

72

1-((2R)-3-cyclopentyl-2-{[formyl(hydroxy)amino]
methyl}propanoyl)-N-{[(2-phenylpropyl)amino]
carbonyl}-L-prolinamide (mixture of diastereomers)

LC-MS m/z 473 (MH+)

Example 103

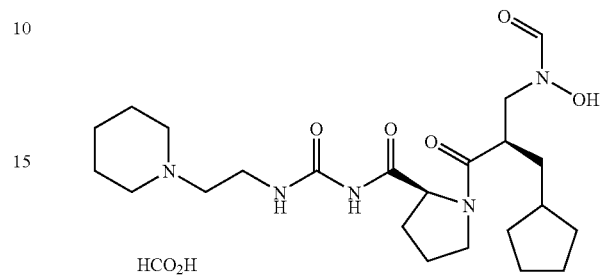

HCO₂H 1-((2R)-3-cyclopentyl-2-{[formyl(hydroxy)amino]
methyl}propanoyl)-N-({[2-(1-piperidinyl)ethyl]
amino}carbonyl)-L-prolinamide formate LC-MS m/z 466 (MH+)

Example 104

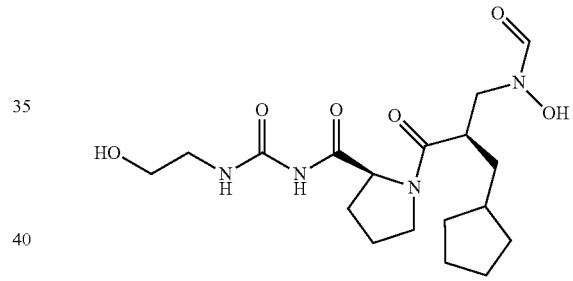

1-((2R)-3-cyclopentyl-2-{[formyl(hydroxy)amino]
methyl}propanoyl)-N-{[(2-hydroxyethyl)amino]
carbonyl}-L-prolinamide LC-MS m/z 399 (MH+)

Example 105

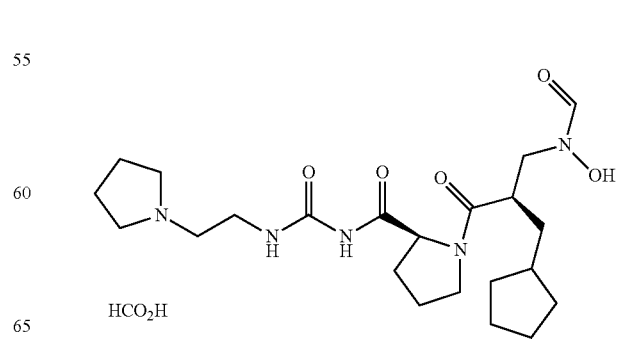

HCO₂H 1-((2R)-3-cyclopentyl-2-{[formyl(hydroxy)amino]methyl}propanoyl)-N-({[2-(1-pyrrolidinyl)ethyl]amino}carbonyl)-L-prolinamide formate LC-MS m/z 452 (MH+)

Example 106

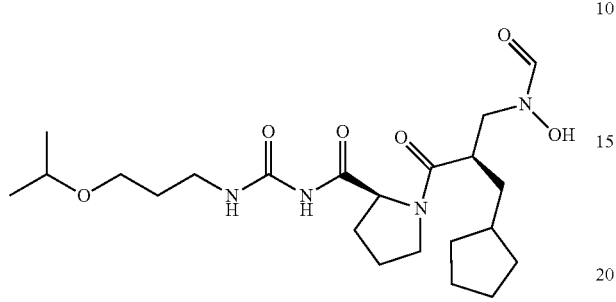

1-((2R)-3-cyclopentyl-2-{[formyl(hydroxy)amino]methyl}propanoyl)-N-[({3-[(1-methylethyl)oxy]propyl}amino)carbonyl]-L-prolinamide LC-MS m/z 455 (MH+)

Example 107

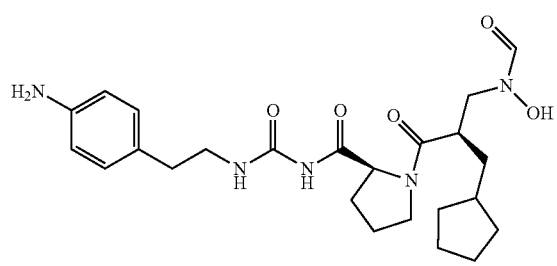

N-({[2-(4-aminophenyl)ethyl]amino}carbonyl)-1-((2R)-3-cyclopentyl-2-{[formyl(hydroxy)amino]methyl}propanoyl)-L-prolinamide LC-MS m/z 474 (MH+)

Example 108

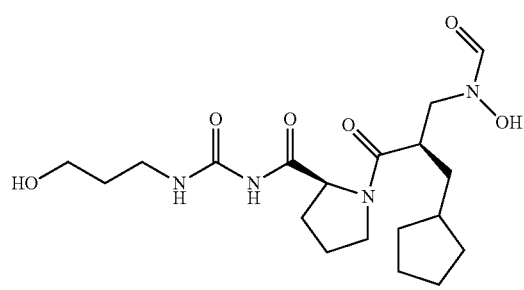

1-((2R)-3-cyclopentyl-2-{[formyl(hydroxy)amino]methyl}propanoyl)-N-{[(3-hydroxypropyl)amino]carbonyl}-L-prolinamide LC-MS m/z 413 (MH+)

Example 109

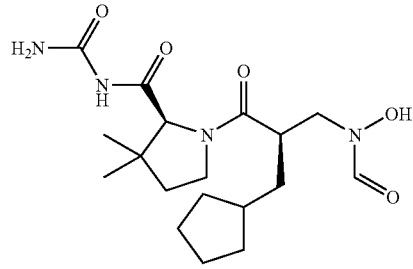

N-(aminocarbonyl)-1-((2R)-3-cyclopentyl-2-{[formyl(hydroxy)amino]methyl}propanoyl)-3,3-dimethyl-L-prolinamide LC-MS m/z 383 (MH+)

Example 110

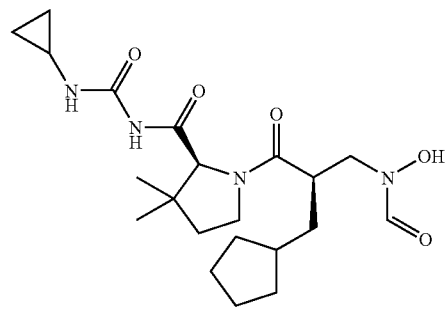

1-((2R)-3-cyclopentyl-2-{[formyl(hydroxy)amino]methyl}propanoyl)-N-[(cyclopropylamino)carbonyl]-3,3-dimethyl-L-prolinamide LC-MS m/z 423 (MH+)

Example 111

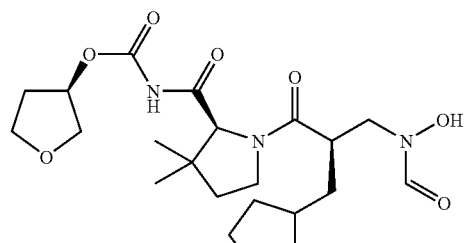

1-((2R)-3-cyclopentyl-2-{[formyl(hydroxy)amino]methyl}propanoyl)-3,3-dimethyl-N-{[(3R)-tetrahydro-3-furanyloxy]carbonyl}-L-prolinamide LC-MS m/z 454 (MH+)

Example 112

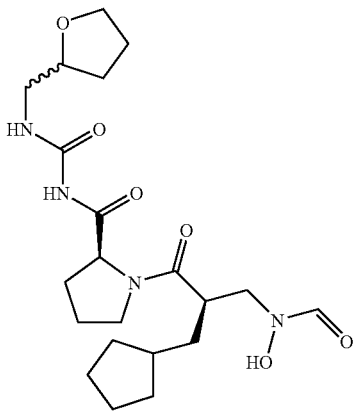

1-((2R)-3-cyclopentyl-2-{[formyl(hydroxy)amino]methyl}propanoyl)-N-{[(tetrahydro-2-furanylmethyl)amino]carbonyl}-L-prolinamide (mixture of diastereomers)

LC-MS m/z 439 (MH+)

Example 113

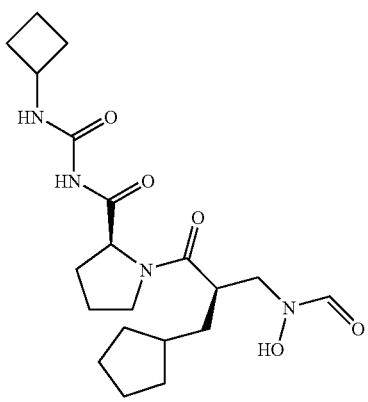

N-[(cyclobutylamino)carbonyl]-1-((2R)-3-cyclopentyl-2-{[formyl(hydroxy)amino]methyl}propanoyl)-L-prolinamide LC-MS m/z 409 (MH+)

Example 114

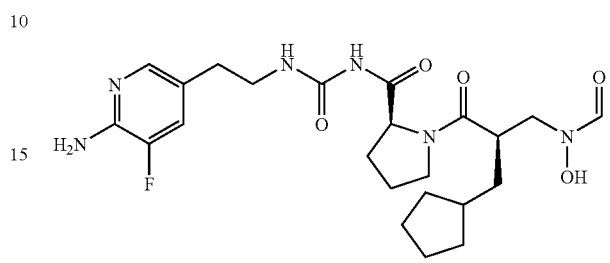

N-({[2-(6-amino-5-fluoro-3-pyridinyl)ethyl]amino}carbonyl)-1-((2R)-3-cyclopentyl-2-{[formyl(hydroxy)amino]methyl}propanoyl)-L-prolinamide LC-MS m/z 493 (MH+)

Example 115

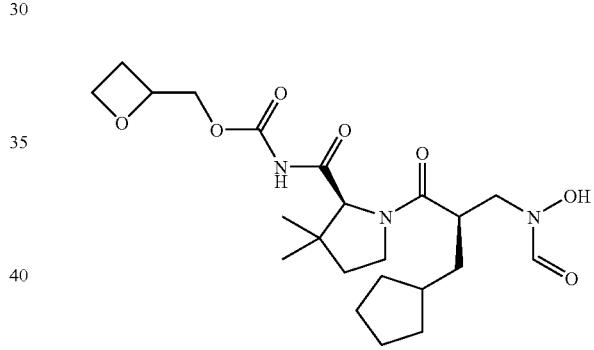

1-((2R)-3-cyclopentyl-2-{[formyl(hydroxy)amino]methyl}propanoyl)-3,3-dimethyl-N-{[(2-oxetanylmethyl)oxy]carbonyl}-L-prolinamide LC-MS m/z 454 (MH+)

Example 116

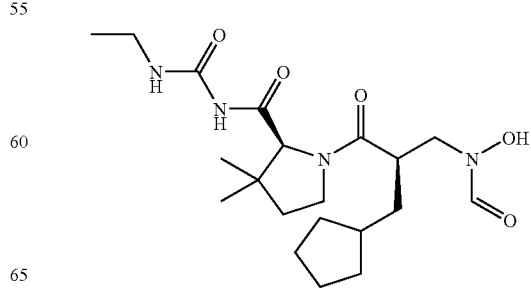

1-((2R)-3-cyclopentyl-2-{[formyl(hydroxy)amino]
methyl}propanoyl)-N-[(ethylamino)carbonyl]-3,3-
dimethyl-L-prolinamide LC-MS m/z 411 (MH+)

Example 117

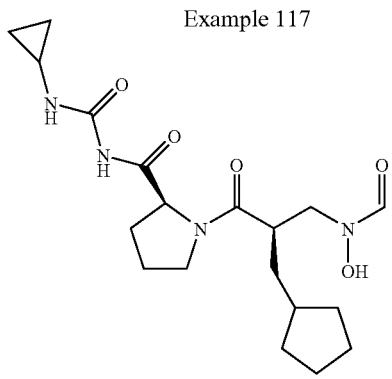

1-((2R)-3-cyclopentyl-2-{[formyl(hydroxy)amino]
methyl}propanoyl)-N-[(cyclopropylamino)carbo-
nyl]-L-prolinamide LC-MS m/z 395 (MH+)

Example 118

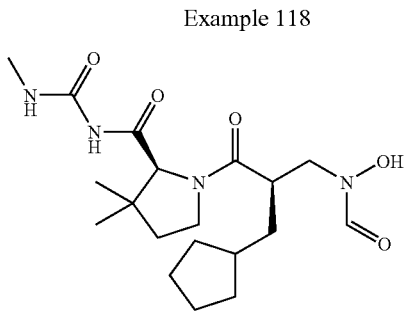

1-((2R)-3-cyclopentyl-2-{[formyl(hydroxy)amino]
methyl}propanoyl)-3,3-dimethyl-N-[(methylamino)
carbonyl]-L-prolinamide LC-MS m/z 397 (MH+)

Example 119

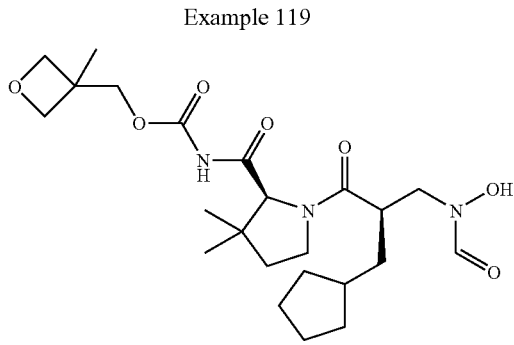

1-((2R)-3-cyclopentyl-2-{[formyl(hydroxy)amino]
methyl}propanoyl)-3,3-dimethyl-N-({[(3-methyl-3-
oxetanyl)methyl]oxy}carbonyl)-L-prolinamide LC-MS m/z 468 (MH+)

Example 120

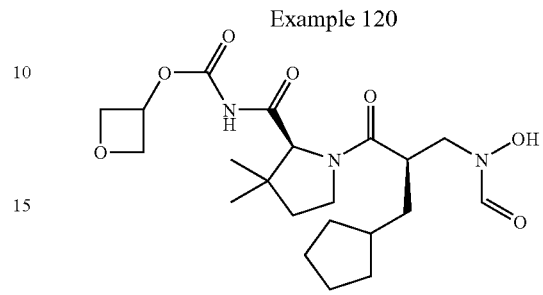

1-((2R)-3-cyclopentyl-2-{[formyl(hydroxy)amino]
methyl}propanoyl)-3,3-dimethyl-N-[(3-oxetanyloxy)
carbonyl]-L-prolinamide LC-MS m/z 440 (MH+)

Example 121

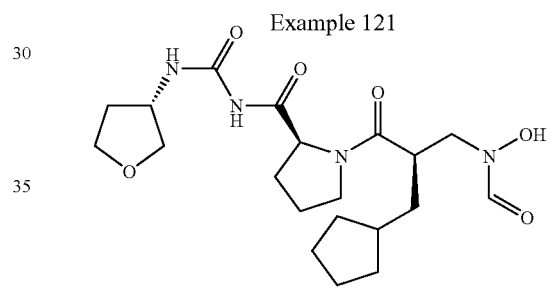

1-((2R)-3-cyclopentyl-2-{[formyl(hydroxy)amino]
methyl}propanoyl)-N-{[(3S)-tetrahydro-3-furany-
lamino]carbonyl}-L-prolinamide LC-MS m/z 425 (MH+)

Example 122

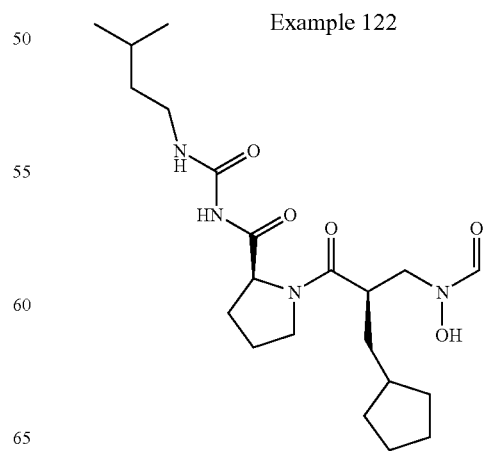

1-((2R)-3-cyclopentyl-2-{[formyl(hydroxy)amino]methyl}propanoyl)-N-{[(3-methylbutyl)amino]carbonyl}-L-prolinamide LC-MS m/z 425 (MH+)

Example 123

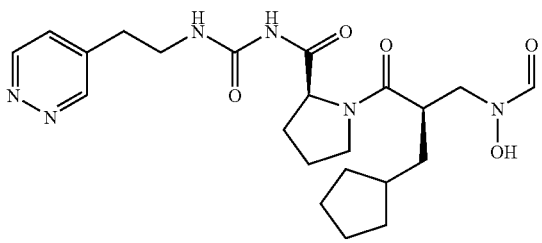

1-((2R)-3-cyclopentyl-2-{[formyl(hydroxy)amino]methyl}propanoyl)-N-({[2-(4-pyridazinyl)ethyl]amino}carbonyl)-L-prolinamide LC-MS m/z 461 (MH+)

Example 124

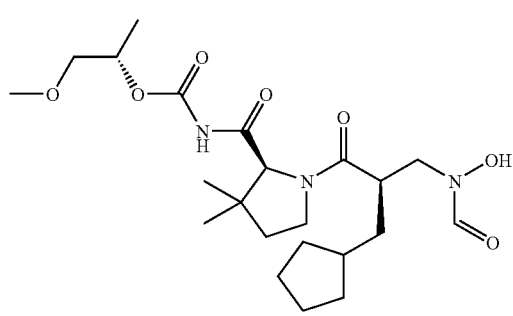

1-((2R)-3-cyclopentyl-2-{[formyl(hydroxy)amino]methyl}propanoyl)-3,3-dimethyl-N-({[(1S)-1-methyl-2-(methyloxy)ethyl]oxy}carbonyl)-L-prolinamide LC-MS m/z 456 (MH+)

Example 125

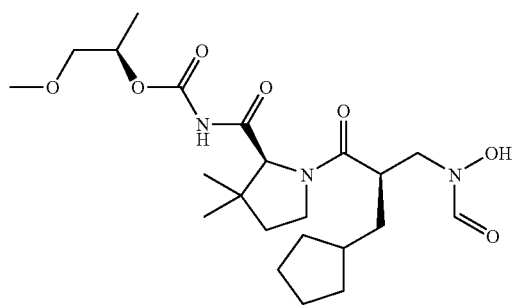

1-((2R)-3-cyclopentyl-2-{[formyl(hydroxy)amino]methyl}propanoyl)-3,3-dimethyl-N-({[(1R)-1-methyl-2-(methyloxy)ethyl]oxy}carbonyl)-L-prolinamide LC-MS m/z 456 (MH+)

Example 126

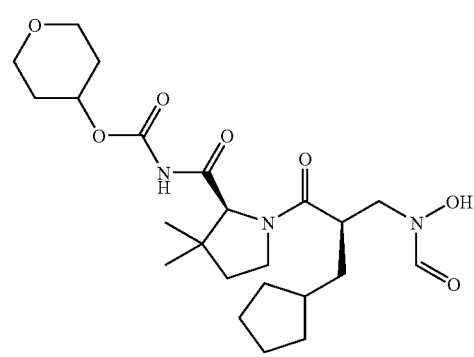

1-((2R)-3-cyclopentyl-2-{[formyl(hydroxy)amino]methyl}propanoyl)-3,3-dimethyl-N-[(tetrahydro-2H-pyran-4-yloxy)carbonyl]-L-prolinamide LC-MS m/z 468 (MH+)

Example 127

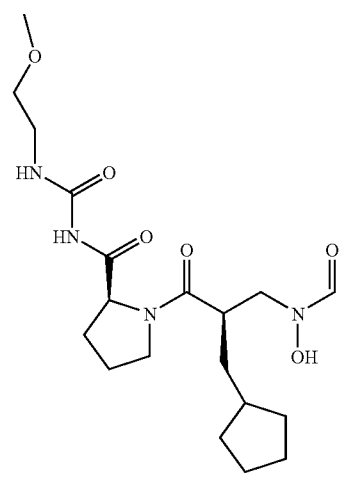

1-((2R)-3-cyclopentyl-2-{[formyl(hydroxy)amino]
methyl}propanoyl)-N-({[2-(methyloxy)ethyl]
amino}carbonyl)-L-prolinamide LC-MS m/z 413 (MH+)

Example 128

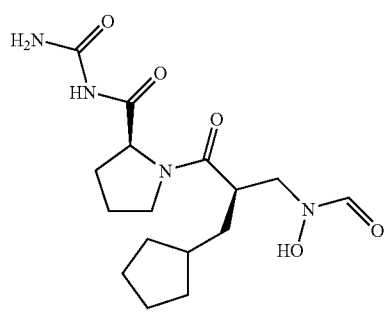

N-(aminocarbonyl)-1-((2R)-3-cyclopentyl-2-{
[formyl(hydroxy)amino]methyl}propanoyl)-L-proli-
namide LC-MS m/z 355 (MH+)

Example 129

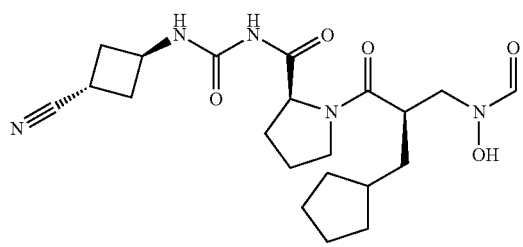

N-{[(trans-3-cyanocyclobutyl)amino]carbonyl}-1-
((2R)-3-cyclopentyl-2-{[formyl(hydroxy)amino]
methyl}propanoyl)-L-prolinamide LC-MS m/z 434 (MH+)

Example 130

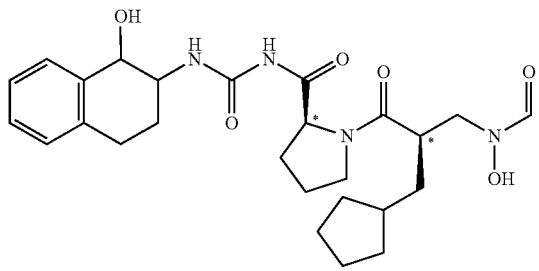

1-((2R)-3-cyclopentyl-2-{[(formyl(hydroxy)amino]
methyl}propanoyl)-N-{[(1-hydroxy-1,2,3,4-tetrahy-
dro-2-naphthalenyl)amino]carbonyl}-L-prolinamide
(mixture of trans-diastereomers)

LC-MS m/z 501 (MH+)

Example 131

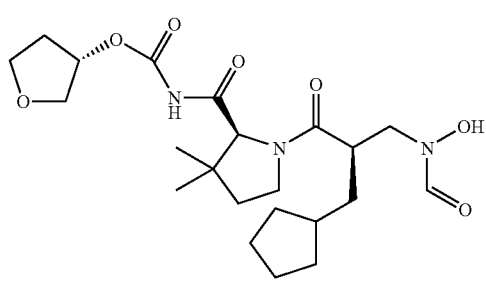

1-((2R)-3-cyclopentyl-2-{[formyl(hydroxy)amino]
methyl}propanoyl)-3,3-dimethyl-N-{[(3S)-tetrahy-
dro-3-furanyloxy]carbonyl}-L-prolinamide LC-MS m/z 454 (MH+)

Example 132

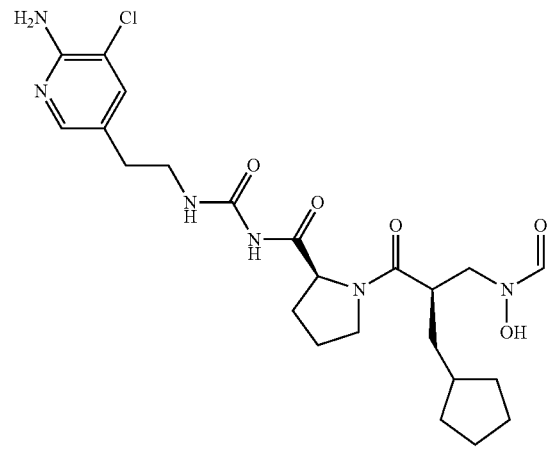

83

N-({[2-(6-amino-5-chloro-3-pyridinyl)ethyl]amino}carbonyl)-1-((2R)-3-cyclopentyl-2-{[formyl(hydroxy)amino]methyl}propanoyl)-L-prolinamide LC-MS m/z 509 (MH+)

Example 133

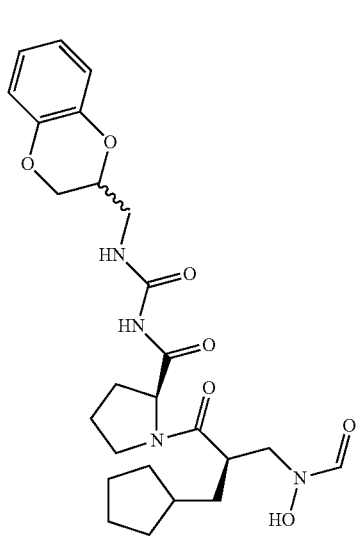

1-((2R)-3-cyclopentyl-2-{[formyl(hydroxy)amino]methyl}propanoyl)-N-{[(2,3-dihydro-1,4-benzodioxin-2-ylmethyl)amino]carbonyl}-L-prolinamide (mixture of diastereomers)

LC-MS m/z 503 (MH+)

Example 134

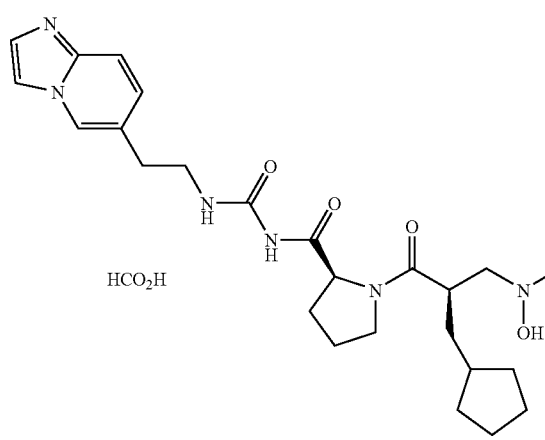

84

1-((2R)-3-cyclopentyl-2-{[formyl(hydroxy)amino]methyl}propanoyl)-N-{[(2-imidazo[1,2-a]pyridin-6-ylethyl)amino]carbonyl}-L-prolinamide formate LC-MS m/z 499 (MH+)

Example 135

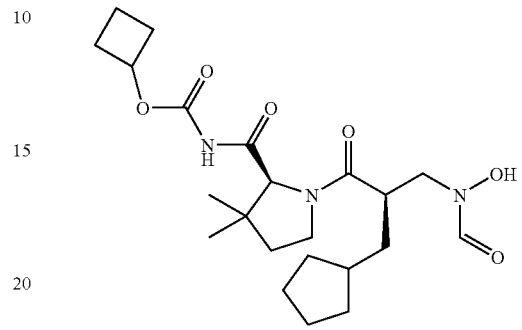

N-[(cyclobutyloxy)carbonyl]-1-((2R)-3-cyclopentyl-2-{[formyl(hydroxy)amino]methyl}propanoyl)-3,3-dimethyl-L-prolinamide LC-MS m/z 438 (MH+)

Example 136

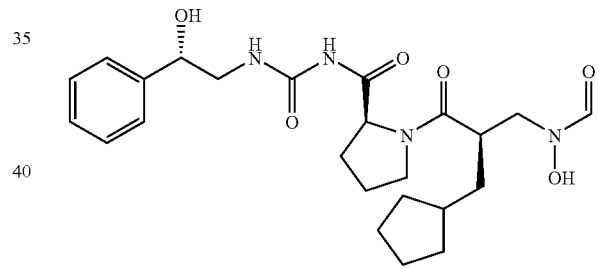

1-((2R)-3-cyclopentyl-2-{[formyl(hydroxy)amino]methyl}propanoyl)-N-({[(2S)-2-hydroxy-2-phenylethyl]amino}carbonyl)-L-prolinamide LC-MS m/z 475 (MH+)

Example 137

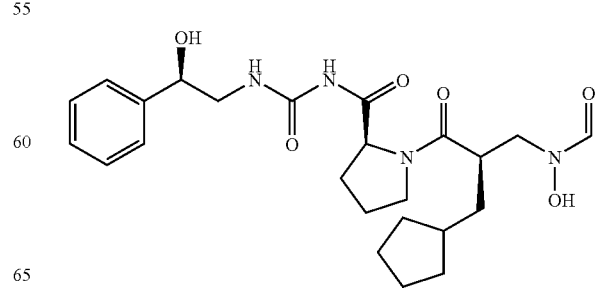

| 85 | 86 |
|---|---|
| 1-((2)-3-cyclopentyl-2-{[formyl(hydroxy)amino]methyl}propanoyl)-N-({[(2R)-2-hydroxy-2-phenyl-ethyl]amino}carbonyl)-L-prolinamide | 1-((2R)-3-cyclopentyl-2-{[formyl(hydroxy)amino]methyl}propanoyl)-N-[(2,3-dihydro-1H-inden-2-ylamino)carbonyl]-L-prolinamide |
| LC-MS m/z 475 (MH+) | LC-MS m/z 471 (MH+) |
| Example 138 | Example 140 |

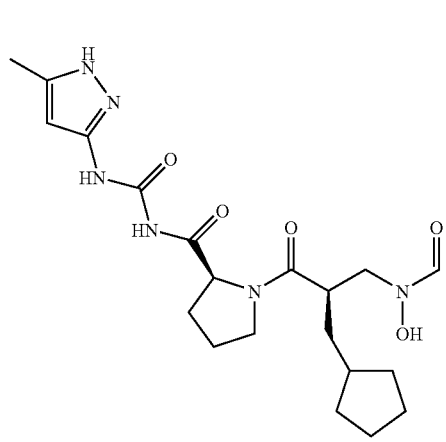

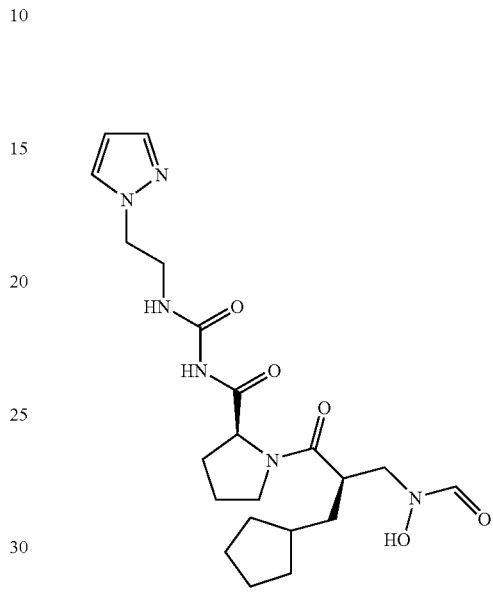

1-((2R)-3-cyclopentyl-2-{[formyl(hydroxy)amino]methyl}propanoyl)-N{([(5-methyl-1H-pyrazol-3-yl)amino]carbonyl}-L-prolinamide LC-MS m/z 435 (MH+)

Example 139

1-((2R)-3-cyclopentyl-2-{[formyl(hydroxy)amino]methyl}propanoyl)-N-({[2-(1H pyrazol-1-yl)ethyl]amino}carbonyl)-L-prolinamide LC-MS m/z 449 (MH+)

Example 141

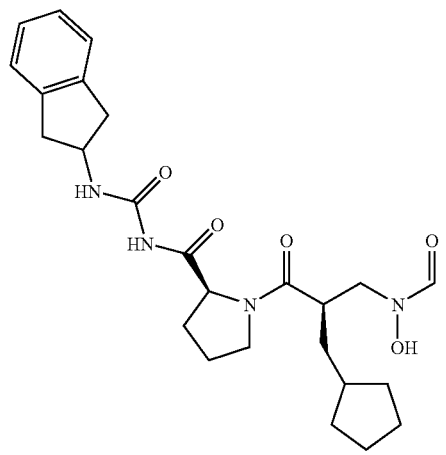

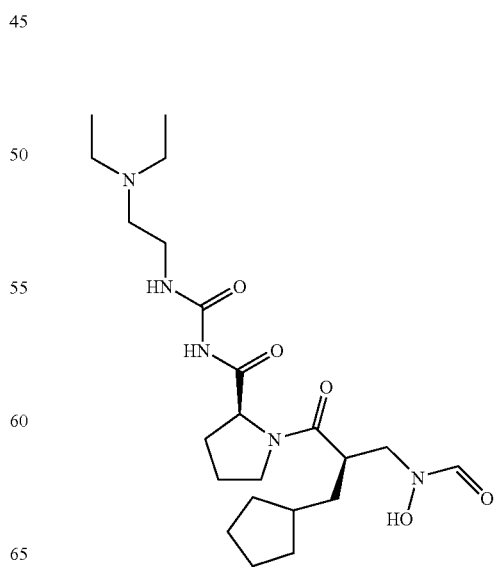

87

1-((2R)-3-cyclopentyl-2-{[formyl(hydroxy)amino]
methyl}propanoyl)-N-({[2-(diethylamino)ethyl]
amino}carbonyl)-L-prolinamide LC-MS m/z 454 (MH+)

Example 142

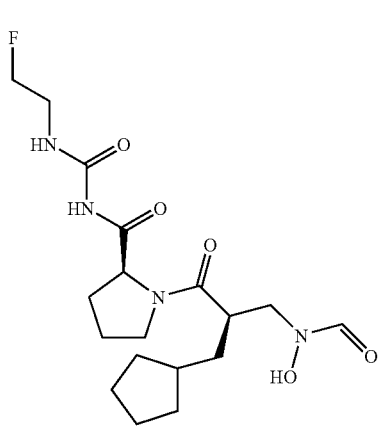

1-((2R)-3-cyclopentyl-2-{[formyl(hydroxy)amino]
methyl}propanoyl)-N-{[(2-fluoroethyl)amino]carbo-
nyl}-L-prolinamide LC-MS m/z 401 (MH+)

Example 143

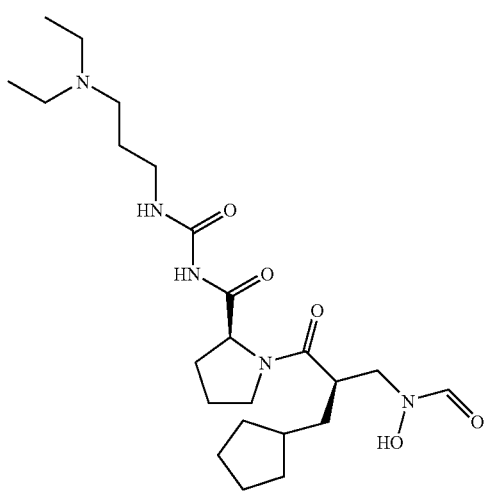

88

1-((2R)-3-cyclopentyl-2-{[formyl(hydroxy)amino]
methyl}propanoyl)-N-({[3-(diethylamino)propyl]
amino}carbonyl)-L-prolinamide LC-MS m/z 468 (MH+)

Example 144

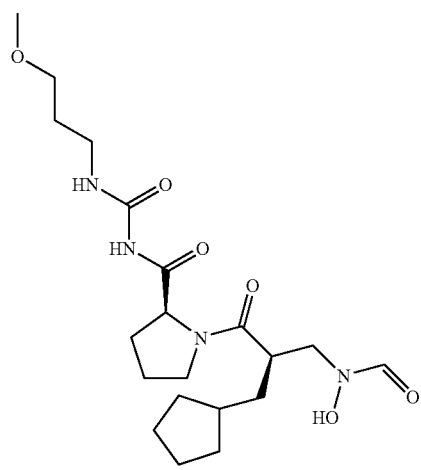

1-((2R)-3-cyclopentyl-2-{[formyl(hydroxy)amino]
methyl}propanoyl)-N-({[3-(methyloxy)propyl]
amino}carbonyl)-L-prolinamide LC-MS m/z 427 (MH+)

Example 145

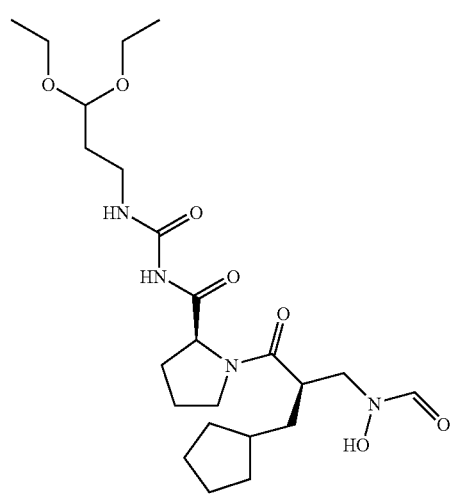

N-({[3,3-bis(ethyloxy)propyl]amino}carbonyl)-1-((2R)-3-cyclopentyl-2-{[formyl(hydroxy)amino]methyl}propanoyl)-L-prolinamide LC-MS m/z 439 (M-C$_2$H$_5$O+)

Example 146

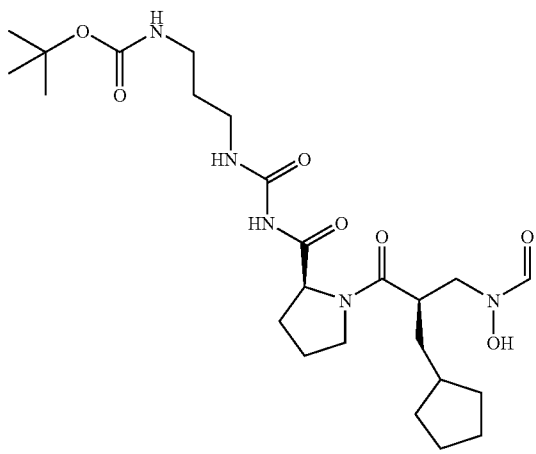

1-((2R)-3-cyclopentyl-2-{[formyl(hydroxy)amino]methyl}propanoyl)-N-({[3-({[(1,1-dimethylethyl)oxy]carbonyl}amino)propyl]amino}carbonyl)-L-prolinamide LC-MS m/z 412 (MH-C$_4$H$_9$OC(O)+)

Example 147

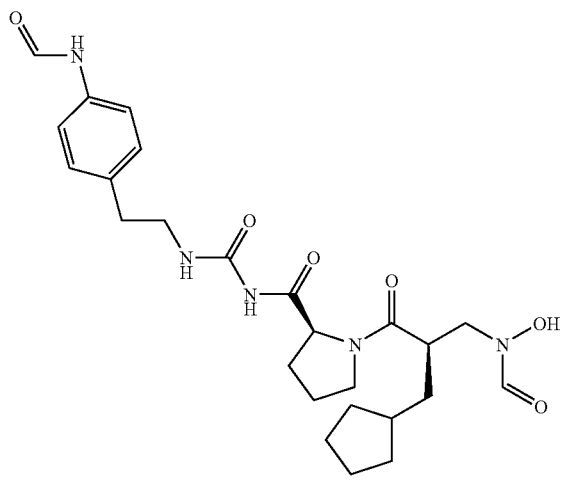

1-((2R)-3-cyclopentyl-2-{[formyl(hydroxy)amino]methyl}propanoyl)-N-[({2-[4-(formylamino)phenyl]ethyl}amino)carbonyl]-L-prolinamide LC-MS m/z 502 (MH+)

Compositions, Administration and Biological Assays

Compounds of Formula (I) and their pharmaceutically acceptable salts may be administered in a standard manner for antibiotics, for example orally, parenterally, sub-lingually, dermally, transdermally, rectally, via inhalation or via buccal administration.

Compositions of Formula (I) and their pharmaceutically acceptable salts which are active when given orally can be formulated as syrups, tablets, capsules, creams and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions or suspensions may be considered, for example, aqueous gums, celluloses, silicates or oils, and incorporated in a soft gelatin capsule shell.

Typical parenteral compositions consist of a solution or suspension of a compound or salt in a sterile aqueous or non-aqueous carrier optionally containing a parenterally acceptable oil, for example, polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example, polymeric glycols, gelatins, cocoa-butter or other low melting vegetable waxes or fats or their synthetic analogs.

Typical dermal and transdermal formulations comprise a conventional aqueous or non-aqueous vehicle, for example, a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula (I) or a pharmaceutically acceptable salt thereof calculated as the free acid. Each dosage unit for intranasal administration contains suitably 1-400 mg and preferably 10 to 200 mg per person. A topical formulation contains suitably 0.01 to 5.0% of a compound of Formula (I).

The daily dosage regimen for oral administration is suitably about 0.01 mg/Kg to 40 mg/Kg of a compound of Formula (I) or a pharmaceutically acceptable salt thereof calculated as the free acid. The daily dosage regimen for parenteral administration is suitably about 0.001 mg/Kg to 40 mg/Kg of a compound of Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

Biological Assays
Bacterial PDF Assay

The biological activity of the compounds of Formula (I) are demonstrated by the following test:

S. aureus or E. coli PDF activity is measured at 25° C., using a continuous enzyme-linked assay developed by Lazennec & Meinnei ("Formate dehydrogenase-coupled spectrophotometric assay of peptide deformylase", Anal. Biochem. 1997, 244, pp. 180-182), with minor modifications. The reaction mixture is contained in 50 uL with 50 mM potassium phosphate buffer (pH 7.6), 15 mM NAD, 0.25 U formate dehydrogenase. The substrate peptide, f-Met-Ala-Ser, is included at the $K_M$ concentration. The reaction is triggered with the addition of 10 nM Def1 enzyme, and absorbance is monitored for 20 min at 340 nm.

Results

The compounds of Examples 1-147 were tested for activity against bacterial PDF and all of these compounds were found to be bacterial PDF inhibitors. These compounds had an $IC_{50}$ of 0.10 μM or less.

Antimicrobial Activity Assay

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically" (incorporated by reference herein). The compound was tested in serial two-fold dilutions ranging from 0.06 to 64 mcg/ml. A panel of 12 strains were evaluated in the assay. This panel consisted of the following laboratory strains: *Staphylococcus aureus* Oxford, *Staphylococcus aureus* WCUH29, *Enterococcus faecalis* I, *Enterococcus faecalis* 7, *Haemophilus influenzae* Q1, *Haemophilus influenzae* NEMC1, *Moraxella catarrhalis* 1502, *Streptococcus pneumoniae* 1629, *Streptococcus pneumoniae* N1387, *Streptococcus pneumoniae* Ery2, *E. coli* 7623 (AcrA-BEFD+) and *E. coli* 120 (AcrAB−). The minimum inhibitory concentration (MIC) was determined as the lowest concentration of compound that inhibited visible growth. A mirror reader was used to assist in determining the MIC endpoint.

Results

The Examples of the present invention were tested in the Antimicrobial Activity Assay. The Examples were shown to have MIC's of 32 mcg/ml or less, against seven or more of the 12 bacterial stains listed above.

*Mycobacterium tuberculosis* Susceptibility Assay

*Mycobacterium tuberculosis* susceptibility testing was performed in 96-well flat-bottom plates inoculated with 1×104 cfu/well. Ten two-fold drug dilutions were carried out in 200 ul of 7H9+ADC medium. After six days at 37° C., minimal inhibitory concentration (MIC) was determined by the addition of 30 ul of Resazurin and plate fluorescence or visual inspection evaluation after two additional days at 37° C.

Results

The compounds of Examples 1, 2, 3, 5, 6, 7, 8, 9, 10, 11, 12, 13, 14, 15, 17, 18, 19 and 20 were all tested in the *Mycobacterium tuberculosis* Susceptibility Assay. The compounds of Examples 1, 2, 3, 5, 6, 7, 8, 9, 10, 11, 12, 14, 15, 17, 18, 19 and 20 were shown to have MIC's of 32 mcg/ml or less against *Mycobacterium tuberculosis* H37Rv.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:
1. A compound according to Formula (I):

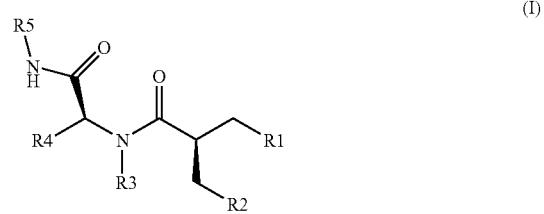

wherein:
R1 is —N(OH)—CHO;
R2 is selected from:
  1) $C_1$-$C_6$-alkyl,
  2) $C_3$-$C_7$-cycloalkyl,
  3) aryl, or
  4) heteroaryl,
    wherein:
      $C_1$-$C_6$-alkyl is optionally substituted by one to three R6 groups;
      each $C_3$-$C_7$-cycloalkyl, aryl, and heteroaryl as defined above optionally are substituted by one to three R7 groups;
R3 and R4 are joined together to form a pyrrolidinyl ring or a pyrrolidinyl ring optionally substituted with one or two C1-C3 alkyl groups;
  1) —C(O)R8,
  2) —C(O)OR8, or
  3) —C(O)NR8R9;
    wherein:
    R6 as defined above independently is selected from:
      1) OH,
      2) $CF_3$,
      3) —NR9R9,
      4) cyano,
      5) $OC_1$-$C_3$-alkyl,
      6) phenyl,
      7) heteroaryl,
      8) heterocycloalkyl,
      9) —NHC(O)$OC_1$-$C_6$-alkyl, or
      10) —NHCOH;

R7 as defined above independently is selected from:
1) OH,
2) halo,
3) cyano,
4) nitro,
5) —NR9R9,
6) $CF_3$,
7) —NHC(O)CH$_3$,
8) —OCH$_3$,
9) $C_1$-$C_6$-alkyl,
10) heteroaryl, or
11) heterocycloalkyl;
R8 as defined above independently is selected from:
1) $C_1$-$C_6$-alkyl,
2) $C_2$-$C_6$-alkenyl,
3) $C_3$-$C_7$-cycloalkyl,
4) phenyl,
5) heteroaryl or
6) heterocycloalkyl,
  wherein:
    $C_1$-$C_6$-alkyl is optionally substituted by one to three R6 groups;
    $C_3$-$C_7$-cycloalkyl, phenyl, and heteroaryl are each optionally substituted by one to three R7 groups; or
    heterocycloalkyl is optionally substituted by one to three R10 groups;
each R9 as defined above independently is selected from:
1) H or
2) $C_1$-$C_6$-alkyl;
R10 as defined above independently is selected from
1) OH,
2) $C_1$-$C_6$-alkyl,
3) phenyl,
4) NH$_2$;
5) —C(O)OC$_1$-$C_6$-alkyl; or
a pharmaceutically acceptable salt thereof.

2. A compound according to claim 1 wherein:
R6 independently is selected from:
1) OH,
2) $CF_3$,
3) —NR9R9,
4) cyano,
5) —OCH$_3$,
6) phenyl, and
7) heteroaryl;
R10 independently is selected from
1) OH,
2) $C_1$-$C_6$-alkyl,
3) phenyl, or
4) NH$_2$;
or a pharmaceutically acceptable salt thereof.

3. A compound according to claim 1, wherein R2 is unsubstituted $C_1$-$C_6$-alkyl or $C_3$-$C_7$-cycloalkyl.

4. A compound according to claim 1, wherein R2 is unsubstituted n-butyl or cyclopentyl; or a pharmaceutically acceptable salt thereof.

5. A compound according to claim 1, wherein R3 and R4 are joined together to form 3,3-dimethyl-pyrrolidinyl ring; or a pharmaceutically acceptable salt thereof.

6. A compound which is:
1-((2R)-3-cyclopentyl-2-{[formyl(hydroxy)amino]methyl}propanoyl)-N-[(4-fluorophenyl)carbonyl]-L-prolinamide;
N-acetyl-1-((2R)-3-cyclopentyl-2-{[formyl(hydroxy)amino]methyl}propanoyl)-L-prolinamide;
1-((2R)-3-cyclopentyl-2-{[formyl(hydroxy)amino]methyl}propanoyl)-N-(phenylcarbonyl)-L-prolinamide;
N-{[4-(acetylamino)phenyl]carbonyl}-1-((2R)-3-cyclopentyl-2-{[formyl(hydroxy)amino]methyl}propanoyl)-L-prolinamide;
1-((2R)-3-cyclopentyl-2-{[formyl(hydroxy)amino]methyl}propanoyl)-N-[(methyloxy)acetyl]-L-prolinamide;
N-[1-((2R)-3-cyclopentyl-2-{[formyl(hydroxy)amino]methyl}propanoyl)-L-prolyl]-6-(trifluoromethyl)-3-pyridinecarboxamide;
1-((2R)-3-cyclopentyl-2-{[formyl(hydroxy)amino]methyl}propanoyl)-N-[1,5-dimethyl-1H-pyrazol-3-yl)carbonyl]-L-prolinamide;
1-((2R)-3-cyclopentyl-2-{[formyl(hydroxy)amino]methyl}propanoyl)-N-[(1,3-dimethyl-1H-pyrazol-5-yl)carbonyl]-L-prolinamide;
1-((2R)-3-cyclopentyl-2-{[formyl(hydroxy)amino]methyl}propanoyl)-N-[(5-methyl-3-isoxazolyl)carbonyl]-L-prolinamide;
1-((2R)-3-cyclopentyl-2-{[formyl(hydroxy)amino]methyl}propanoyl)-N-[(2-fluorophenyl)carbonyl]-L-prolinamide;
1-((2R)-3-cyclopentyl-2-{[formyl(hydroxy)amino]methyl}propanoyl)-N-[(3-fluorophenyl)carbonyl]-L-prolinamide;
1-((2R)-3-cyclopentyl-2-{[formyl(hydroxy)amino]methyl}propanoyl)-N-[(3-fluoro-4-methylphenyl)carbonyl]-L-prolinamide;
N-[1-((2R)-3-cyclopentyl-2-{[formyl(hydroxy)amino]methyl}propanoyl)-L-prolyl]-4-morpholinecarboxamide;
N-[(3-cyanophenyl)carbonyl]-1-((2R)-3-cyclopentyl-2-{[formyl(hydroxy)amino]methyl}propanoyl)-L-prolinamide;
1-((2R)-3-cyclopentyl-2-{[formyl(hydroxy)amino]methyl}propanoyl)-N-[(2,5-difluorophenyl)carbonyl]-L-prolinamide;
1-((2R)-3-cyclopentyl-2-{[formyl(hydroxy)amino]methyl}propanoyl)-N-[(methyloxy)carbonyl]-L-prolinamide;
N-[1-((2R)-3-cyclopentyl-2-{[formyl(hydroxy)amino]methyl}propanoyl)-L-prolyl]-4-pyridinecarboxamide;
1-((2R)-3-cyclopentyl-2-{[formyl(hydroxy)amino]methyl}propanoyl)-N-[(2,6-difluorophenyl)carbonyl]-L-prolinamide;
N-{[(trans-4-aminocyclohexyl)oxy]carbonyl}-1-((2R)-3-cyclopentyl-2-{[formyl(hydroxy)amino]methyl}propanoyl)-L-prolinamide;
N-[1-((2R)-3-cyclopentyl-2-{[formyl(hydroxy)amino]methyl}propanoyl)-L-prolyl]-6-(4-morpholinyl)-3-pyridinecarboxamide;
1-((2R)-3-cyclopentyl-2-{[formyl(hydroxy)amino]methyl}propanoyl)-N-{[4-(1H-pyrazol-1-yl)phenyl]carbonyl}-L-prolinamide;
1-((2R)-3-cyclopentyl-2-{[formyl(hydroxy)amino]methyl}propanoyl)-N-{[(phenylmethyl)oxy]carbonyl}-L-prolinamide;
1-((2R)-3-cyclopentyl-2-{[formyl(hydroxy)amino]methyl}propanoyl)-N-[(ethyloxy)carbonyl]-L-prolinamide;
1-((2R)-3-cyclopentyl-2-{[formyl(hydroxy)amino]methyl}propanoyl)-N-[(tetrahydro-2H-pyran-4-yloxy)carbonyl]-L-prolinamide;

1-((2R)-3-cyclopentyl-2-{[formyl(hydroxy)amino]
methyl}propanoyl)-N-[(cyclopentyloxy)carbonyl]-L-prolinamide;
1-((2R)-3-cyclopentyl-2-{[formyl(hydroxy)amino]
methyl}propanoyl)-N-{[4-(1H-imidazol-1-yl)phenyl]
carbonyl}-L-prolinamide;
N-[(cyclohexyloxy)carbonyl]-1-((2R)-3-cyclopentyl-2-
{[formyl(hydroxy)amino]methyl}propanoyl)-L-prolinamide;
1-((2R)-3-cyclopentyl-2-{[formyl(hydroxy)amino]
methyl}propanoyl)-N-(2-thienylcarbonyl)-L-prolinamide;
1-((2R)-3-cyclopentyl-2-{[formyl(hydroxy)amino]
methyl}propanoyl)-N-[(2-propen-1-yloxy)carbonyl]-L-prolinamide;
2,3-dihydro[1,4]dioxino[2,3-c]pyridin-7-ylmethyl[1-
((2R)-3-cyclopentyl-2-{[formyl(hydroxy)amino]
methyl}propanoyl)-L-prolyl]carbamate;
N-[(cyclobutyloxy)carbonyl]-1-((2R)-3-cyclopentyl-2-
{[formyl(hydroxy)amino]methyl}propanoyl)-L-prolinamide;
1-((2R)-3-cyclopentyl-2-{[formyl(hydroxy)amino]
methyl}propanoyl)-N-{[(1,1-dimethylethyl)oxy]carbonyl}-L-prolinamide;
1-((2R)-3-cyclopentyl-2-{[formyl(hydroxy)amino]
methyl}propanoyl)-N-({[trans-4-(dimethylamino)cyclohexyl]oxy}carbonyl)-L-prolinamide;
N-{[(trans-3-aminocyclobutyl)oxy]carbonyl}-1-((2R)-3-
cyclopentyl-2-{[formyl (hydroxy)amino]
methyl}propanoyl)-L-prolinamide;
1-((2R)-3-cyclopentyl-2-{[formyl(hydroxy)amino]
methyl}propanoyl)-N-{[4-(4-ethyl-1-piperazinyl)phenyl]carbonyl}-L-prolinamide;
1-((2R)-3-cyclopentyl-2-{[formyl(hydroxy)amino]
methyl}propanoyl)-N-(2,2-dimethylpropanoyl)-L-prolinamide;
1-((2R)-3-cyclopentyl-2-{[formyl(hydroxy)amino]
methyl}propanoyl)-N-{[(1-methylethyl)oxy]carbonyl}-L-prolinamide;
1-((2R)-3-cyclopentyl-2-{[formyl(hydroxy)amino]
methyl}propanoyl)-N-{[(1-methyl-3-pyrrolidinyl)oxy]
carbonyl}-L-prolinamide (mixture of diastereomers);
1-((2R)-3-cyclopentyl-2-{[formyl(hydroxy)amino]
methyl}propanoyl)-N-{[(3R)-tetrahydro-3-furanyloxy]
carbonyl}-L-prolinamide;
1-((2R)-3-cyclopentyl-2-{[formyl(hydroxy)amino]
methyl}propanoyl)-N-{[(3S)-tetrahydro-3-furanyloxy]
carbonyl}-L-prolinamide;
1-methyl-3-piperidinyl[1-((2R)-3-cyclopentyl-2-{[formyl
(hydroxy)amino]methyl}propanoyl)-L-prolyl]carbamate (mixture of diastereomers);
1-((2R)-3-cyclopentyl-2-{[formyl(hydroxy)amino]
methyl}propanoyl)-N-({[1-(1-methylethyl)-3-pyrrolidinyl]oxy}carbonyl)-L-prolinamide (mixture of diastereomers);
1-((2R)-3-cyclopentyl-2-{[formyl(hydroxy)amino]
methyl}propanoyl)-N-(4-isoxazolylcarbonyl)-L-prolinamide;
1-((2R)-3-cyclopentyl-2-{[formyl(hydroxy)amino]
methyl}propanoyl)-N-[(tetrahydro-2H-thiopyran-4-yloxy)carbonyl]-L-prolinamide;
1-((2R)-3-cyclopentyl-2-{[formyl(hydroxy)amino]
methyl}propanoyl)-N-{[(1,1-dioxidotetrahydro-2H-thiopyran-4-yl)oxy]carbonyl}-L-prolinamide;
1-((2R)-3-cyclopentyl-2-{[formyl(hydroxy)amino]
methyl}propanoyl)-N-({[(1S)-1-methyl-2-(methyloxy)
ethyl]oxy}carbonyl)-L-prolinamide;
1-((2R)-3-cyclopentyl-2-{[formyl(hydroxy)amino]
methyl}propanoyl)-N-({[(1R)-1-methyl-2-(methyloxy)ethyl]oxy}carbonyl)-L-prolinamide;
1-((2R)-3-cyclopentyl-2-{[formyl(hydroxy)amino]
methyl}propanoyl)-N-{[4-(1-piperazinyl)phenyl]carbonyl}-L-prolinamide;
1-((2R)-3-cyclopentyl-2-{[formyl(hydroxy)amino]
methyl}propanoyl)-N-(2-methylpropanoyl)-L-prolinamide;
1-((2R)-3-cyclopentyl-2-{[formyl(hydroxy)amino]
methyl}propanoyl)-N-(3-methylbutanoyl)-L-prolinamide;
N-[1-((2R)-3-cyclopentyl-2-{[formyl(hydroxy)amino]
methyl}propanoyl)-L-prolyl]-2-pyridinecarboxamide;
N-[1-((2R)-3-cyclopentyl-2-{[formyl(hydroxy)amino]
methyl}propanoyl)-L-prolyl]-3-pyridinecarboxamide;
N-(cyclobutylcarbonyl)-1-((2R)-3-cyclopentyl-2-
{[formyl(hydroxy)amino]methyl}propanoyl)-L-prolinamide;
1-((2R)-3-cyclopentyl-2-{[formyl(hydroxy)amino]
methyl}propanoyl)-N-{(ethylamino)carbonyl}-L-prolinamide;
1-((2R)-3-cyclopentyl-2-{[formyl(hydroxy)amino]
methyl}propanoyl)-N-(cyclopropylcarbonyl)-L-prolinamide;
N-(cyclopentylacetyl)-1-((2R)-3-cyclopentyl-2-{[formyl
(hydroxy)amino]methyl}propanoyl)-L-prolinamide;
N-(cyclopentylcarbonyl)-1-((2R)-3-cyclopentyl-2-
{[formyl(hydroxy)amino]methyl}propanoyl)-L-prolinamide;
N-(cyclohexylcarbonyl)-1-((2R)-3-cyclopentyl-2-
{[formyl(hydroxy)amino]methyl}propanoyl)-L-prolinamide;
1,1-dimethylethyl 3-({[1-((2R)-3-cyclopentyl-2-{[formyl
(hydroxy)amino]methyl}propanoyl)-L-prolyl]
amino}carbonyl)-1-pyrrolidinecarboxylate (mixture of diastereomers);
N-(cyclopentylcarbonyl)-1-((2R)-2-{[formyl(hydroxy)
amino]methyl}heptanoyl)-L-prolinamide;
N-(2,2-dimethylpropanoyl)-1-((2R)-2-{[formyl(hydroxy)
amino]methyl}heptanoyl)-L-prolinamide;
1-((2R)-3-cyclopentyl-2-{[formyl(hydroxy)amino]
methyl}propanoyl)-N-({[(methyloxy)carbonyl]
amino}carbonyl)-L-prolinamide;
1-((2R)-3-cyclopentyl-2-{[formyl(hydroxy)amino]
methyl}propanoyl)-N-{[(1,1-dimethylethyl)amino]carbonyl}-L-prolinamide;
N-{[(1,1-dimethylethyl)oxy]carbonyl}-1-((2R)-2-
{[formyl(hydroxy)amino]methyl}heptanoyl)-L-prolinamide;
N-[(ethylamino)carbonyl]-1-((2R)-2-{[formyl(hydroxy)
amino]methyl}heptanoyl)-L-prolinamide;
$N^1$-(cyclopentylcarbonyl)-$N^2$-((2R)-3-cyclopentyl-2-
{[formyl(hydroxy)amino]methyl}propanoyl)-3-methyl-L-valinamide;
$N^2$-((2R)-3-cyclopentyl-2-{[formyl(hydroxy)amino]
methyl}propanoyl)-$N^1$-(2,2-dimethylpropanoyl)-3-methyl-L-valinamide;
$N^2$-((2R)-3-cyclopentyl-2-{[formyl(hydroxy)amino]
methyl}propanoyl)-$N^1$-{[(1,1-dimethylethyl)oxy]carbonyl}-3-methyl-L-valinamide;
1-((2R)-3-cyclopentyl-2-{[formyl(hydroxy)amino]
methyl}propanoyl)-N-{[(1-methylethyl)amino]carbonyl}-L-prolinamide;
N-[(cyclopentylamino)carbonyl]-1-((2R)-3-cyclopentyl-
2-{[formyl(hydroxy)amino]methyl}propanoyl)-L-prolinamide;

N-[(butylamino)carbonyl]-1-((2R)-3-cyclopentyl-2-{[formyl(hydroxy)amino]methyl}propanoyl)-L-prolinamide;

$N^2$-((2R)-3-cyclopentyl-2-{[formyl(hydroxy)amino]methyl}propanoyl)-$N^1$-[(ethylamino)carbonyl]-3-methyl-L-valinamide;

1-((2R)-3-cyclopentyl-2-{[formyl(hydroxy)amino]methyl}propanoyl)-N-({[4-(methyloxy)phenyl]amino}carbonyl)-L-prolinamide;

N-[(cyclohexylamino)carbonyl]-1-((2R)-3-cyclopentyl-2-{[formyl(hydroxy)amino]methyl}propanoyl)-L-prolinamide;

$N^2$-((2R)-3-cyclopentyl-2-{[formyl(hydroxy)amino]methyl}propanoyl)-3-methyl-$N^1$-[(methyloxy)carbonyl]-L-valinamide;

1-((2R)-3-cyclopentyl-2-{[formyl(hydroxy)amino]methyl}propanoyl)-N-[(propylamino)carbonyl]-L-prolinamide;

1-((2R)-3-cyclopentyl-2-{[formyl(hydroxy)amino]methyl}propanoyl)-N-[(2-propen-1-ylamino)carbonyl]-L-prolinamide;

1-((2R)-3-cyclopentyl-2-{[formyl(hydroxy)amino]methyl}propanoyl)-N-[(dimethylamino)carbonyl]-L-prolinamide;

1-((2R)-3-cyclopentyl-2-{[formyl(hydroxy)amino]methyl}propanoyl)-N-{[(phenylmethyl)amino]carbonyl}-L-prolinamide;

1-((2R)-3-cyclopentyl-2-{[formyl(hydroxy)amino]methyl}propanoyl)-3,3-dimethyl-N-[(methyloxy)carbonyl]-L-prolinamide;

1-((2R)-3-cyclopentyl-2-{[formyl(hydroxy)amino]methyl}propanoyl)-N-{[(2-phenylethyl)amino]carbonyl}-L-prolinamide;

1-((2R)-3-cyclopentyl-2-{[formyl(hydroxy)amino]methyl}propanoyl)-N-[(methylamino)carbonyl]-L-prolinamide;

1-((2R)-3-cyclopentyl-2-{[formyl(hydroxy)amino]methyl}propanoyl)-N-{[(4-phenylbutyl)amino]carbonyl}-L-prolinamide;

1-((2R)-3-cyclopentyl-2-{[formyl(hydroxy)amino]methyl}propanoyl)-N-({[(2S)-2-hydroxypropyl]amino}carbonyl)-L-prolinamide;

1-((2R)-3-cyclopentyl-2-{[formyl(hydroxy)amino]methyl}propanoyl)-N-({[(2R)-2-hydroxypropyl]amino}carbonyl)-L-prolinamide;

1-((2R)-3-cyclopentyl-2-{[formyl(hydroxy)amino]methyl}propanoyl)-N-({[2-(3-pyridinyl)ethyl]amino}carbonyl)-L-prolinamide hydrochloride;

1-((2R)-3-cyclopentyl-2-{[formyl(hydroxy)amino]methyl}propanoyl)-N-{[(3-phenylpropyl)amino]carbonyl}-L-prolinamide;

N-({[2-(1-benzofuran-2-yl)ethyl]amino}carbonyl)-1-((2R)-3-cyclopentyl-2-{[formyl(hydroxy)amino]methyl}propanoyl)-L-prolinamide;

1-((2R)-3-cyclopentyl-2-{[formyl(hydroxy)amino]methyl}propanoyl)-N-({[2-(3,5-dimethyl-1H-pyrazol-4-yl)ethyl]amino}carbonyl)-L-prolinamide;

ethyl 4-[({[1-((2R)-3-cyclopentyl-2-{[formyl(hydroxy)amino]methyl}propanoyl)-L-prolyl]amino}carbonyl)amino]-1-piperidinecarboxylate;

1-((2R)-3-cyclopentyl-2-{[formyl(hydroxy)amino]methyl}propanoyl)-N-({[2-(2-pyridinyl)ethyl]amino}carbonyl)-L-prolinamide;

1-((2R)-3-cyclopentyl-2-{[formyl(hydroxy)amino]methyl}propanoyl)-N-({[2-(2-pyrazinyl)ethyl]amino}carbonyl)-L-prolinamide;

1-((2R)-3-cyclopentyl-2-{[formyl(hydroxy)amino]methyl}propanoyl)-N-({[2-(4-pyridinyl)ethyl]amino}carbonyl)-L-prolinamide;

1-((2R)-3-cyclopentyl-2-{[formyl(hydroxy)amino]methyl}propanoyl)-N-{[(4-hydroxybutyl)amino]carbonyl}-L-prolinamide;

1-((2R)-3-cyclopentyl-2-{[formyl(hydroxy)amino]methyl}propanoyl)-N-{[(5-hydroxypentyl)amino]carbonyl}-L-prolinamide;

1-((2R)-3-cyclopentyl-2-{[formyl(hydroxy)amino]methyl}propanoyl)-N-({[3-(dimethylamino)propyl]amino}carbonyl)-L-prolinamide;

1-((2R)-3-cyclopentyl-2-{[formyl(hydroxy)amino]methyl}propanoyl)-N-({[2-[5-(methyloxy)-1H-indol-3-yl]ethyl]amino}carbonyl)-L-prolinamide;

1-((2R)-3-cyclopentyl-2-{[formyl(hydroxy)amino]methyl}propanoyl)-N-({[3-(2-oxo-1-pyrrolidinyl)propyl]amino}carbonyl)-L-prolinamide;

1-((2R)-3-cyclopentyl-2-{[formyl(hydroxy)amino]methyl}propanoyl)-N-({[(1-methyl-1H-imidazol-2-yl)methyl]amino}carbonyl)-L-prolinamide;

1-((2R)-3-cyclopentyl-2-{[formyl(hydroxy)amino]methyl}propanoyl)-N-({[(1,5-dimethyl-1H-pyrazol-4-yl)methyl]amino}carbonyl)-L-prolinamide;

1-((2R)-3-cyclopentyl-2-{[formyl(hydroxy)amino]methyl}propanoyl)-N-({[3-(4-morpholinyl)propyl]amino}carbonyl)-L-prolinamide;

1-((2R)-3-cyclopentyl-2-{[formyl(hydroxy)amino]methyl}propanoyl)-N-{[(2-phenylpropyl)amino]carbonyl}-L-prolinamide (mixture of diastereomers);

1-((2R)-3-cyclopentyl-2-{[formyl(hydroxy)amino]methyl}propanoyl)-N-({[2-(1-piperidinyl)ethyl]amino}carbonyl)-L-prolinamide formate;

1-((2R)-3-cyclopentyl-2-{[formyl(hydroxy)amino]methyl}propanoyl)-N-{[(2-hydroxyethyl)amino]carbonyl}-L-prolinamide;

1-((2R)-3-cyclopentyl-2-{[formyl(hydroxy)amino]methyl}propanoyl)-N-({[2-(1-pyrrolidinyl)ethyl]amino}carbonyl)-L-prolinamide formate;

1-((2R)-3-cyclopentyl-2-{[formyl(hydroxy)amino]methyl}propanoyl)-N-[{3-[(1-methylethyl)oxy]propyl}amino)carbonyl]-L-prolinamide;

N-({[2-(4-aminophenyl)ethyl]amino}carbonyl)-1-((2R)-3-cyclopentyl-2-{[formyl(hydroxy)amino]methyl}propanoyl)-L-prolinamide;

1-((2R)-3-cyclopentyl-2-{[formyl(hydroxy)amino]methyl}propanoyl)-N-{[(3-hydroxypropyl)amino]carbonyl}-L-prolinamide;

N-(aminocarbonyl)-1-((2R)-3-cyclopentyl-2-{[formyl(hydroxy)amino]methyl}propanoyl)-3,3-dimethyl-L-prolinamide;

1-((2R)-3-cyclopentyl-2-{[formyl(hydroxy)amino]methyl}propanoyl)-N-[(cyclopropylamino)carbonyl]-3,3-dimethyl-L-prolinamide;

1-((2R)-3-cyclopentyl-2-{[formyl(hydroxy)amino]methyl}propanoyl)-3,3-dimethyl-N-{[(3R)-tetrahydro-3-furanyloxy]carbonyl}-L-prolinamide;

1-((2R)-3-cyclopentyl-2-{[formyl(hydroxy)amino]methyl}propanoyl)-N-{[(tetrahydro-2-furanylmethyl)amino]carbonyl}-L-prolinamide (mixture of diastereomers);

N-[(cyclobutylamino)carbonyl]-1-((2R)-3-cyclopentyl-2-{[formyl(hydroxy)amino]methyl}propanoyl)-L-prolinamide;

N-({[2-(6-amino-5-fluoro-3-pyridinyl)ethyl]amino}carbonyl)-1-((2R)-3-cyclopentyl-2-{[formyl(hydroxy)amino]methyl}propanoyl)-L-prolinamide;

1-((2R)-3-cyclopentyl-2-{[formyl(hydroxy)amino]methyl}propanoyl)-3,3-dimethyl-N-{[(2-oxetanylmethyl)oxy]carbonyl}-L-prolinamide;

1-((2R)-3-cyclopentyl-2-{[formyl(hydroxy)amino]methyl}propanoyl)-N-[(ethylamino)carbonyl]-3,3-dimethyl-L-prolinamide;

1-((2R)-3-cyclopentyl-2-{[formyl(hydroxy)amino]methyl}propanoyl)-N-[(cyclopropylamino)carbonyl]-L-prolinamide;

1-((2R)-3-cyclopentyl-2-{[formyl(hydroxy)amino]methyl}propanoyl)-3,3-dimethyl-N-[(methylamino)carbonyl]-L-prolinamide;

1-((2R)-3-cyclopentyl-2-{[formyl(hydroxy)amino]methyl}propanoyl)-3,3-dimethyl-N-({[(3-methyl-3-oxetanyl)methyl]oxy}carbonyl)-L-prolinamide;

1-((2R)-3-cyclopentyl-2-{[formyl(hydroxy)amino]methyl}propanoyl)-3,3-dimethyl-N-[(3-oxetanyloxy)carbonyl]-L-prolinamide;

1-((2R)-3-cyclopentyl-2-{[formyl(hydroxy)amino]methyl}propanoyl)-N-{[(3S)-tetrahydro-3-furanylamino]carbonyl}-L-prolinamide;

1-((2R)-3-cyclopentyl-2-{[formyl(hydroxy)amino]methyl}propanoyl)-N-{[(3-methylbutyl)amino]carbonyl}-L-prolinamide;

1-((2R)-3-cyclopentyl-2-{[formyl(hydroxy)amino]methyl}propanoyl)-N-({[2-(4-pyridazinyl)ethyl]amino}carbonyl)-L-prolinamide;

1-((2R)-3-cyclopentyl-2-{[formyl(hydroxy)amino]methyl}propanoyl)-3,3-dimethyl-N-({[(1S)-1-methyl-2-(methyloxy)ethyl]oxy}carbonyl)-L-prolinamide;

1-((2R)-3-cyclopentyl-2-{[formyl(hydroxy)amino]methyl}propanoyl)-3,3-dimethyl-N-({[(1R)-1-methyl-2-(methyloxy)ethyl]oxy}carbonyl)-L-prolinamide;

1-((2R)-3-cyclopentyl-2-{[formyl(hydroxy)amino]methyl}propanoyl)-3,3-dimethyl-N-[(tetrahydro-2H-pyran-4-yloxy)carbonyl]-L-prolinamide;

1-((2R)-3-cyclopentyl-2-{[formyl(hydroxy)amino]methyl}propanoyl)-N-({[2-(methyloxy)ethyl]amino}carbonyl)-L-prolinamide;

N-(aminocarbonyl)-1-((2R)-3-cyclopentyl-2-{[formyl(hydroxy)amino]methyl}propanoyl)-L-prolinamide;

N-{[(trans-3-cyanocyclobutyl)amino]carbonyl}-1-((2R)-3-cyclopentyl-2-{[formyl(hydroxy)amino]methyl}propanoyl)-L-prolinamide;

1-((2R)-3-cyclopentyl-2-{[formyl(hydroxy)amino]methyl}propanoyl)-N-{[(1-hydroxy-1,2,3,4-tetrahydro-2-naphthalenyl)amino]carbonyl}-L-prolinamide (mixture of trans-diastereomers);

1-((2R)-3-cyclopentyl-2-{[formyl(hydroxy)amino]methyl}propanoyl)-3,3-dimethyl-N-{[(3S)-tetrahydro-3-furanyloxy]carbonyl}-L-prolinamide;

N-({[2-(6-amino-5-chloro-3-pyridinyl)ethyl]amino}carbonyl)-1-((2R)-3-cyclopentyl-2-{[formyl(hydroxy)amino]methyl}propanoyl)-L-prolinamide;

1-((2R)-3-cyclopentyl-2-{[formyl(hydroxy)amino]methyl}propanoyl)-N-{[(2,3-dihydro-1,4-benzodioxin-2-ylmethyl)amino]carbonyl}-L-prolinamide (mixture of diastereomers);

1-((2R)-3-cyclopentyl-2-{[formyl(hydroxy)amino]methyl}propanoyl)-N-{[(2-imidazo[1,2-a]pyridin-6-ylethyl)amino]carbonyl}-L-prolinamide formate;

N-[(cyclobutyloxy)carbonyl]-1-((2R)-3-cyclopentyl-2-{[formyl(hydroxy)amino]methyl}propanoyl)-3,3-dimethyl-L-prolinamide;

1-((2R)-3-cyclopentyl-2-{[formyl(hydroxy)amino]methyl}propanoyl)-N-({[(2S)-2-hydroxy-2-phenylethyl]amino}carbonyl)-L-prolinamide;

1-((2R)-3-cyclopentyl-2-{[formyl(hydroxy)amino]methyl}propanoyl)-N-({[(2R)-2-hydroxy-2-phenylethyl]amino}carbonyl)-L-prolinamide;

1-((2R)-3-cyclopentyl-2-{[formyl(hydroxy)amino]methyl}propanoyl)-N-{[(5-methyl-1H-pyrazol-3-yl)amino]carbonyl}-L-prolinamide;

1-((2R)-3-cyclopentyl-2-{[formyl(hydroxy)amino]methyl}propanoyl)-N-[(2,3-dihydro-1H-inden-2-ylamino)carbonyl]-L-prolinamide;

1-((2R)-3-cyclopentyl-2-{[formyl(hydroxy)amino]methyl}propanoyl)-N-({[2-(1H-pyrazol-1-yl)ethyl]amino}carbonyl)-L-prolinamide;

1-((2R)-3-cyclopentyl-2-{[formyl(hydroxy)amino]methyl}propanoyl)-N-({[2-(diethylamino)ethyl]amino}carbonyl)-L-prolinamide;

1-((2R)-3-cyclopentyl-2-{[formyl(hydroxy)amino]methyl}propanoyl)-N-{[(2-fluoroethyl)amino]carbonyl}-L-prolinamide;

1-((2R)-3-cyclopentyl-2-{[formyl(hydroxy)amino]methyl}propanoyl)-N-({[3-(diethylamino)propyl]amino}carbonyl)-L-prolinamide;

1-((2R)-3-cyclopentyl-2-{[formyl(hydroxy)amino]methyl}propanoyl)-N-({[3-(methyloxy)propyl]amino}carbonyl)-L-prolinamide;

N-({[3,3-bis(ethyloxy)propyl]amino}carbonyl)-1-((2R)-3-cyclopentyl-2-{[formyl(hydroxy)amino]methyl}propanoyl)-L-prolinamide;

1-((2R)-3-cyclopentyl-2-{[formyl(hydroxy)amino]methyl}propanoyl)-N-({[3-({[(1,1-dimethylethyl)oxy]carbonyl}amino)propyl]amino}carbonyl)-L-prolinamide;

1-((2R)-3-cyclopentyl-2-{[formyl(hydroxy)amino]methyl}propanoyl)-N-[({2-[4-(formylamino)phenyl]ethyl}amino)carbonyl]-L-prolinamide; or a pharmaceutically acceptable salt thereof.

7. A method of treating a bacterial infection which comprises administering a compound according to claim 1, or a pharmaceutically acceptable salt thereof to a subject in need thereof.

8. A pharmaceutical composition comprising a compound according to claim 1, or a pharmaceutically acceptable salt thereof, and one or more pharmaceutically acceptable excipients.

* * * * *